United States Patent
Chasin et al.

(10) Patent No.: US 6,413,975 B1
(45) Date of Patent: Jul. 2, 2002

(54) PURINE DERIVATIVES HAVING PHOSPHODIESTERASE IV INHIBITION ACTIVITY

(75) Inventors: Mark Chasin, Manalapan, NJ (US); David J. Cavalla, Cambridge (GB); Peter Hofer, Liestal (CH); Andre Gehrig, Basel (CH); Peter Wintergerst, Basel (CH)

(73) Assignee: Euro-Celtique, S.A., Luxembourg (LU)

( * ) Notice: Subject to any disclaimer, the term of this patent is extended or adjusted under 35 U.S.C. 154(b) by 0 days.

(21) Appl. No.: 09/539,571

(22) Filed: Mar. 31, 2000

Related U.S. Application Data

(63) Continuation-in-part of application No. 09/285,473, filed on Apr. 2, 1999.

(51) Int. Cl.7 .................. C07D 473/34; C07D 473/18; C07D 473/24; A61K 31/52; A61P 11/06

(52) U.S. Cl. .................. 514/261; 544/277; 544/267; 544/268; 544/271; 544/272; 544/273; 544/276

(58) Field of Search .................. 544/277; 514/261

(56) References Cited

U.S. PATENT DOCUMENTS

| | | | |
|---|---|---|---|
| 2,691,654 A | 10/1954 | Hitchings | 544/277 |
| 2,697,709 A | 12/1954 | Hitchings et al. | 260/252 |
| 2,844,577 A | 7/1958 | Acker | 544/277 |
| 2,903,455 A | 9/1959 | Strong | 544/277 |
| 2,956,998 A | 10/1960 | Baizer | 544/277 |
| 2,957,875 A | 10/1960 | Lyttle | 544/277 |
| 2,966,488 A | 12/1960 | Shive | 544/277 |
| 3,079,378 A | 2/1963 | Schroeder et al. | 260/211.5 |
| 3,135,753 A | 6/1964 | Hitchings | 540/265 |
| 3,215,696 A | 11/1965 | Denayer | 544/277 |
| 3,225,046 A | 12/1965 | Zwahlen | 544/277 |
| 3,669,979 A | 6/1972 | Freyermuth | 260/304 |
| 3,952,001 A | 4/1976 | Brookes et al. | 260/308 |
| 4,241,063 A | 12/1980 | Natio et al. | 424/253 |
| 4,361,699 A | 11/1982 | Rasmusson et al. | 544/277 |
| RE31,429 E | 10/1983 | Tull et al. | 544/277 |
| 4,407,802 A | 10/1983 | Graham et al. | 424/253 |
| 4,492,592 A | 1/1985 | Diaz et al. | 62/18 |
| 4,728,644 A | 3/1988 | Yuki et al. | 514/212 |
| 4,883,801 A | 11/1989 | Nathanson | 514/263 |
| 4,971,972 A | 11/1990 | Doll et al. | 514/265 |
| 4,981,857 A | 1/1991 | Daluge et al. | 514/263 |
| 5,057,517 A | 10/1991 | Johnston et al. | 514/254 |
| 5,091,431 A | 2/1992 | Tulshian et al. | 514/262 |
| 5,110,818 A | 5/1992 | Allgeier | 514/261 |
| 5,117,830 A | 6/1992 | McAfee | 128/654 |
| 5,177,074 A | 1/1993 | Allen et al. | 514/234.2 |
| 5,270,316 A | 12/1993 | Suzuki et al. | 514/267 |
| 5,290,782 A | 3/1994 | Suzuki et al. | 514/263 |
| 5,939,422 A | * 8/1999 | Cavalla | 544/277 |
| 6,211,367 B1 | * 4/2001 | Cavalla et al. | 544/180 |
| 6,228,859 B1 | * 5/2001 | Cavalla et al. | 514/261 |

FOREIGN PATENT DOCUMENTS

| | | |
|---|---|---|
| EP | 0203721 | 12/1986 |
| EP | 256692 | 2/1988 |
| EP | 0675124 | 10/1995 |
| EP | 0728759 | 8/1996 |
| FR | 1548252 | 10/1968 |
| GB | 1077689 | 8/1967 |
| GB | 2041359 | 9/1980 |
| GB | 2120665 | 12/1983 |
| JP | 7606986 | 1/1976 |
| JP | 5121529 | 2/1976 |
| JP | 7654587 | 5/1976 |
| NZ | 0215948 | 10/1989 |
| WO | 8706576 | 11/1987 |
| WO | 9314081 | 7/1993 |
| WO | 9314082 | 7/1993 |
| WO | 9325517 | 12/1993 |
| WO | 9402465 | 2/1994 |
| WO | 9410118 | 5/1994 |
| WO | 9412461 | 6/1994 |
| WO | 9414742 | 7/1994 |
| WO | 9414800 | 7/1994 |
| WO | 9420446 | 9/1994 |
| WO | 9420455 | 9/1994 |
| WO | 9422859 | 10/1994 |

OTHER PUBLICATIONS

Fuji et al, Chem Pharm Bull 41(8) 1363, Aug. 1993.*
Yu et al, Phytochemistry 20(6) 1191, Jun. 1981.*
Robins, JACS, 74, 1952, 3624–.
Stafford and Feldman, "Annual Reports in Medicinal Chemistry", Academic Press, San Diego, 1966, Chapt. 8, p. 76–78.
Gertrude Elion, JOC, 27, 1962, 2478–2491.
Bergman & Tamari, J. Chem. Soc., 1961, 4468–4472.
Shimada, Junichi, Kuroda, Takeshi, Suzuki, Fumio, J. Heterocycl. Chem., 30(1), 241–6 (English) 1993.
Buell, J. Biol. Chem., 72, 1927, 745.

(List continued on next page.)

Primary Examiner—Mark L. Berch
(74) Attorney, Agent, or Firm—Davidson, Davidson & Kappel, LLC

(57) ABSTRACT

Disclosed are compounds of the formula:

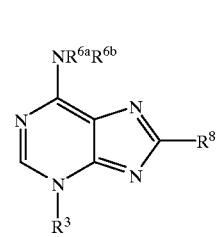

(I)

wherein $R^3$, $R^{6a}$, $R^{6b}$ and $R^8$ are substituted as disclosed herein. The compounds are effective in effecting PDE IV inhibition in patients in need thereof.

11 Claims, No Drawings

OTHER PUBLICATIONS

Suzuki, Fumio, Shimada, Junichi, Nonaka, Hiromi, Ishi, Akio, Shiozaki, Shizuo, Ichikawa, Shunji, Ono, Eikichi, J. Med. Chem., 35(19), 3578–81 (English) 1992.

Moharra, Hussieny H., Mansour, S.A., Osman, A.N., Egypt. J. Pharm. Sci., 31(1–4), 487–94 (English).

S.–C. J. Fu et al., JOC, 30, 1965, 1916–1920.

Henry Koppel & Roland Robins, JOC, 23, 1958, 1457–1460.

Giner–Sorolla, Alfred, Segarra, Jay T., Hadden, John W., Nucleic Acid Chem., vol. 4, 10–15.

Girshovich, Chem Abs 116, 173873 (1991).

Montgomery, J.A.C.S. 81, 3963 (1959).

Elion, Chem Abe 53, 6243h (1957).

Isomura, Y. et al., "Studies on the synthesis and Anti–Inflammatory Activity of 2,6–Di–tert–butylphenols with a Heterocyclic Group at the 4–Position. I." Chem. Pharm. Bull. 31 (9) 3168–3178 (1983).

Ashton, et al., "Selective Type IV Phosphodiesterase Inhibitors as Antiasthmatic Agents. The Synthesis and Biological Activities of 3–(Cyclopentyloxy)–4–methoxybenzamides and Analogues." J. Med. Chem., vol. 37, No. 11 1696–1703 (1994).

K.R.H. Woolridge and R. Slack, "The Synthesis of Some 6–Thioxanthines." Annex IV, 1863–1868 (1962).

Fuji, J. Med. Chem. 22, 125 (1979).

Reitz, J. Org. Chem 55, 5761 (1990).

Itaya, Zet. Letters 23, 2203 (1982).

Enoki, Chem Abs 85, 5692 (1976).

Kazimierczuk, Chem Abs 82, 125358 (1974).

Ulbricht, Chem Abs 75, 49027b (1971).

Aida, Chem Abs 86, 43746 (1976).

Enoki, Chem Abs 84, 180299 (1976).

G.T. Rogers et al.: "Synthesis of 3–methylisoguanine '6–Amino–3–methylpurin–2(3H)– One!" Journal of the Chemical Society C, No. 12, 1971, pp. 2364–2366, XP002095992.

Elion, G. "Some new n–methylpurines" CIBA Foundation Symp. Chem. Biol. Purines, 1957, pp.39–49.

Glusenkamp, K, et al., Tautomer–specific anti–(M–3–substituted)–adenine antibodies: new tools in molecular dosimetry & epidemiology, Agnew Chem. Int. Ed. Engl. 1993, 32, No. 11, pp. 1640–1641.

* cited by examiner

PURINE DERIVATIVES HAVING PHOSPHODIESTERASE IV INHIBITION ACTIVITY

This application is a continuation-in-part of U.S. Ser. No. 09/285,473, filed Apr. 2, 1999, the disclosure of which is herein incorporated by reference.

BACKGROUND OF THE INVENTION

Asthma is a complex disease involving the concerted actions of multiple inflammatory and immune cells, spasmogens, inflammatory mediators, cytokines and growth factors. In recent practice there have been four major classes of compounds used in the treatment of asthma, namely bronchodilators (e.g., β-adrenoceptor agonists), anti-inflammatory agents (e.g., corticosteroids), prophylactic anti-allergic agents (e.g., cromolyn sodium) and xanthines (e.g., theophylline) which appear to possess both bronchodilating and anti-inflammatory activity.

Theophylline has been a preferred drug of first choice in the treatment of asthma. Although it has been touted for its direct bronchodilatory action, theophylline's therapeutic value is now believed to also stem from anti-inflammatory activity. Its mechanism of action remains unclear. However, it is believed that several of its cellular activities are important in its activity as an anti-asthmatic, including cyclic nucleotide phosphodiesterase inhibition, adenosine receptor antagonism, stimulation of catecholamine release, and its ability to increase the number and activity of suppressor T-lymphocytes. While all of these may actually contribute to its activity, only PDE inhibition may account for both the anti-inflammatory and bronchodilatory components. However, theophylline is known to have a narrow therapeutic index and a wide range of untoward side effects which are considered problematic.

Of the activities mentioned above, theophylline's activity in inhibiting cyclic nucleotide phosphodiesterase has received considerable attention recently. Cyclic nucleotide phosphodiesterases (PDEs) have received considerable attention as molecular targets for anti-asthmatic agents. Cyclic 3',5'-adenosine monophosphate (cAMP) and cyclic 3',5'-guanosine monophosphate (cGMP) are known second messengers that mediate the functional responses of cells to a multitude of hormones, neurotransmitters and autocoids. At least two therapeutically important effects could result from phosphodiesterase inhibition, and the consequent rise in intracellular adenosine 3',5'-monophosphate (cAMP) or guanosine 3',5'-monophosphate (CGMP) in key cells in the pathophysiology of asthma. These are smooth muscle relaxation (resulting in bronchodilation) and anti-inflammatory activity.

It has become known that there are multiple, distinct PDE isoenzymes which differ in their cellular distribution. A variety of inhibitors possessing a marked degree of selectivity for one isoenzyme or the other have been synthesized.

The structure-activity relationships (SAR) of isozyme-selective inhibitors has been discussed in detail, e.g., in the article of Theodore J. Torphy, et al., "Novel Phosphodiesterase Inhibitors For The Therapy Of Asthma", Drug News & Prospectives, 6(4) May 1993, pages 203–214. The PDE enzymes can be grouped into five families according to their specificity toward hydrolysis of cAMP or cGMP, their sensitivity to regulation by calcium, calmodulin or cGMP, and their selective inhibition by various compounds. PDE I is stimulated by $Ca^{2+}$/calmodulin. PDE II is cGMP-stimulated, and is found in the heart and adrenals. PDE III is cGMP-inhibited, and inhibition of this enzyme creates positive inotropic activity. PDE IV is cAMP specific, and its inhibition causes airway relaxation, antiinflammatory and antidepressant activity. PDE V appears to be important in regulating cGMP content in vascular smooth muscle, and therefore PDE V inhibitors may have cardiovascular activity.

While there are compounds derived from numerous structure activity relationship studies which provide PDE III inhibition, the number of structural classes of PDE IV inhibitors is relatively limited. Analogues of rolipram, which has the following structural formula (A):

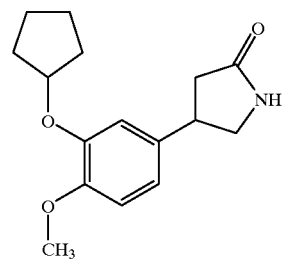

and of RO-20-1724, which has the following structural formula (B):

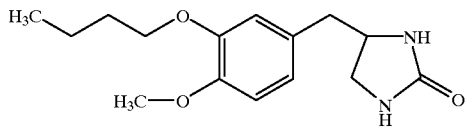

have been studied.

U.S. Pat. No. 4,308,278 discloses compounds of the formula (C)

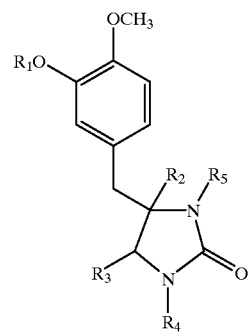

wherein $R_1$ is $(C_3-C_6)$cycloalkyl or benzyl; each of $R_2$ and $R_3$ is hydrogen or $(C_1-C_4)$alkyl; $R_4$ is $R_2$ or alkoxycarbonyl; and $R_5$ is hydrogen or alkoxycarbonyl.

Compounds of Formula (D) are disclosed in U.S. Pat. No. 3,636,039. These compounds are benzylimidazolidinones which act as hypertensive agents.

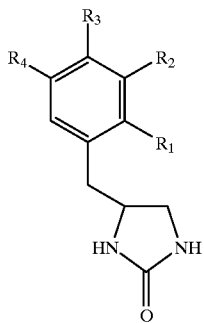

Substituents $R_1$–$R_4$ in Formula D represent a variety of groups, including hydrogen and lower alkyl.

PCT publication WO 87/06576 discloses antidepressants of Formula E:

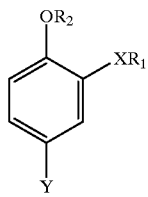

wherein $R_1$ is a polycycloalkyl group having from 7 to 11 carbon atoms $R_2$ is methyl or ethyl; X is O or NH; and Y comprises a mono- or bicyclic heterocyclic group with optional substituents.

Rolipram, which was initially studied because of its activity as an anti-depressant, has been shown to selectively inhibit the PDE IV enzyme and this compound has since become a standard agent in the classification of PDE enzyme subtypes. There appears to be considerable therapeutic potential for PDE IV inhibitors. Early work focused on depression as a CNS therapeutic endpoint and on inflammation, and has subsequently been extended to include related diseases such as dementia and asthma. In-vitro, rolipram, RO20-1724 and other PDE IV inhibitors have been shown to inhibit (1) mediator synthesis/release in mast cells, basophils, monocytes and eosinophils; (2) respiratory burst, chemotaxis and degranulation in neutrophils and eosinophils; and (3) mitogen-dependent growth and differentiation in lymphocytes (The PDE IV Family Of Calcium-Phosphodiesterases Enzymes, John A. Lowe, III, et al., Drugs of the Future 1992, 17(9):799–807).

PDE IV is present in all the major inflammatory cells in asthma including eosinophils, neutrophils, T-lymphocytes, macrophages and endothelial cells. Its inhibition causes down regulation of inflammatory cell activation and relaxes smooth muscle cells in the trachea and bronchus. On the other hand, inhibition of PDE III, which is present in myocardium, causes an increase in both the force and rate of cardiac contractility. These are undesirable side effects for an anti-inflammatory agent. Theophylline, a non-selective PDE inhibitor, inhibits both PDE III and PDE IV, resulting in both desirable anti-asthmatic effects and undesirable cardiovascular stimulation. With this well-known distinction between PDE isozymes, the opportunity for concomitant anti-inflammation and bronchodilation without many of the side effects associated with theophylline therapy is apparent. The increased incidence of morbidity and mortality due to asthma in many Western countries over the last decade has focused the clinical emphasis on the inflammatory nature of this disease and the benefit of inhaled steroids. Development of an agent that possesses both bronchodilatory and antiinflammatory properties would be most advantageous.

It appears that selective PDE IV inhibitors should be more effective with fewer side effects than theophylline. Clinical support has been shown for this hypothesis. Furthermore, it would be desirable to provide PDE IV inhibitors which are more potent and selective than rolipram and therefore have a lower $IC_{50}$ so as to reduce the amount of the agent required to effect PDE IV inhibition.

In recent years, several different compounds have been suggested as possible therapeutic compositions which achieve the desired PDE IV inhibition without the side effects alluded to above. However, these efforts have been chiefly directed to developing non-specific derivatives of particular classes of compounds, i.e. rolipram analogs, benzoxazoles, adenines, thioxanthines, etc. These efforts, however, have resulted in a myriad of compounds having a wide range of PDE IV $IC_{50}$'s. Often, the general formulas disclosed yield several compounds which have poor levels of PDE IV inhibition and/or lack sufficient specificity. Consequently, these efforts often provide no assurance that any particular derivative within the formula will have the desired combination of high PDE IV inhibition and selectivity.

OBJECTS AND SUMMARY OF THE INVENTION

It is accordingly an object of the present invention to provide new compounds which are more effective selective PDE IV inhibitors than known prior art compounds.

It is another object of the present invention to provide new compounds which act as effective PDE IV inhibitors with lower PDE III inhibition.

It is another object of the present invention to provide methods for treating a patient requiring PDE IV inhibition.

It is another object of the present invention to provide new compounds for treating disease states associated with abnormally high physiological levels of inflammatory cytokines, including tumor necrosis factor.

It is another object of the present invention to provide a method of synthesizing the new compounds of this invention.

It is another object of the present invention to provide a method for treating a patient suffering from disease states such as asthma; allergies; inflammation; depression, dementia, including Alzheimer's disease, vascular dementia, and multi-in-farct dementia; a disease caused by Human Immunodeficiency Virus; and disease states associated with abnormally high physiological levels of inflammatory cytokines.

Other objects and advantages of the present invention will become apparent from the following detailed description thereof With the above and other objects in view, the present invention comprises compounds having the general formula (I):

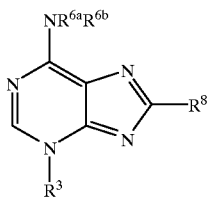

(I)

wherein
R³ is selected from the group consisting of
  hydrogen;
  $C_{1-10}$alkyl which is unbranched or branched and is optionally substituted with 1–3 substituents chosen from the group consisting of OH, $C_{1-10}$alkoxy, $C_{3-12}$cycloalkoxy, halogen, =NOH, =NOCONH₂, CO₂H, =O or benzyloxy, said benzyloxy optionally substituted with 1–3 substituents chosen from the group consisting of halogen, $C_{1-10}$alkyl, $C_{3-12}$cycloalkyl, $C_{1-10}$alkoxy, $C_{3-12}$cycloalkoxy;
  $C_{2-10}$alkenyl which is unbranched or branched and is optionally substituted with 1–3 substituents chosen from the group consisting of OH, $C_{3-12}$cycloalkyl, $C_{1-10}$alkoxy, $C_{3-12}$cycloalkoxy, halogen, =NOH, =NOCONH₂, CO₂H or =O;
  $C_{3-10}$cycloalkyl which is optionally substituted with 1–3 substituents chosen from the group consisting of OH, $C_{1-10}$alkyl, $C_{3-12}$cycloalkyl, $C_{1-10}$alkoxy, $C_{3-12}$cycloalkoxy, halogen, halo($C_{1-10}$)alkyl, =NOH, =NOCONH₂, CO₂H or =O;
  $C_{3-10}$cycloalkenyl which is optionally substituted with 1–3 substituents chosen from the group consisting of OH, $C_{1-10}$alkyl, $C_{3-12}$cycloalkyl, $C_{1-10}$alkoxy, $C_{3-12}$cycloalkoxy, halogen, halo($C_{1-10}$)alkyl, =NOH, =NOCONH₂, CO₂H or =O
  $C_{3-12}$cycloalkyl($C_{1-10}$)alkyl wherein the cycloalkyl portion is optionally substituted with 1–3 substituents chosen from the group consisting of OH, $C_{1-10}$alkyl, $C_{3-12}$cycloalkyl, $C_{1-10}$alkoxy, $C_{3-12}$cycloalkoxy, halogen, halo($C_{1-10}$)alkyl, =NOH, =NOCONH₂, CO₂H or =O;
  aryl which is optionally substituted with 1–3 substituents chosen from the group consisting of $C_{1-10}$alkyl, $C_{3-12}$cycloalkyl, OH, halogen, $C_{1-10}$alkoxy, $C_{3-12}$cycloalkoxy, $C_{1-10}$alkylamino, $C_{1-10}$dialkylamino, carbamyl, amido, $C_{1-10}$alkylamido, $C_{1-10}$dialkylamido, $C_{1-10}$acylamino, $C_{1-10}$alkylsulfonylamino, C=NOH, C=NOCONR₂, phenyl or benzyl
  ar($C_{1-4}$)alkyl wherein the aryl moiety is optionally substituted with 1–3 substituents chosen from the group consisting of carboxy, $C_{1-10}$alkylcarboxy, halogen, hydroxy, hydroxy($C_{1-10}$)alkoxy, nitro, trihalocarbon, benzyloxy, heterocyclyl, $C_{1-10}$cycloalkyl($C_{3-12}$)alkyloxy, ar($C_{1-10}$)alkyloxy, aryloxy, amino($C_{1-10}$)alkoxy, $C_{1-10}$alkylamino($C_{1-10}$)alkoxy, heteroaryloxy, heteroar($C_{1-10}$)alkyloxy, heterocyclyloxy, $C_{1-10}$alkyl, $C_{3-12}$cycloalkyl, $C_{1-10}$alkoxy or $C_{3-12}$cycloalkoxy said alkoxy and cycloalkoxy optionally substituted in one position at the alkyl moiety with hydroxy and said heterocyclyl is optionally substituted with $C_{1-10}$alkyl; and wherein the alkyl moiety of said ar ($C_{1-4}$)alkyl is optionally substituted with OH, halogen, $C_{1-10}$alkoxy and $C_{3-12}$cycloalkoxy said alkoxy and cycloalkoxy being optionally substituted in one position at the alkyl moiety with hydroxy;
  heterocyclyl which is optionally substituted on the carbons or nitrogens of the ring with 1–3 substituents chosen from the group consisting of $C_{1-10}$alkyl, OH, halogen, $C_{1-10}$alkoxy, $C_{3-12}$cycloalkoxy, NH₂, $C_{1-10}$alkylamino, $C_{1-10}$dialkylamino, carbamyl, amido, $C_{1-10}$alkylamido, $C_{1-10}$dialkylamido, $C_{1-10}$acylamino, $C_{1-10}$alkylsulfonylamino, C=NOH, C=NOCONH₂, phenyl or benzyl;
  heterocyclyl($C_1$–$C_4$)alkyl wherein said heterocyclyl moiety is optionally substituted on the carbons or nitrogens of the ring with 1–3 substituents chosen from the group consisting of $C_{1-10}$alkyl, $C_{3-12}$cycloalkyl, OH, halogen, $C_{1-10}$alkoxy, $C_{3-12}$cycloalkoxy, NH₂, $C_{1-10}$alkylamino, $C_{1-10}$dialkylamino, carbamyl, amido, $C_{1-10}$alkylamido, $C_{1-10}$dialkylamido, $C_{1-10}$acylamino, $C_{1-10}$alkylsulfonylamino, C=NOH, C=NOCONH₂, phenyl or benzyl, and wherein said alkyl moiety is optionally substituted with OH, $C_{1-10}$alkoxy, $C_{3-12}$cycloalkoxy, $C_{3-12}$cycloalkyl, halogen or halo($C_{1-10}$)alkyl;
  heteroaryl, which is optionally substituted with 1–3 substituents chosen from the group consisting of $C_{1-10}$alkyl, $C_{3-12}$cycloalkyl, halogen, nitro, CF₃, $C_{1-10}$alkoxy, $C_{3-12}$cycloalkoxy or oxo; and
  heteroaryl($C_{1-4}$)alkyl, wherein the heteroaryl moiety is optionally substituted with 1–3 substituents chosen from the group consisting of $C_{1-10}$alkyl, $C_{3-12}$cycloalkyl, halogen, nitro, trihalocarbon, $C_{1-10}$alkoxy or $C_{3-12}$cycloalkoxy;
R⁸ is selected from the group consisting of
  hydrogen;
  $C_{1-10}$alkyl which is unbranched or branched and is optionally substituted with 1–3 substituents chosen from the group consisting of OH, $C_{1-10}$alkoxy, $C_{3-12}$cycloalkoxy, halogen, =NOH, =NOCONH₂, CO₂H, =O or benzyloxy, said benzyloxy optionally substituted with 1–3 substituents chosen from the group consisting of halogen, $C_{1-10}$alkyl, $C_{3-12}$cycloalkyl, $C_{1-10}$alkoxy, $C_{3-12}$cycloalkoxy;
  $C_{2-10}$alkenyl which is unbranched or branched and is optionally substituted with 1–3 substituents chosen from the group consisting of OH, $C_{3-12}$cycloalkyl, $C_{1-10}$alkoxy, $C_{3-12}$cycloalkoxy, halogen, =NOH, =NOCONH₂, CO₂H or =O;
  $C_{3-10}$cycloalkyl which is optionally substituted with 1–3 substituents chosen from the group. consisting of OH, $C_{1-10}$alkyl, $C_{3-12}$cycloalkyl, $C_{1-10}$alkoxy, $C_{3-12}$cycloalkoxy, halogen, halo($C_{1-10}$)alkyl, =NOH, =NOCONH₂, CO₂H or =O;
  $C_{3-10}$cycloalkenyl which is optionally substituted with 1–3 substituents chosen from the group consisting of OH, $C_{1-10}$alkyl, $C_{3-12}$cycloalkyl, $C_{1-10}$alkoxy, $C_{3-12}$cycloalkoxy, halogen, halo($C_{1-10}$)alkyl, =NOH, =NOCONH₂, CO₂H or =O;
  $C_{3-12}$cycloalkyl($C_{1-10}$)alkyl wherein the cycloalkyl portion is optionally substituted with 1–3 substituents chosen from the group consisting of OH, $C_{1-10}$alkyl, $C_{3-12}$cycloalkyl, $C_{1-10}$alkoxy, $C_{3-12}$cycloalkoxy, halogen, halo($C_{1-10}$)alkyl, =NOH, =NOCONH₂, CO₂H or =O;
  aryl which is optionally substituted with 1–3 substituents chosen from the group consisting of $C_{1-10}$alkyl, $C_{3-12}$cycloalkyl, OH, halogen, $C_{1-10}$alkoxy, $C_{3-12}$cycloalkoxy, NH₂, $C_{1-10}$alkylamino, $C_{1-10}$dialkylamino, carbamyl, amido, $C_{1-10}$alkylamido, $C_{1-10}$dialkylamido, $C_{1-10}$acylamino, $C_{1-10}$alkylsulfonylamino, C=NOH, C=NOCONH$_2$, phenyl or benzyl;

ar($C_{1-4}$)alkyl wherein the aryl moiety is optionally substituted with 1–3 substituents chosen from the group consisting of carboxy, $C_{1-10}$alkylcarboxy, halogen, hydroxy, hydroxy($C_{1-10}$)alkoxy, nitro, trihalocarbon, benzyloxy, heterocyclyl, $C_{1-10}$cycloalkyl($C_{3-12}$)alkyloxy, ar($C_{1-10}$)alkyloxy, aryloxy, amino($C_{1-10}$)alkoxy, $C_{1-10}$alkylamino($C_{1-10}$)alkoxy, heteroaryloxy, heteroar($C_{1-10}$)alkyloxy, heterocyclyloxy, $C_{1-10}$alkyl, $C_{3-12}$cycloalkyl, $C_{1-10}$alkoxy or $C_{3-12}$cycloalkoxy said alkoxy and cycloalkoxy optionally substituted in one position at the alkyl moiety with hydroxy and said heterocyclyl is optionally substituted with $C_{1-10}$alkyl and wherein the alkyl moiety of said ar ($C_{1-4}$)alkyl is optionally substituted with OH, halogen, $C_{1-10}$alkoxy and $C_{3-12}$cycloalkoxy said alkoxy and cycloalkoxy being optionally substituted in one position at the alkyl moiety with hydroxy;

heterocyclyl which is optionally substituted on the carbons or nitrogens of the ring with 1–3 substituents chosen from the group consisting of $C_{1-10}$alkyl, OH, halogen, $C_{1-10}$alkoxy, $C_{3-12}$cycloalkoxy, NH$_2$, $C_{1-10}$alkylamino, $C_{1-10}$dialkylamino, carbamyl, amido, $C_{1-10}$alkylamido, $C_{1-10}$dialkylamido, $C_{1-10}$acylamino, $C_{1-10}$alkylsulfonylamino, C=NOH, C=NOCONH$_2$, phenyl or benzyl;

heterocyclyl($C_1$–$C_4$)alkyl wherein said heterocyclyl moiety is optionally substituted on the carbons or nitrogens of the ring with 1–3 substituents chosen from the group consisting of $C_{1-10}$alkyl, $C_{3-12}$cycloalkyl, OH, halogen, $C_{1-10}$alkoxy, $C_{3-12}$cycloalkoxy, NH$_2$, $C_{1-10}$alkylamino, $C_{1-10}$dialkylamino, carbamyl, amido, $C_{1-10}$alkylamido, $C_{1-10}$dialkylamido, $C_{1-10}$acylamino, $C_{1-10}$alkylsulfonylamino, C=NOH, C=NOCONH$_2$, phenyl or benzyl, and wherein said alkyl moiety is optionally substituted with OH, $C_{1-10}$alkoxy, $C_{3-12}$cycloalkoxy, $C_{3-12}$cycloalkyl, halogen or halo($C_{1-10}$)alkyl;

heteroaryl, which is optionally substituted with 1–3 substituents chosen from the group consisting of $C_{1-10}$alkyl, $C_{3-12}$cycloalkyl, halogen, nitro, CF$_3$, $C_{1-10}$alkoxy, $C_{3-12}$cycloalkoxy or oxo; and heteroaryl($C_{1-4}$)alkyl, wherein the heteroaryl moiety is optionally substituted with 1–3 substituents chosen from the group consisting of $C_{1-10}$alkyl, $C_{3-12}$cycloalkyl, halogen, nitro, trihalocarbon, $C_{1-10}$alkoxy or $C_{3-12}$cycloalkoxy;

$R^{6a}$ and $R^{6b}$ are independently selected from the group consisting of hydrogen;

$C_{1-10}$alkyl which is unbranched or branched and is optionally substituted with 1–3 substituents chosen from the group consisting of OH, $C_{1-10}$alkoxy, $C_{3-12}$cycloalkoxy, halogen, =NOH, =NOCONH$_2$, CO$_2$H, =O or benzyloxy, said benzyloxy optionally substituted with 1–3 substituents chosen from the group consisting of halogen, $C_{1-10}$alkyl, $C_{3-12}$cycloalkyl, $C_{1-10}$alkoxy, $C_{3-12}$cycloalkoxy, $C_{2-10}$alkenyl which is unbranched or branched and is optionally substituted with 1–3 substituents chosen from the group consisting of OH, $C_{3-12}$cycloalkoxy, $C_{1-10}$alkoxy, $C_{3-12}$cycloalkoxy, halogen, =NOH, =NOCONH$_2$, CO$_2$H or =O;

$C_{3-10}$cycloalkyl which is optionally substituted with 1–3 substituents chosen from the group consisting of OH, $C_{1-10}$alkyl, $C_{3-12}$cycloalkyl, $C_{1-10}$alkoxy, $C_{3-12}$cycloalkoxy, halogen, halo($C_{1-10}$)alkyl, =NOH, =NOCONH$_2$, CO$_2$H or =O;

$C_{3-10}$cycloalkenyl which is optionally substituted with 1–3 substituents chosen from the group consisting of OH, $C_{1-10}$alkyl, $C_{3-12}$cycloalkyl, $C_{1-10}$alkoxy, $C_{3-12}$cycloalkoxy, halogen, halo($C_{1-10}$)alkyl, =NOH, NOCONH$_2$, CO$_2$H or =O;

$C_{3-12}$cycloalkyl($C_{1-10}$)alkyl wherein the cycloalkyl portion is optionally substituted with 1–3 substituents chosen from the group consisting of OH, $C_{1-10}$alkyl, $C_{3-12}$cycloalkyl, $C_{1-10}$alkoxy, $C_{3-12}$cycloalkoxy, halogen, halo($C_{1-10}$)alkyl, =NOH, =NOCONH$_2$, CO$_2$H or =O;

aryl which is optionally substituted with 1–3 substituents chosen from the group consisting of $C_{1-10}$alkyl, $C_{3-12}$cycloalkyl, OH, halogen, $C_{1-10}$alkoxy, $C_{3-12}$cycloalkoxy, NH$_2$, $C_{1-10}$alkylamino, $C_{1-10}$dialkylamino, carbamyl, amido, $C_{1-10}$alkylamido, $C_{1-10}$dialkylamido, $C_{1-10}$acylamino, $C_{1-10}$alkylsulfonylamino, C=NOH, C=NOCONH$_2$, phenyl or benzyl;

ar($C_{1-4}$)alkyl wherein the aryl moiety is optionally substituted with 1–3 substituents chosen from the group consisting of carboxy, $C_{1-10}$alkylcarboxy, halogen, hydroxy, hydroxy($C_{1-10}$)alkoxy, nitro, trihalocarbon, benzyloxy, heterocyclyl, $C_{1-10}$cycloalkyl($C_{3-12}$)alkyloxy, ar($C_{1-10}$)alkyloxy, aryloxy, amino($C_{1-10}$)alkoxy, $C_{1-10}$alkylamino($C_{1-10}$)alkoxy, heteroaryloxy, heteroar($C_{1-10}$)alkyloxy, heterocyclyloxy, $C_{1-10}$alkyl, $C_{3-12}$cycloalkyl, $C_{1-10}$alkoxy or $C_{3-12}$cycloalkoxy said alkoxy and cycloalkoxy optionally substituted in one position at the alkyl moiety with hydroxy and said heterocyclyl is optionally substituted with $C_{1-10}$alkyl; and wherein the alkyl moiety of said ar ($C_{1-4}$)alkyl is optionally substituted with OH, halogen, $C_{1-10}$alkoxy and $C_{3-12}$cycloalkoxy said alkoxy and cycloalkoxy being optionally substituted in one position at the alkyl moiety with hydroxy;

heterocyclyl which is optionally substituted on the carbons or nitrogens of the ring with 1–3 substituents chosen from the group consisting of $C_{1-10}$alkyl, OH, halogen, $C_{1-10}$alkoxy, $C_{3-12}$cycloalkoxy, NH$_2$, $C_{1-10}$alkylamino, $C_{1-10}$dialkylamino, carbamyl, amido, $C_{1-10}$alkylamido, $C_{1-10}$dialkylamido, $C_{1-10}$acylamino, $C_{1-10}$alkylsulfonylamino, C=NOH, C=NOCONH$_2$, phenyl or benzyl;

heterocyclyl($C_1$–$C_4$)alkyl wherein said heterocyclyl moiety is optionally substituted on the carbons or nitrogens of the ring with 1–3 substituents chosen from the group consisting of $C_{1-10}$alkyl, $C_{3-12}$cycloalkyl, OH, halogen, $C_{1-10}$alkoxy, $C_{3-12}$cycloalkoxy, NH$_2$, $C_{1-10}$alkylamino, $C_{1-10}$dialkylamino, carbamyl, amido, $C_{1-10}$alkylamido, $C_{1-10}$dialkylamido, $C_{1-10}$acylamino, $C_{1-10}$alkylsulfonylamino, C=NOH, C=NOCONH$_2$, phenyl or benzyl and wherein said alkyl moiety is optionally substituted with OH, $C_{1-10}$alkoxy, $C_{3-12}$cycloalkoxy, $C_{3-12}$cycloalkyl, halogen or halo($C_{1-10}$)alkyl;

heteroaryl, which is optionally substituted with 1–3 substituents chosen from the group consisting of $C_{1-10}$alkyl, $C_{3-12}$cycloalkyl, halogen, nitro, CF$_3$, $C_{1-10}$alkoxy, $C_{3-12}$cycloalkoxy or oxo; and heteroaryl($C_{1-4}$)alkyl, wherein the heteroaryl moiety is optionally substituted with 1–3 substituents chosen from the group consisting of $C_{1-10}$alkyl, $C_{3-12}$cycloalkyl, halogen, nitro, trihalocarbon, $C_{1-10}$alkoxy or $C_{3-12}$cycloalkoxy;

provided that when $R^3$ is an unsubstituted benzyl group, $R^{6a}$ is a methyl or isopropyl group and $R^{6b}$ is a hydrogen atom;

when $R^3$, $R^{6a}$ and $R^{6b}$ are methyl groups, then $R^8$ is other than a hydrogen atom;

when $R^8$ is methyl or a hydrogen atom, $R^3$ is nether methyl or hydrogen;

when $R^8$ is phenyl, $R^3$ is not methyl;

when $R^8$ is pyridyl, $R^3$ is not a hydrogen atom; and when $R^{6a}$ and $R^{6b}$ are both hydrogen, then $R^8$ is not hydrogen or alkylC(O)OH;

and pharmaceutically acceptable salts thereof.

In certain preferred embodiments, $R^3$ is an ar($C_{1-4}$)alkyl, wherein the aryl moiety is optionally substituted at 1–3 positions with halogen, nitro, alkoxy, cycloalkoxy or $CF_3$, and wherein the alkyl moiety is optionally substituted with OH, halogen, alkoxy and cycloalkoxy. The aralkyl may be a benzyl, which may be optionally substituted as described above. In other preferred embodiments, the aralkyl is a benzyl substituted with alkoxy and cycloalkoxy.

In other preferred embodiments, $R^{6a}$ is a hydrogen. In other preferred embodiments, $R^{6a}$ is hydrogen and $R^{6b}$ is selected from the group consisting of $C_{1-10}$alkyl, preferably $C_{1-8}$alkyl, which is unbranched or branched and is optionally substituted with OH, alkoxy, cycloalkoxy, halogen, =NOH, =NOCONH$_2$, CO$_2$H or =O; $C_{2-10}$alkenyl which is unbranched or branched and is optionally substituted with OH, alkoxy, cycloalkoxy, halogen, =NOH, =NOCONH$_2$, CO$_2$H or =O; $C_{3-10}$cycloalkyl, preferably $C_{3-8}$cycloalkyl, which is optionally substituted with OH, alkoxy, cycloalkoxy, halogen, haloalkyl, =NOH, =NOCONH$_2$, CO$_2$H or =O; $C_{3-10}$cycloalkenyl which is optionally substituted with OH, alkoxy, cycloalkoxy, halogen, haloalkyl, =NOH, =NOCONH$_2$, CO$_2$H or =O; aryl which is optionally substituted with $C_{1-8}$alkyl, OH, halogen, alkoxy, cycloalkoxy, NH$_2$, alkylamino, dialkylamino, carbamyl, amido, $C_{1-8}$alkylamido, $C_{1-3}$dialkylamido, $C_{1-8}$acylamino, $C_{1-8}$alkylsulfonylamino, C=NOH, C=NOCONH$_2$, phenyl or benzyl; aralkyl $C_{1-4}$ wherein the aryl moiety is optionally substituted with halogen, nitro, alkoxy, cycloalkoxy or $CF_3$, and wherein the alkyl moiety is optionally substituted with OH, halogen, alkoxy and cycloalkoxy; heterocyclyl which is optionally substituted on the carbons or nitrogens of the ring with $C_{1-8}$alkyl, OH, halogen, alkoxy, cycloalkoxy, NH2, alkylamino, dialkylamino, carbamyl, amido, $C_{1-8}$alkylamido, $C_{1-3}$dialkylamido, $C_{1-8}$acylamino, $C_{1-8}$alkylsulfonylamino, C=NOH, C=NOCONH$_2$, phenyl or benzyl; and heterocyclylalkyl ($C_1$–$C_4$) wherein said heterocyclyl moiety is optionally substituted on the carbons or nitrogens of the ring with $C_{1-8}$alkyl, OH, halogen, alkoxy, cycloalkoxy, NH$_2$, alkylamino, dialkylamino, carbamyl, amido, $C_{1-8}$alkylamido, $C_{1-3}$dialkylamido, $C_{1-8}$acylamino, $C_{1-8}$alkylsulfonylamino, C=NOH, C=NOCONH$_2$, phenyl or benzyl, and wherein said alkyl moiety is optionally substituted with OH, alkoxy, cycloalkoxy, halogen or haloalkyl; heteroaryl, which is optionally substituted with $C_{1-4}$alkyl, halogen, nitro, $CF_3$, alkoxy or cycloalkoxy; and heteroaryl($C_{1-4}$)alkyl, wherein the heteroaryl moiety is optionally substituted with $C_{1-4}$alkyl, halogen, nitro, $CF_3$, alkoxy or cycloalkoxy;

In other preferred embodiments, $R^{6a}$ is hydrogen and $R^{6b}$ is selected from the group consisting of $C_{1-10}$alkyl, preferably $C_{1-8}$alkyl, which is unbranched or branched and is optionally substituted with OH, alkoxy, cycloalkoxy, halogen, =NOH, =NOCONH$_2$, CO$_2$H or =O; $C_{2-10}$alkenyl which is unbranched or branched and is optionally substituted with OH, alkoxy, cycloalkoxy, halogen, =NOH, =NOCONH$_2$, CO$_2$H or =O; $C_{3-10}$cycloalkyl, preferably $C_{3-8}$cycloalkyl, which is optionally substituted with OH, alkoxy, cycloalkoxy, halogen, haloalkyl, =NOH, =NOCONH$_2$, CO$_2$H or =O; and $C_{3-10}$cycloalkenyl, which is optionally substituted with OH, alkoxy, cycloalkoxy, halogen, haloalkyl, =NOH, =NOCONH$_2$, CO$_2$H or =O. In particular, $R^{6a}$ may be a hydrogen and $R^{6b}$ may be a $C_{1-8}$alkyl which is unbranched or branched and is optionally substituted with OH, alkoxy, cycloalkoxy, halogen, =NOH, =NOCONH$_2$, CO$_2$H or =O. In other preferred embodiments of the invention, $R^{6b}$, N, and $R^{6a}$ form a 3 to 8 membered ring containing at least one carbon atom, from one to three nitrogen atoms, from zero to two oxygen atoms, and from zero to two sulfur atoms, optionally substituted with hydroxy, alkoxy, cycloalkoxy, $C_{1-4}$alkyl, CO$_2$H, CONH$_2$, =NOH, =NOCONH$_2$, =O.

In other preferred embodiments, $R^8$ is selected from the group consisting of $C_{1-10}$alkyl, preferably $C_{1-8}$alkyl, which is unbranched or branched and is optionally substituted with OH, alkoxy, cycloalkoxy, halogen, =NOH, =NOCONH$_2$, CO$_2$H or =O; $C_{2-10}$alkenyl, which is unbranched or branched and is optionally substituted with OH, alkoxy, cycloalkoxy, halogen, =NOH, =NOCONH$_2$, CO$_2$H or =O; $C_{3-10}$cycloalkyl, preferably $C_{3-8}$cycloalkyl, which is optionally substituted with OH, alkoxy, cycloalkoxy, halogen, haloalkyl, =NOH, =NOCONH$_2$, CO$_2$H or =O; $C_{3-10}$cycloalkenyl, which is optionally substituted with OH, alkoxy, cycloalkoxy, halogen, haloalkyl, =NOH, =NOCONH$_2$, CO$_2$H or =O; $C_{4-8}$cycloalkylalkyl wherein the cycloalkyl portion is optionally substituted with OH, alkoxy, cycloalkoxy, halogen, haloalkyl, =NOH, =NOCONH$_2$, CO$_2$H or =O; aryl which is optionally substituted with $C_{1-8}$alkyl, OH, halogen, alkoxy, cycloalkoxy, NH$_2$, alkylamino, dialkylamino, carbamyl, amido, $C_{1-8}$alkylamido, $C_{1-3}$dialkylamido, $C_{1-8}$acylamino, $C_{1-8}$alkylsulfonylamino, C=NOH, C=NOCONH$_2$, phenyl or benzyl; aralkyl $C_{1-4}$ wherein the aryl moiety is optionally substituted with hydroxy, halogen, nitro, alkoxy, cycloalkoxy or $CF_3$, and wherein the alkyl moiety is optionally substituted with OH, halogen, alkoxy and cycloalkoxy; heterocyclyl which is optionally substituted on the carbons or nitrogens of the ring with $C_{1-8}$alkyl OH, halogen, alkoxy, cycloalkoxy, NH$_2$, alkylamino, dialkylamino, carbamyl, amido, $C_{1-8}$alkylamido, $C_{1-3}$dialkylamido, $C_{1-8}$acylamino, $C_{1-8}$alkylsulfonylamino, C=NOH, C=NOCONH$_2$, phenyl or benzyl; heterocyclylalkyl ($C_1$–$C_4$) wherein said heterocyclyl moiety is optionally substituted on the carbons or nitrogens of the ring with $C_{1-8}$alkyl, OH, halogen, alkoxy, cycloalkoxy, NH$_2$, alkylamino, dialkylamino, carbamyl, amido, $C_{1-8}$alkylamido, $C_{1-3}$dialkylamido, $C_{1-8}$acylamino, $C_{1-8}$alkylsulfonylamino, C=NOH, C=NOCONH$_2$, phenyl or benzyl, and wherein said alkyl moiety is optionally substituted with OH, alkoxy, cycloalkoxy, halogen or haloalkyl; heteroaryl, which is optionally substituted with $C_{1-4}$alkyl, halogen, nitro, $CF_3$, alkoxy or cycloalkoxy; and heteroaryl($C_{1-4}$)alkyl, wherein the heteroaryl moiety is optionally substituted with $C_{1-4}$alkyl, halogen, nitro, $CF_3$, alkoxy or cycloalkoxy.

In other preferred embodiments, $R^8$ is selected from the group consisting of $C_{1-8}$alkyl which is unbranched or branched and is optionally substituted with OH, alkoxy, cycloalkoxy, halogen, =NOH, =NOCONF$_2$, CO$_2$H or =O; and $C_{3-8}$cycloalkyl which is optionally substituted with OH, alkoxy, cycloalkoxy, halogen, haloalkyl, =NOH, =NOCONH$_2$, CO$_2$H or =O.

In other preferred embodiments of the invention $R^3$, $R^{6a}$, $R^{6b}$ and $R^8$ are selected from the group consisting of A and B, wherein A is selected from the group consisting of
hydrogen;
$C_{1-10}$alkyl which is unbranched or branched and is optionally substituted with 1–3 substituents chosen from the group consisting of OH, $C_{1-10}$alkoxy, $C_{3-12}$cycloalkoxy, halogen, =NOH, =NOCONH$_2$, CO$_2$H, =O and benzyloxy; said benzyloxy optionally substituted with 1–3 substituents chosen from the group consisting of halogen, $C_{1-10}$alkyl, $C_{3-12}$cycloalkyl, $C_{1-10}$alkoxy and $C_{3-12}$cycloalkoxy;
$C_{2-10}$alkenyl which is unbranched or branched and is optionally substituted with 1–3 substituents chosen from the group consisting of OH, $C_{3-12}$cycloalkyl, $C_{1-10}$alkoxy, $C_{3-12}$cycloalkoxy, halogen, =NOH, =NOCONH$_2$, CO$_2$H and =O;
$C_{3-10}$cycloalkyl which is optionally substituted with 1–3 substituents chosen from the group consisting of OH, $C_{1-10}$alkyl, $C_{3-12}$cycloalkyl, $C_{1-10}$alkoxy, $C_{3-12}$cycloalkoxy, halogen, halo($C_{1-10}$)alkyl, =NOH, =NOCONH$_2$, CO$_2$H and =O;
$C_{3-10}$cycloalkenyl which is optionally substituted with 1–3 substituents chosen from the group consisting of OH, $C_{1-10}$alkyl, $C_{3-12}$cycloalkyl, $C_{1-10}$alkoxy, $C_{3-12}$cycloalkoxy, halogen, halo($C_{1-10}$)alkyl, =NOH, =NOCONH$_2$, CO$_2$H and =O;
$C_{3-12}$cycloalkyl($C_{1-10}$)alkyl wherein the cycloalkyl portion is optionally substituted with 1–3 substituents chosen from the group consisting of OH, $C_{1-10}$alkyl, $C_{3-12}$cycloalkyl, $C_{1-10}$alkoxy, $C_{3-12}$cycloalkoxy, halogen, halo($C_{1-10}$)alkyl, =NOH, =NOCONH$_2$, CO$_2$H and =O,
aryl which is optionally substituted with 1–3 substituents chosen from the group consisting of $C_{1-10}$alkyl, $C_{3-12}$cycloalkyl, OH, halogen, $C_{1-10}$alkoxy, $C_{3-12}$cycloalkoxy, NH$_2$, $C_{1-10}$alkylamino, $C_{1-10}$dialkylamino, carbamyl, amido, $C_{1-10}$alkylamido, $C_{1-10}$dialkylamido, $C_{1-10}$acylamino, $C_{1-10}$alkylsulfonylamino, C=NOH, C=NOCONH$_2$, phenyl and benzyl;
ar($C_{1-4}$)alkyl wherein the aryl moiety is optionally substituted with 1–3 substituents chosen from the group consisting of carboxy, $C_{1-10}$alkylcarboxy, halogen, hydroxy, hydroxy($C_{1-10}$)alkoxy, nitro, trihalocarbon, benzyloxy, heterocyclyl, $C_{1-10}$cycloalkyl($C_{3-12}$)alkyloxy, ar($C_{1-10}$)alkyloxy, aryloxy, amino($C_{1-10}$)alkoxy, $C_{1-10}$alkylamino($C_{1-10}$)alkoxy, heteroaryloxy, heteroar($C_{1-10}$)alkyloxy, heterocyclyloxy, $C_{1-10}$alkyl, $C_{3-12}$cycloalkyl, $C_{1-10}$alkoxy and $C_{3-12}$cycloalkoxy; said alkoxy and cycloalkoxy optionally substituted in one position at the alkyl moiety with hydroxy and said heterocyclyl is optionally substituted with $C_{1-10}$alkyl; and wherein the alkyl moiety of said ar ($C_{1-4}$)alkyl is optionally substituted with OH, halogen, $C_{1-10}$alkoxy or $C_{3-12}$cycloalkoxy said alkoxy and cycloalkoxy being optionally substituted in one position at the alkyl moiety with hydroxy;
heterocyclyl which is optionally substituted on the carbons or nitrogens of the ring with 1–3 substituents chosen from the group consisting of $C_{1-10}$alkyl, OH, halogen, $C_{1-10}$alkoxy, $C_{3-12}$cycloalkoxy, NH$_2$, $C_{1-10}$alkylamino, $C_{1-10}$dialkylamino, carbamyl, amido, $C_{1-10}$alkylamido, $C_{1-10}$dialkylamido, $C_{1-10}$acylamino, $C_{1-10}$alkylsulfonylamino, C=NOH, C=NOCONH$_2$, phenyl and benzyl;
heterocyclyl($C_1$–$C_4$)alkyl wherein said heterocyclyl moiety is optionally substituted on the carbons or nitrogens of the ring with 1–3 substituents chosen from the group consisting of $C_{1-10}$alkyl, $C_{3-12}$cycloalkyl, OH, halogen, $C_{1-10}$alkoxy, $C_{3-12}$cycloalkoxy, NH$_2$, $C_{1-10}$alkylamino, $C_{1-10}$dialkylamino, carbamyl, amido, $C_{1-10}$alkylamido, $C_{1-10}$dialkylamido, $C_{1-10}$acylamino $C_{1-10}$alkylsulfonylamino, C=NOH, C=NOCONH$_2$, phenyl and benzyl, and wherein said alkyl moiety is optionally substituted with OH, $C_{1-10}$alkoxy, $C_{3-12}$cycloalkoxy, $C_{3-12}$cycloalkyl, halogen and halo($C_{1-10}$)alkyl;
heteroaryl, which is optionally substituted with 1–3 substituents chosen from the group consisting of $C_{1-10}$alkyl, $C_{3-12}$cycloalkyl, halogen, nitro, CF$_3$, $C_{1-10}$alkoxy, $C_{3-12}$cycloalkoxy and oxo; and
heteroaryl($C_{1-4}$)alkyl, wherein the heteroaryl moiety is optionally substituted with 1–3 substituents chosen from the group consisting of $C_{1-10}$alkyl, $C_{3-12}$cycloalkyl, halogen, nitro, trihalocarbon, $C_{1-10}$alkoxy and $C_{3-12}$cycloalkoxy; and B is selected from the group consisting of
$C_{1-10}$alkyl which is unbranched or branched and is substituted with 1–3 substituents chosen from the group consisting of benzyloxy, methylenedioxybenzyloxy, methylenedioxyphenyl, pyridylmethoxy, thienylmethoxy and alkylamino; said substituents optionally substituted with 1–3 substituents chosen from the group consisting of halogen, $C_{1-10}$alkyl, $C_{3-12}$cycloalkyl, $C_{1-10}$alkoxy, $C_{3-12}$cycloalkoxy and oxo; said substituted $C_{1-10}$alkyl further optionally substituted with 1–3 substituents chosen from the group consisting of OH, $C_{1-10}$alkoxy, $C_{3-12}$cycloalkoxy, halogen, =NOH, =NOCONH$_2$, CO$_2$H, and =O
$C_{2-10}$alkenyl which is unbranched or branched and is optionally substituted with 1–3 substituents chosen from the group consisting of OH, $C_{3-12}$cycloalkyl, $C_{1-10}$alkoxy, $C_{3-12}$cycloalkoxy, halogen, =NOH, =NOCONH$_2$, CO$_2$H and =O;
$C_{3-10}$cycloalkyl which is substituted with 1–3 substituents chosen from the group consisting of $C_{1-10}$alkyl and $C_{3-12}$cycloalkyl; said substituted $C_{3-10}$cycloalkyl further optionally substituted with 1–3 substituents chosen from the group consisting of OH, $C_{1-10}$alkoxy, $C_{3-12}$cycloalkoxy, halogen, halo($C_{1-10}$)alkyl, =NOH, =NOCONH$_2$, CO$_2$H and =O;
$C_{3-10}$cycloalkenyl which is optionally substituted with 1–3 substituents chosen from the group consisting of OH, $C_{1-10}$alkyl, $C_{3-12}$cycloalkyl, $C_{1-10}$alkoxy, $C_{3-12}$cycloalkoxy, halogen, halo($C_{1-10}$)alkyl, =NOH, =NOCONH$_2$, CO$_2$H and =O;
$C_{3-12}$cycloalkyl($C_{1-10}$)alkyl wherein the cycloalkyl portion is substituted with 1–3 substituents chosen from the group consisting of $C_{1-10}$alkyl, $C_{3-12}$cycloalkyl, halogen, halo($C_{1-10}$)alkyl, and =O said substituted $C_{3-12}$cycloalkyl($C_{1-10}$)alkyl further optionally substituted with 1–3 substituents chosen from the group consisting of OH, $C_{1-10}$alkoxy, $C_{3-12}$cycloalkoxy, =NOH, =NOCONH$_2$, and CO$_2$H;
aryl which is substituted with 1–3 substituents chosen from the group consisting of carbamyl, amido, $C_{1-10}$alkylamido, $C_{1-10}$dialkylamido, $C_{1-10}$acylamino and $C_{1-10}$alkylsulfonylamino; said substituted aryl further optionally substituted with 1–3 substituents chosen from the group consisting of $C_{1-10}$alkyl, $C_{3-12}$cycloalkyl, OH, halogen, $C_{1-10}$alkoxy, $C_{3-12}$cycloalkoxy, $NH_2$, $C_{1-10}$alkylamino, $C_{1-10}$dialkylamino, C=NOH, C=NOCONH$_2$, phenyl and benzyl;

ar($C_{1-4}$)alkyl wherein the aryl moiety is substituted with 1–3 substituents chosen from the group consisting of carboxy, $C_{1-10}$alkylcarboxy, hydroxy($C_{1-10}$)alkoxy, nitro, benzyloxy, heterocyclyl, $C_{1-10}$cycloalkyl($C_{3-12}$)alkyloxy, ar($C_{1-10}$)alkyloxy, aryloxy, amino($C_{1-10}$)alkoxy, $C_{1-10}$alkylamino($C_{1-10}$)alkoxy, heteroaryloxy, heteroar($C_{1-10}$)alkyloxy, heterocyclyloxy, $C_{1-10}$alkoxy and $C_{3-12}$cycloalkoxy; said alkoxy and cycloalkoxy substituted in one position at the alkyl moiety with hydroxy and said heterocyclyl is optionally substituted with $C_{1-10}$alkyl and wherein the alkyl moiety of said ar ($C_{1-4}$)alkyl is optionally substituted with OH, halogen, $C_{1-10}$alkoxy and $C_{3-12}$cycloalkoxy said alkoxy and cycloalkoxy being optionally substituted in one position at the alkyl moiety with hydroxy; and said substituted ar($C_{1-4}$)alkyl further optionally substituted with 1–3 substituents chosen from the group consisting of halogen, hydroxy, trihalocarbon, $C_{1-10}$alkyl, $C_{3-12}$cycloalkyl, $C_{1-10}$alkoxy and $C_{3-12}$cycloalkoxy heterocyclyl which is substituted on the carbons or nitrogens of the ring with 1–3 substituents chosen from the group consisting of carbamyl, $C_{1-10}$acylamino and $C_{1-10}$alkylsulfonylamino; said substituted heterocyclyl further optionally substituted with 1–3 substituents chosen from the group consisting of $C_{1-10}$alkyl, OH, halogen, $C_{1-10}$alkoxy, $C_{3-12}$cycloalkoxy, $NH_2$, $C_{1-10}$alkylamino, $C_{1-10}$dialkylamino, amido, $C_{1-10}$alkylamido, $C_{1-10}$dialkylamido, C=NOH, C=NOCONHR, phenyl and benzyl;

heterocyclyl($C_1$–$C_4$)alkyl wherein said heterocyclyl moiety is substituted on the carbons or nitrogens of the ring with 1–3 substituents chosen from the group consisting of $C_{1-10}$acylamino, $C_{1-10}$alkylsulfonylamino, and $C_{1-10}$alkyl, said $C_{1-10}$alkyl substituted with OH, $C_{1-10}$alkoxy, $C_{3-12}$cycloalkoxy, $C_{3-12}$cycloalkyl, halogen or halo($C_{1-10}$)alkyl; said substituted heterocyclyl($C_1$–$C_4$)alkyl further optionally substituted with 1–3 substituents chosen from the group consisting of $C_{1-10}$alkyl, $C_{3-12}$cycloalkyl, OH, halogen, $C_{1-10}$alkoxy, $C_{3-12}$cycloalkoxy, $NH_2$, $C_{1-10}$alkylamino, $C_{1-10}$dialkylamino, amido, $C_{1-10}$alkylamido and $C_{1-10}$dialkylamido, heteroaryl, which is substituted with oxo; said substituted heteroaryl further optionally substituted with 1–3 substituents chosen from the group consisting of $C_{1-10}$alkyl, $C_{3-12}$cycloalkyl, halogen, nitro, $CF_3$, $C_{1-10}$alkoxy and $C_{3-12}$cycloalkoxy; and heteroaryl($C_{1-4}$)alkyl, wherein the heteroaryl moiety is substituted with nitro; said heteroaryl($C_{1-4}$)alkyl further optionally substituted with 1–3 substituents chosen from the group consisting of $C_{1-10}$alkyl, $C_{3-12}$cycloalkyl, halogen, trihalocarbon, $C_{1-10}$alkoxy and $C_{3-12}$cycloalkoxy; and provided that at least one of $R^3$, $R^{6a}$, $R^{6b}$ and $R^8$ is B.

In certain preferred embodiments, $R^3$ is A and is ar($C_{1-4}$)alkyl, preferably benzyl, wherein the aryl moiety is option- ally substituted with 1–3 substituents chosen from the group consisting of halogen, nitro, $C_{1-10}$alkoxy, $C_{3-12}$cycloalkoxy or $CF_3$, and wherein the alkyl moiety is optionally substituted with 1–3 substituents chosen from the group consisting of OH, halogen, $C_{1-10}$alkoxy and $C_{3-12}$cycloalkoxy. When the ar($C_{1-4}$)alkyl is benzyl, said aryl moiety is preferably substituted with with cyclopentyloxy and methoxy.

In certain preferred embodiments, $R^{6a}$ is A and is hydrogen.

In certain preferred embodiments $R^{6b}$ is A and is selected from the group consisting of
  hydrogen;
  $C_{1-8}$alkyl which is unbranched or branched and is optionally substituted with OH, alkoxy, cycloalkoxy, halogen, =NOH, =NOCONH$_2$, $CO_2H$ or =O; and
  $C_{3-8}$cycloalkyl which is optionally substituted with OH, alkoxy, cycloalkoxy, halogen, haloalkyl, =NOH, =NOCONH$_2$, $CO_2H$ or =O.

In certain preferred embodiments $R^8$ is B and is selected from the group consisting of
  $C_{1-10}$alkyl which is unbranched or branched and is substituted with 1–3 substituents chosen from the group consisting of benzyloxy, methylenedioxybenzyloxy, methylenedioxyphenyl, pyridylmethoxy, thienylmethoxy and alkylamino, said substituents optionally substituted with 1–3 substituents chosen from the group consisting of halogen, $C_{1-10}$alkyl, $C_{3-12}$cycloalkyl, $C_{1-10}$alkoxy, $C_{3-12}$cycloalkoxy and oxo.

In certain preferred embodiments $R^3$ is A and is ar($C_{1-4}$) alkyl, preferably benzyl, wherein the aryl moiety is optionally substituted with 1–3 substituents chosen from the group consisting of halogen, nitro, $C_{1-10}$alkoxy, $C_{3-12}$cycloalkoxy or $CF_3$, and wherein the alkyl moiety is optionally substituted with 1–3 substituents chosen from the group consisting of OH, halogen, $C_{1-10}$alkoxy and $C_{3-12}$cycloalkoxy and when the ar($C_{1-4}$)alkyl is benzyl, said aryl moiety is preferably substituted with with cyclopentyloxy and methoxy; $R^{6a}$ is A and is hydrogen; $R^{6b}$ is A and is selected from the group consisting of hydrogen, $C_{1-8}$alkyl which is unbranched or branched and is optionally substituted with OH, alkoxy, cycloalkoxy, halogen, =NOH, =NOCONH$_2$, $CO_2H$ or =O; and $C_{3-8}$cycloalkyl which is optionally substituted with OH, alkoxy, cycloalkoxy, halogen, haloalkyl, =NOH, =NOCONH$_2$, $CO_2H$ or =O; and $R^8$ is B and is selected from the group consisting of $C_{1-10}$alkyl which is unbranched or branched and is substituted with 1–3 substituents chosen from the group consisting of benzyloxy, methylenedioxybenzyloxy, methylenedioxyphenyl, pyridylmethoxy, thienylmethoxy and alkylamino, said substituents optionally substituted with 1–3 substituents chosen from the group consisting of halogen, $C_{1-10}$alkyl, $C_{3-12}$cycloalkyl, $C_{1-10}$alkoxy, $C_{3-12}$cycloalkoxy and oxo.

Certain preferred adenine compounds according to the invention include: 6-ethylamino-3-hexyl-3H-purine; 3-hexyl-6-methylamino-3H-purine; 8-cyclopropyl-6-ethylamino-3-(3-methylbutyl)-3H-purine; 8-cyclopropyl-3-ethyl-6-propylamino-3H-purine; 8-cyclopropyl-3-ethyl-6-methylamino-3H-purine; 3-butyl-6-ethylamino-3H-purine; 3-butyl-8-cyclopropyl-6-ethylamino-3H-purine; 6-ethylamino-3-propyl-3H-purine; 8-cyclopropyl-6-ethylamino-3-propyl-3H-purine; 8-cyclopropyl-3-cyclopropylmethyl-6-ethylamino-3H-purine; 3-benzyl-6-ethylamino-3H-purine; 8-cyclopropyl-6-cyclopropylamino-3-propyl-3H-purine; 3-(2-methylbutyl)-6-(2-(piperazine-1-yl)ethylamino)-3H-purine; 3-cyclohexylmethyl-6-ethylamino-3H-purine; 3-benzyl-6-ethylamino-8-(1- methylethyl)-3H-purine; 3-cyclohexylmethyl-8-cyclopropyl-6-ethylamino-3H-purine; 3-cyclopropylmethyl-8-isopropyl-6-ethylamino-3H-purine; 3-ethyl-8-isopropyl-6-benzylamino-3H-purine; 3-ethyl-8-isopropyl-6-ethylamino-3H-purine; 3-ethyl-8-cyclopentyl-6-benzylamino-3H-purine; 3-ethyl-8-cyclopentyl-6-ethylamino-3H-purine; 3-(4-chlorobenzyl)-6-ethylamino-3H-purine; 3-(2-chlorobenzyl)-6-ethylamino-3H-purine; 3-(2-chlorobenzyl)-6-ethylamino-8-isopropyl-3H-purine; 6-benzylamino-8-cyclopropyl-3-propyl-3H-purine; 8-cyclopropyl-6-hexylamino-3-propyl-3H-purine; 8-cyclopropyl-3-propyl-6-(4-pyridylmethylamino)-3H-purine; 6-cyclopentylamino-8-cylopropyl-3-propyl-3H-purine; 6-butylamino-8-cyclopropyl-3-propyl-3H-purine; 8-cyclopropyl-6-(2-hydroxyethylamino)-3-propyl-3H-purine; 6-(3-cyclopentyloxy-4-methoxybenzylamino)-8-cyclopropyl-3-propyl-3H-purine; 6-amino-8-cyclopropyl-3-propyl-3H-purine; 3-ethyl-6-cyclopentylamino-8-isopropyl-3H-purine; 6-cyclohexylamino-8-isopropyl-3-propyl-3H-purine; 6-cyclopentylamino-8-isopropyl-3-propyl-3H-purine; 3-ethyl-6-cyclopentylamino-8-cyclopropyl-3H-purine; 3-(4-chlorobenzyl)-6-cyclopentylamino-8-cyclopropyl-3H-purine; 6-cyclopentylamino-3-(3-cyclopentyloxy-4-methoxybenzyl)-8-isopropyl-3H-purine; 3-(2-chlorobenzyl)-6-cyclopentylamino-8-isopropyl-3H-purine; 8-cyclopropyl-6-diethylamino-3-propyl-3H-purine hydrochloride; 8-cyclopropyl-6-(3-pentylamino)-3-propyl-3H-purine hydrochloride; 6-ethylamino-8-isopropyl-3-(4-pyridylmethyl)-3H-purine; 3-ethyl-8-isopropyl-6-ethylamino-3H-purine; 3-ethyl-8-cyclopentyl-6-benzylamino-3H-purine; 3-ethyl-8-cyclopentyl-6-ethylamino-3H-purine; 3-cylcohexylmethyl-6-ethylamino-3H-purine; 3-cyclohexylmethyl-8-cyclopropyl-6-ethylamino-3H-purine; 8-cyclopropyl-6-ethylamino-3-(3-methylbutyl)-3H-purine; 8-cyclopropyl-3-ethyl-6-propylamino-3H-purine; 8-cyclopropyl-3-cyclopropylmethyl-6-ethylamino-3H-purine; 3-hexyl-6-methylamino-3H-purine; 3-cyclopropylmethyl-8-isopropyl-6-ethylamino-3H-purine; 3-ethyl-8-isopropyl-6-benzylamino-3H-purine; 3-butyl-6-ethylamino-3H-purine; 3-butyl-8-cyclopropyl-6-ethylamino-3H-purine; 8-cyclopropyl-6-ethylamino-3-propyl-3H-purine; 8-cyclopropyl-6-cyclopropylamino-3-propyl-3H-purine; 3-(3-cyclopentyloxy-4-methoxybenzyl)-6-ethylamino-8-isopropyl-3H-purine; and 3-ethyl-6-ethylamino-8-(3-cyclopentyloxy-4-methoxy-benzyl)-3H-purine.

Other preferred adenine compounds according to the invention include: 3,8-diethyl-6-morpholino-3H-purine; 3-ethyl-6-ethylamino-8-((3-cyclopentyloxy-4-hydroxy)benzyl)-3H-purine; 3-[3-(3-trimethylsilylethoxymethoxy)cyclopentyloxy-4-methoxy)benzyl)-6-ethylamino-8-isopropyl-3H-purine; 6-Ethylamino-3-[3-(furan-2-yl-methoxy)-4-methoxy-benzyl]-8-isopropyl-3H-purine; 6-Ethylamino-3-[3-(3-hydroxycyclopentyloxy)-4-methoxy-benzyl]-8-isopropyl-3H-purine; 6- Amino 3-[3-(3-hydroxycyclopentyloxy)-4-methoxy-benzyl]-8-isopropyl-3H-purine; 3-[(3-cyclopentyloxy-4-methoxy)benzyl]-6-ethylamino-8-[(1-hydroxy-1-methyl)ethyl]-3H-purine; 6-Ethylamino-3-(3-butoxy-4-methoxy-benzyl)-8-isopropyl-3H-purine; 6-amino-3-[(3-cyclopentyloxy-4-methoxy)benzyl]-8-[(1-hydroxy-1-methyl)ethyl]-3H-purine; 6-ethylamino-2-(3,4-dimethoxybenzyl)-8-isopropyl-3H-purine; 6-Amino-3-(3-cyclopentyloxy-4-methoxybenzyl)-3H-purine; 3-(3-cyclopentyloxy-4-methoxybenzyl)-6-dimethylamino-8-isopropyl-3H-purine; 6-Ethylamino-3-[3-(3-hydroxycyclopentyloxy)-4-methoxybenzyl)]-8-(1-hydroxy-1-methylethyl)-3H-purine; 6-ethylamino-9-[(3-cyclopentyloxy-4-methoxy)benzyl]-8-isopropyl-3H-purine; 3-(3-cyclopentyloxy-4-methoxybenzyl)-6-amino-8-isopropyl-3H-purine; 3-(3-cyclopentyloxy-4-methoxybenzyl)-6-(3-cyclopentyloxy-4-methoxybenzylamino)-8-isopropyl-3H-purine; 6-ethylamino-8-isopropyl-3-(4-methoxybenzyl)-3H-purine; 3-(3-((3-hydroxy)cyclopentyloxy)-4-methoxybenzyl)-6-ethylamino-8-isopropyl-3H-purine; 3-(3-cyclopentyloxy-4-methoxybenzyl)-6-(N-benzoyl-N-ethylamino)-8-isopropyl-3H-purine; 3-(4-chlorobenzyl)-6-cyclopropylamino-8-isopropyl-3H-purine; 6-ethylamino-8-isopropyl-3-[(4-methoxy-3-(4-hydroxybutoxy))benzyl]-3H-purine; 6-ethylamino-3-(4-fluorobenzyl)-8-isopropyl-3H-purine; 3-(3-chlorobenzyl)-6-ethylamino-8-isopropyl-3H-purine 3-[3-(3-Hydroxy-cyclopentyloxy)-4-methoxy-benzyl]-8-(1-hydroxy-1-methyl-ethyl)-3H-purine; 3-[3-(3-hydroxy)cyclopentyloxy)]-4-methoxy)benzyl)-6-ethylamino-8-isopropyl-3H-purine; 6-amino-3-(3,4-dimethoxybenzyl)-8-isopropyl-3H-purine; 6-Ethylamino-3-[3-cyclopentylmethoxy-4-methoxy-benzyl]-8-isopropyl-3H-purine; 6-ethylamino-3-(3-hydroxy-4-methoxybenzyl)-8-isopropyl-3H-purine; 6-Ethylamino-3-[3-(2,2-dimethylaminoethoxy-4-methoxy)]-8-isopropyl-3H-purine; 3-[(3-cyclopentyloxy-4-methoxy)benzyl]-8-[(1-methyl-1-hydroxy)ethyl]-6-ethylamino-3H-purine; 3-(3-cyclopentyloxy-4-methoxybenzyl)-6-((2,2,2-trifluoroethyl)amino)-8-isopropyl-3H-purine; 6-Ethylamino-3-[3-(2,2,2)-azabicyclooctan-3-yloxy)-4-methoxy]-8-isopropyl-3H-purine; 6-Ethylamino-3-[3-(1-methylpiperidin-4-yl-methoxy)-4-methoxy-benzy]-8-isopropyl-3H-purine; 6-amino-8-isopropyl-3-[(4-methoxy-3-([(4-hydroxybutoxy))benzyl]-3H-purine; 3-{2-(4-chlorophenyl)-ethyl]-6-ethylamino-8-isopropyl-3H-purine; 3-(4-chlorobenzyl)-6-((1-hydroxy)cyclopentylamino)-8-isopropyl-3H-purine; 3-(4-chlorobenzyl)-6-cyclopentylamino-8-isopropyl-3H-purine; 6-amino-3(3,4-methylenedioxybenzyl)-8-isopropyl-3H-purine; 6-Ethylamino-3-[(exo-8-methyl-8-azabicyclo(3,2,1)-octan-3-yl-oxy)-4-methoxy-benzy]-8-isopropyl-3-H-purine; 3-(4-chlorophenyl)-6-ethylamino-8-isopropyl-3H-purine; 6-ethylamino-3-[(3-hydroxy-4-methoxy)benzyl]-8-[(1-hydroxy-1-methyl)ethyl]-3H-purine; 6-Ethylamino-3-[(3-pyridin-4-yl-methoxy)N-oxide-4-methoxy]-8-isopropyl-3H-purine; 3-[3-Cyclohexanyl-4-oxy-4-methoxy-benzyl]-6-ethylamino-8-isopropyl-3H-purine; 3-(4-chlorobenzyl)-2,6-di(ethylamino)-8-isopropyl-3H-purine; 6-amino-3-(3-hydroxy-4-methoxy)-benzyl)-8-isopropyl-3H-purine; 6-amino-3-[3-(4-hydroxybutoxy-4-methoxy)benzyl]-8-(1-hydroxy-1-methylethyl)-3H-purine; 6-amino-3-(4-chlorobenzyl)-8-isopropyl-3H-purine; 6-amino-3-cyclopentylmethyl-8-isopropyl-3H-purine; 8-cyclopropyl-3-ethyl-6-ethylamino-3H-purine; 6-Ethylamino-8-isopropyl-3-[3-(pyridin-4-yl-methoxy)-4-methoxy-benzyl]-3H-purine; 6-Ethylamino-3-(1-oxopyridin-4-yl-methyl)-8-isopropyl-3H-purine, and 6-amino-3-[(3-hydroxy-4-methoxy)benzyl)]]-8-[(1-hydroxy-1-methyl)ethyl]-3H-purine, 3-(3-COOmethyl-4-methoxbenzyl)-6-ethylamino-8-isopropyl-3H-purine, 3-(3-piperadine-4-methoxbenzyl)-6-ethylamino-8-isopropyl-3H-purine; 3-(3-COOH-4-methoxbenzyl)-6-ethylamino-8-isopropyl-3H-purine, 3-(3-pyrrole-benzyl)-6-ethylamino-8-isopropyl-3H-purine, 3-butyl-6-pentylamino-8-cyclopropyl-3H-purine, 3-butyl-6-cyclopentylamino-8-cyclopropyl-3H-purine, 3-butyl-6-dimethylamino-8-cyclopropyl-3H-purine and their pharmaceuticaly acceptable salts.

In other preferred embodiments, the adenine compound is selected from the group consisting of 6-amino-3-[(3- cyclopentyloxy-4-methoxy)benzyl]-8-[(1-(2-methoxy)
benzyloxy-1-methyl)ethyl]-3H-purine; 6-amino-3-[(3-
cyclopentyloxy-4-methoxy)benzyl]-8-[(1-(3-methoxy)
benzyloxy-1-methyl)ethyl]-3H-purine; 6-amino-3-[(3,4-
dimethoxy)benzyl]-8-[(1-(4-methyl)benzyloxy-1-methyl)
ethyl]-3H-purine; 6-amino-3-[(3-cyclopentyloxy-4-
methoxy)benzyl]-8-[(1-(4-chloro)benzyloxy-1-methyl)
ethyl]-3H-purine; 6-amino-3-[(3-cyclopentyloxy-4-
methoxy)benzyl]-8-[(1-(2-fluoro)benzyloxy-1-methyl)
ethyl]-3H-purine; 6-amino-3-[(3-cyclopentyloxy-4-
methoxy)benzyl]-8-[(1-(3-fluoro)benzyloxy-1-methyl)
ethyl]-3H-purine; 6-(3-fluoro)benzyloxyamino-3-[(3-
cyclopentyloxy-4-methoxy)benzyl]-8-[(1-(3-fluoro)
benzyloxy-1-methyl)ethyl]-3H-purine; 6-amino-3-[(3-
cyclopentyloxy-4-methoxy)benzyl]-8-[(1-(3,5-dimethoxy)
benzyloxy-1-methyl)ethyl]-3H-purine; 6-amino-3-[(3-
cyclopentyloxy-4-methoxy)benzyl]-8-[(1-(3,4-dimethoxy)
benzyloxy-1-methyl)ethyl]-3H-purine; 6-amino-3-[(3-
cyclopentyloxy-4-methoxy)benzyl]-8-[(1-(3,4-fluoro)
benzyloxy-1-methyl)ethyl]-3H-purine; 6-amino-3-[(3-
cyclopentyloxy-4-methoxy)benzyl]-8-[(3,4-
methylenedioxybenzyloxy-1-methyl)ethyl]-3H-purine;
6-amino-3-[(3-cyclopentyloxy-4-methoxy)benzyl]-8-[(2-
thienylmethoxy-1-methyl)ethyl]-3H-purine; 6-amino-3-[(3-
cyclopentyloxy-4-methoxy)benzyl]-8-[(3-thienylmethoxy-
1-methyl)ethyl]-3H-purine; 6-amino-3-[(3-cyclopentyloxy-
4-methoxy)benzyl]-8-[(1-(1-oxo-octyl)amino-1-methyl)
ethyl]-3H-purine; 6-amino-3-(3,4-methylenedioxybenzyl)-
8-[(1-(4-fluorobenzyloxy)-1-methyl-ethyl]-3H-purine;
6-amino-3-[(3-cyclopentyloxy-4-methoxy)benzyl]-8-[1-(4-
pyridylmethoxy)-methyl-ethyl]-3H-purine; 6-ethylamino-3-
(3-benzyloxy-4-methoxybenzyl)-8-isopropyl-3H-purine;
3-[(3-benzyloxy-4-methoxy)benzyl-8-[(1-benyloxy-1-
methyl)-ethyl]-6-ethylamino-3H-purine; 6-Amino-3-(3-
cyclopentyloxy-4-methoxy-benzyl)-8-[1-(4-
methoxybenzyloxy)-1-methyl-ethyl]-3H-purine; 6-Amino-
3-(3-cyclopentyloxy-4-methoxy-benzyl)-8-(1-
methylethenyl)-3H-purine; 6-Amino-8-benzyloxymethyl-3-
(3-cyclopentyloxy-4-methoxy-benzyl)-3H-purine; 6-amino-
8-[(1-benzyloxy-1-methyl)ethyl]-3-[(3-cyclopentyloxy-4-
methoxy)benzyl]-3H-purine; 6-Amino-3-(3-
cyclopentyloxy-4-methoxybenzyl)-8-[1-(4-
fluorobenzyloxy)-1-methyl-ethyl]-3H-purine; [8-(1-
benzyloxy-1-methyl)ethyl]3-[(3-cyclopentyloxy-4-
methoxy)benzyl]-6-ethylamino-3H-purine; 6-ethylamino-8-
benzyloxymethyl-3-(3-cyclopentyloxy-4-methoxy-benzyl)-
3H-purine; 6-ethylamino-3-(3-,4-methylenedioxybenzyl)-8-
isopropyl-3H-purine; 3-(3-benzyloxy-4-methoxy-benzyl)-
6-ethylamino-8-isopropyl-3H-purine; 6-Amino-3-(3,4-
dimethoxybenzyl)-8-[1-(4-fluorobenzyloxy)-1-
methylethyl]-3H-purine; 6-(amino-8-(1-benzyloxy-1-
methylethyl)-3-(3,4-dimethoxybenzyl)-3H-purine;
6-amino-3-[(3-benzyloxy-4-methoxy)benzyl]-8-[(1-
benzyloxy-1-methyl)ethyl]-3H-purine; 6-Amino-3-(3,4-
dimethyoxybenzyl)-8-(1-methylethenyl)-3H-purine
6-amino-3-((3-benzyloxy-4-methoxy)-bezyl)-8-isopropyl-
3H-purine; 3-(3-benzyloxy-4-nitro-benzyl)-6-ethylamino-8-
isopropyl-3H-purine; 3-[(3-cyclopentyloxy-4-methoxy)
benzyl]-6-ethylamino-8-(1-methyl-ethenyl)-3H-purine and
pharmaceutically acceptable salts thereof.

In certain preferred embodiments, the adenine compound
is selected from 3-(3-cyclopentyloxy-4-methoxybenzyl)-6-
ethylamino-3H-purine (PDE IV $I_{50}$=2.15 $\mu$M); 3-(4-
chlorobenzyl)-6-ethylamino-8-isopropyl-3H-purine (PDE
IV $I_{50}$=1.13 $\mu$M); 3-(3-cyclopentyloxy-4-methoxybenzyl)-
6-ethylamino-8-isopropyl-3H-purine (PDE IV $I_{50}$=0.32
$\mu$M); and (particularly preferred) 6-cyclopentyl-8-
cyclopropyl-3-propyl-3H-purine (PDE IV $I_{50}$=0.03 $\mu$M);
and their pharmaceutically acceptable salts.

The present invention is also related to isoguanine compounds which are precursors of the adenine compounds described above. In addition to their role as precursor compounds, it has been surprisingly discovered that these compounds also have significant PDE IV inhibitory activity.

The present invention therefore is directed in part to a compound of the formula (II)

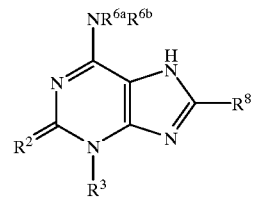

(II)

wherein
R$_2$ is O or S; and R$_3$, R$_{6a}$, R$_{6b}$ and R$_8$ are the same or different and are represent the same groups as those set forth with respect to compound (I) above.

Preferred isoguanine compounds according to the present invention include 6-cyclopentyamino-8-cyclopropyl-3,7-dihydro-3-propyl-2-thio-2H-purin-2-one (PDE IV $I_{50}$=7.41 $\mu$M); 8-cyclopropyl-3,7-dihydro-6-(2-hydroxythylamino)-2-thio-2H-purin-2-one (PDE IV $I_{50}$=4.48 $\mu$M); (particularly preferred) 8-cyclopropyl-3,7-dihydro-6-(4-pyridylmethylamino)-2-thio-2H-purin-2-one (PDE IV $I_{50}$= 0.41 $\mu$M); and their pharmaceutically acceptable salts.

The present invention is also related to 2,6-dithioxanthine compounds which are precursors of the adenine compounds described above. In addition to their role as precursor compounds, it has been surprisingly discovered that these compounds also have significant PDE IV inhibitory activity.

The present invention therefore is directed in part to a compound of the formula (III)

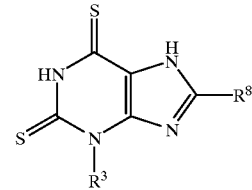

(III)

wherein
R$_3$ and R$_8$ are the same or different and are represent the same groups as those set forth with respect to compound (I) above.

Preferred dithioxanthine compounds according to the present invention include 3-benzyl-3,7-dihydro-8-(1-methylethyl)-2,6-dithio-1H-purin-2,6-dione (PDE IV $I_{150}$= 3.40 $\mu$M); 3.03 $\mu$M); 3-(4-chlorobenzyl)-8-isopropyl-3,7-dihydro-2,6-dithio-3,7-purin-2,6-dione (PDE dione (PDE IV $I_{50}$=2.27 $\mu$M); 3-(3-cyclopentyloxy-4-methoxybenzyl)-3,7-dihydro-8-isopropyl-2,6-dithio-1H-purin-2,6-dione (PDE IV $I_{50}$=0.80 $\mu$M); (particularly preferred) 8-cyclopropyl-3,7-dihydro-1,3-diethyl-2,6-dithio-1H-purin-2,6-dione (PDE IV $I_{50}$=0.42 $\mu$M); and their pharmaceutically acceptable salts.

As used herein, the following terms are intended to have the meaning as understood by persons of ordinary skill in the art, and are specifically intended to include the meanings set forth below:

As used herein, the term "alkyl" means a linear or branched saturated aliphatic hydrocarbon group having a single radical and 1–10 carbon atoms. Examples of alkyl groups include methyl, propyl, isopropyl, butyl, n-butyl, isobutyl, sec-butyl, tert-butyl, and pentyl. A branched alkyl means that one or more alkyl groups such as methyl, ethyl or propyl, replace one or both hydrogens in a —CH$_2$— group of a linear alkyl chain.

The term "cycloalkyl" means a non-aromatic mono- or multicyclic hydrocarbon ring system having a single radical and 3–12 carbon atoms. Exemplary monocyclic cycloalkyl rings include cyclopropyl, cyclopentyl, and cyclohexyl. Exemplary multicylic cycloalkyl rings include adamantyl and norbornyl.

The term "alkenyl" means a linear or branched aliphatic hydrocarbon group containing a carbon—carbon double bond having a single radical and 2–10 carbon atoms. A "branched" alkenyl means that one or more alkyl groups such as methyl, ethyl or propyl replace one or both hydrogens in a —CH$_2$— or —CH= linear alkenyl chain. Exemplary alkenyl groups include ethenyl, 1- and 2-propenyl, 1-, 2- and 3-butenyl, 3-methylbut-2-enyl, 2-propenyl, heptenyl, octenyl and decenyl.

The term "cycloalkenyl" means a non-aromatic monocyclic or multicyclic hydrocarbon ring system containing a carbon—carbon double bond having a single radical and 3 to 12 carbon atoms. Exemplary monocyclic cycloalkenyl rings include cyclopropenyl, cyclopentenyl, cyclohexenyl or cycloheptenyl. An exemplary multicyclic cycloalkenyl ring is norbornenyl.

The term "cycloaklylalkyl" or "cycloalkyl-alkyl" means a non-aromatic mono- or multicyclic ring system, wherein the ring is substituted with an alkyl group, as defined above to include a linear or branched aliphatic hydrocarbon group having a single radical The term "aryl" means a carbocyclic aromatic ring system containing one, two or three rings which may be attached together in a pendent manner or fused, and containing a single radical. Exemplary aryl groups include phenyl and naphthyl.

The term "aralkyl" or "arylalkyl" or "aryl-alkyl" means an alkyl group as defined above to include a linear or branched saturated aliphatic hydrocarbon group having a single radical, wherein the alkyl is substituted with an aryl group, as defined above to include a carbocyclic aromatic ring system containing one, two or three rings which may be attached together in a pendent manner or fused, and containing a single radical.

The term "heterocyclic" or "heterocyclyl" means cyclic compounds having one or more heteroatoms (atoms other than carbon) in the ring, and having a single radical. The ring may be saturated, partially saturated and unsaturated, and the heteroatoms may be selected from the group consisting of nitrogen, sulfur and oxygen. Examples of saturated heterocyclic radicals include saturated 3 to 6-membered heteromonocyclic groups containing 1 to 4 nitrogen atoms, such as pyrrolidinyl, imidazolidinyl, piperidino, piperazinyl; saturated 3- to 6-membered heteromonocyclic groups containing 1 to 2 oxygen atoms and 1 to 3 nitrogen atoms, such as morpholinyl; saturated 3- to 6-membered heteromonocyclic groups containing 1 to 2 sulfur atoms and 1 to 3 nitrogen atoms, such as thiazolidinyl. Examples of partially saturated heterocyclic radicals include dihydrothiophene, dihydropyran, and dihydrofuran.

The term "heteroaryl" means unsaturated heterocyclic radicals, wherein heterocyclic is as previously described. Exemplary heteroaryl groups include unsaturated 3 to 6 membered heteromonocyclic groups containing 1 to 4 nitrogen atoms, such as pyrrolyl, pyridyl, pyrimidyl, and pyrazinyl, unsaturated condensed heterocyclic groups containing 1 to 5 nitrogen atoms, such as indolyl, quinolyl, isoquinolyl; unsaturated 3 to 6 membered heteromonocyclic groups containing an oxygen atom, such as furyl; unsaturated 3 to 6 membered heteromonocyclic groups containing a sulfur atom, such as thienyl; unsaturated 3 to 6 membered heteromonocyclic groups containing 1 to 2 oxygen atoms and 1 to 3 nitrogen atoms, such as oxazolyl; unsaturated condensed heterocyclic groups containing 1 to 2 oxygen atoms and 1 to 3 nitrogen atoms, such as benzoxazolyl; unsaturated 3 to 6 membered heteromonocyclic groups containing 1 to 2 sulfur atoms and 1 to 3 nitrogen atoms, such as thiazolyl; unsaturated condensed heterocyclic group containing 1 to 2 sulfur atoms and 1 to 3 nitrogen atoms, such as benzothiazolyl. The term "heteroaryl" also includes unsaturated heterocyclic radicals, wherein heterocyclic is as previously described, in which the heterocyclic group is fused with an aryl group, in which aryl is as previously described. Exemplary fused radicals include benzofuran, benzdioxole and benzothiophene.

The term "heterocyclylalkyl" means heterocyclic groups, as defined above to include compounds having one or more heteroatoms (atoms other than carbon) in the ring, and having a single radical, wherein the ring may be saturated, partially saturated and unsaturated, and the heteroatoms may be selected from the group consisting of nitrogen, sulfur and oxygen, in which the heterocyclic group is substituted with an alkyl group, as defined above to include linear or branched saturated aliphatic hydrocarbon group having a single radical. Exemplary heterocyclylalkyl groups include pyrrolidinyl-methyl, imidazolidinyl-methyl, piperidino-methyl, piperazinyl-methyl, morpholinyl-methyl, and thiazolidinyl-methyl.

The term "heteroaralkyl" or "heteroarylalkyl" means heteroaryl radicals, wherein heteroaryl is as previously described, wherein the heteroaryl group is substituted with an alkyl group as defined above to include linear or branched saturated aliphatic hydrocarbon groups having a single radical. Exemplary heteroaralkyl groups include pyrrolyl-methyl, pyridyl-methyl, pyrimidyl-methyl, pyrazinyl-methyl, indolyl-methyl, quinolyl-methyl, isoquinolyl-methyl, furyl-methyl, thienyl-methyl, oxazolyl-methyl, benzoxazolyl-methyl, thiazolyl-methyl, benzothiazolyl-methyl, benzofuran-methyl and benzothiophene-methyl.

The term "acyl" means an H—C(O)- or alkyl-C(O)-group in which the alkyl group is as previously described. Exemplary acyl groups include formyl, acetyl, propanoyl, and 2-methylpropanoyl.

The term "alkoxy" means an alkyl-O-group in which the alkyl group is as previously defined, to include a linear or branched saturated aliphatic hydrocarbon group having a single radical. Exemplary alkoxy groups include methoxy, ethoxy, n-propoxy, i-propoxy, and n-butoxy. The term "cycloalkoxy" means a cycloalkyl-O-group in which the cycloalkyl group is as previously defined, to include non-aromatic mono- or multicyclic hydrocarbon ring systems having a single radical. Exemplary cycloalkoxy groups include cyclopentyloxy.

The term "amido" or "aminocarbonyl" means —C(O)NH$_2$.

The term "amino" means the group —NH$_2$—. The term "alkylamino" means an amino group which has been substituted with an alkyl group as defined above, and the term dialkylamino means an amino group which has been substituted with two alkyl groups, as defined above. The term "acylamino" means an amino group which has been substituted with an acyl group as defined above.

The term "carbamyl" is the group $CH_2NO$.

The term "sulfonyl" means the divalent radical $SO_2$. The term "alkylsulfonylamino" means a sulfonyl group which is substituted with an amino group as defined above, and an alkyl group as defined above.

As used herein, the term "patient" includes both human and other mammals.

The invention disclosed herein is meant to encompass all pharmaceutically acceptable salts thereof of the disclosed compounds. The pharmaceutically acceptable salts include, but are not limited to, metal salts such as sodium salt, potassium salt, secium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate, and the like; amino acid salts such as arginate, asparginate, glutamate and the like.

The invention disclosed herein is also meant to encompass all prodrugs of the disclosed compounds. Prodrugs are considered to be any covalently bonded carriers which release the active parent drug in vivo.

The invention disclosed herein is also meant to encompass the in vivo metabolic products of the disclosed compounds. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled compound of the invention, administering it parenterally in a detectable dose to an animal such as rat, mouse, guinea pig, monkey, or to man, allowing sufficient time for metabolism to occur and isolating its conversion products from the urine, blood or other biological samples.

The invention disclosed herein is also meant to encompass the disclosed compounds being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Some of the compounds disclosed herein may contain one or more asymmetric centers and may thus give rise to enantiomers, diastereomers, and other stereoisomeric forms. The present invention is also meant to encompass all such possible forms as well as their racemic and resolved forms and mixtures thereof When the compounds described herein contain olefinic double bonds or other centers of geometric asymmetry, and unless specified otherwise, it is intended to include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The term "enantiomer" or "enantiomeric" refers to a molecule that is nonsuperimposeable on its mirror image and hence optically active wherein the enantiomer rotates the plane of polarized light in one direction and its mirror image rotates the plane of polarized light in the opposite direction.

The term "racemic" refers to a mixture of equal parts of enantiomers and which is optically inactive.

The term "resolution" refers to the separation or concentration or depletion of one of the two enantiomeric forms of a molecule.

DETAILED DESCRIPTION OF THE INVENTION

The compounds of the present invention can be administered to anyone requiring PDE IV inhibition. Administration may be orally, topically, by suppository, inhalation or insufflation, or parenterally.

The present invention also encompasses all pharmaceutically acceptable salts of the foregoing compounds. One skilled in the art will recognize that acid addition salts of the presently claimed compounds may be prepared by reaction of the compounds with the appropriate acid via a variety of known methods.

Various oral dosage forms can be used, including such solid forms as tablets, gelcaps, capsules, caplets, granules, lozenges and bulk powders and liquid forms such as emulsions, solution and suspensions. The compounds of the present invention can be administered alone or can be combined with various pharmaceutically acceptable carriers and excipients known to those skilled in the art, including but not limited to diluents, suspending agents, solubilizers, binders, disintegrants, preservatives, coloring agents, lubricants and the like.

When the compounds of the present invention are incorporated into oral tablets, such tablets can be compressed, tablet triturates, enteric-coated, sugar-coated, film-coated, multiply compressed or multiply layered. Liquid oral dosage forms include aqueous and nonaqueous solutions, emulsions, suspensions, and solutions and/or suspensions reconstituted from non-effervescent granules, containing suitable solvents, preservatives, emulsifying agents, suspending agents, diluents, sweeteners, coloring agents, and flavoring agents. When the compounds of the present invention are to be injected parenterally, they may be, e.g., in the form of an isotonic sterile solution. Alternatively, when the compounds of the present invention are to be inhaled, they may be formulated into a dry aerosol or may be formulated into an aqueous or partially aqueous solution.

In addition, when the compounds of the present invention are incorporated into oral dosage forms, it is contemplated that such dosage forms may provide an immediate release of the compound in the gastrointestinal tract, or alternatively may provide a controlled and/or sustained release through the gastrointestinal tract. A wide variety of controlled and/or sustained release formulations are well known to those skilled in the art, and are contemplated for use in connection with the formulations of the present invention. The controlled and/or sustained release may be provided by, e.g., a coating on the oral dosage form or by incorporating the compound(s) of the invention into a controlled and/or sustained release matrix.

Specific examples of pharmaceutically acceptable carriers and excipients that may be used to formulate oral dosage forms, are described in the *Handbook of Pharmaceutical Excipients*, American Pharmaceutical Association (1986), incorporated by reference herein. Techniques and compositions for making solid oral dosage forms are described in *Pharmaceutical Dosage Forms: Tablets* (Lieberman, Lachman and Schwartz, editors) 2nd edition, published by Marcel Dekker, Inc., incorporated by reference herein. Techniques and compositions for making tablets (compressed and molded), capsules (hard and soft gelatin) and pills are also described in *Remington's Pharmaceutical Sciences* (Arthur Osol, editor), 1553–1593 (1980), incorporated herein by reference. Techniques and composition for making liquid oral dosage forms are described in *Pharmaceutical Dosage Forms: Disperse Systems*, (Lieberman, Rieger and Banker, editors) published by Marcel Dekker, Inc., incorporated herein by reference.

When the compounds of the present invention are incorporated for parenteral administration by injection (e.g., continuous infusion or bolus injection), the formulation for parenteral administration may be in the form of suspensions, solutions, emulsions in oily or aqueous vehicles, and such formulations may further comprise pharmaceutically necessary additives such as stabilizing agents, suspending agents, dispersing agents, and the like. The compounds of the invention may also be in the form of a powder for reconstitution as an injectable formulation.

The dose of the compounds of the present invention is dependent upon the affliction to be treated, the severity of the symptoms, the route of administration, the frequency of the dosage interval, the presence of any deleterious side-effects, and the particular compound utilized, among other things.

The following examples illustrate various aspects of the present invention, and are not to be construed to limit the claims in any manner whatsoever.

EXAMPLE 1

3,8-Diethyl-6-morpholino-3H-purine (i) 38-Diethyl-hypoxanthine 3,8-diethyl-2-thioxanthine (18.9 g) was dissolved in 370 ml of 2N NaOH Nickel aluminum alloy (75.6 g) (1.4M of Al and 0.6M of Ni) was added in portions over 1.5 hrs at 65° C. After a further 0.5 hr at 65–70° C. the reaction product was filtered, washed with 200 ml of 1N NaOH and the filtrate neutralized with 183 ml of 5N HCl to pH 7. The formed aluminum hydroxide was filtered off, the filtrate concentrated to dryness, the residue suspended in 500 ml of absolute ethanol at 90° C., and the insoluble NaCl filtered off and washed. The filtrate was concentrated to dryness, dissolved in 200 ml of chloroform, filtered and concentrated to dryness again. The residue was crystallized from 150 ml of ethanol to give 3,8-di-ethyl-hypoxanthine (12.68 g) with mp (sublimation at 220° C.) 305–307° C. under decomposition.

(ii) 3,8-Diethyl-6-thiohypoxanthine

The product of stage (i) (8.65 g) and phosphorus pentasulfide (12.0 g) was refluxed in 150 ml of pyridine for 1 hr. Under cooling 59.4 ml of 2N NaOH was added dropwise, the solid filtered off and washed with water. The filtrate was concentrated in vacuo to dryness and the residue suspended in 200 ml of water and collected. The filtrate was extracted three times with 600 ml of chloroform. The residue of the organic phase was combined with the solid collected (total 6.08 g), dissolved in 500 ml of chloroform and filtered through 24 g of silicagel. Fractions 2 and 3 eluted 4.63 g of crude product which was crystallized from 120 ml of methanol to give 3,8-diethyl-6-thiohypoxanthine (3.58 g) with mp (sublimation at 210° C.) 250–270° C. under decomposition. A second crop gave 0.58 g.

| Elemental analysis: | | | | |
|---|---|---|---|---|
| % calc | C 51.90 | H 5.81 | N 26.90 | S 15.40 |
| % found | C 51.76 | H 6.01 | N 26.82 | S 15.64 |

(iii) 3,8-Diethyl-6-morpholino-3H-purine

The product of stage (ii) (52 mg) in 5 ml of morpholine was refluxed for 21 hrs. Evaporation in vacuo gave 65 mg of crude 3,8-diethyl-6-morpholino-3H-purine.

EXAMPLE 2

3,8-Diethyl-6-morpholino-3H-purine (i) 3,8-Diethyl-2,6-dithioxanthine 19.14 g of 3,8-diethyl-2-thioxanthine and 22.75 g of phosphorus pentasulfide were refluxed in 280 ml of pyridine for 4.5 hrs. After cooling to room temperature 113 ml of 2N NaOH were added during 15 minutes under vigorous stirring and cooling. The suspension was filtered, washed with pyridine and concentrated in vacuo. The residue was suspended in 150 ml of water and concentrated to remove the pyridine. Suspension in water and collection of the solid gave the crude product, which is dissolved in 150 ml of 1N NaOH, treated with two portions of 0.5 g of charcoal, and filtered. The filtrate was slowly acidified with 38 ml of 5N HCl to pH 3 and a solid collected. The dried crude product (19.85 g) was suspended in 400 ml of 2-propanol at 95° C. After cooling to room temperature the solid (17.62 g) is collected and washed.

(ii) 3,8-Diethyl-3,7-dihydro-6-morpholino-2H-purine-2-thione

The product of stage (i) (14.42 g) was refluxed in 78.4 ml (900 mmoles) of morpholine for 30 hours. After cooling to room temperature the reaction product was suspended in 100 ml of acetone and the title product (16.49 g) collected and washed.

3,8-diethyl-3,7-dihydro-6-morpholino-2H-purine-2-thione melting point: 295–298° C. (with decomposition).

| Elemental analysis: | | | | |
|---|---|---|---|---|
| Calc. | C 53.22 | H 6.53 | N 23.87 | S 10.93 |
| Found | C 53.01 | H 6.77 | N 23.82 | S 10.97 |

(iii) 3,8-Diethyl-6-morpholino-3H-purine

The product of stage (ii) (7.34 g) was dissolved in 150 ml of 2N NaOH. Ni—Al alloy 50% (22.95 g)(425 mmoles of Al and 196 mmoles of Ni) was added over 1.25 hours at 65° C. After another 1.5 hours at 65–70° C. additional 15 ml of 10N NaOH and in portions 11.48 of Ni—Al alloy 50% was added. After another 0.5 hour at 65–70° C. the reaction product was left over night. Dichloromethane (100 ml) was added, the suspension was filtered and the nickel washed with dichloromethane (200 ml) and water (100 ml). The organic phase was separated, washed twice with water and concentrated. The residue was triturated in 50 ml of petroleum-ether to give the title product as a solid (5.40 g) mp 103–107° C.

| Elemental analysis: | | | |
|---|---|---|---|
| % calc | C 59.75 | H 7.33 | N 26.80 |
| % found | C 59.64 | H 7.55 | N 26.35 |

HCl salt crystallized from acetone has mp; (sublimation 145° C.) 220–222° C.

EXAMPLE 3

8-Cyclopropyl-3-ethyl-6-ethylamino-3H-purine (i) 8-Cyclopropyl-3-ethyl-6-ethylamino-3,7-dihydro-2H-purine-2-thione 8-cyclopropyl-3-ethyl-2,6-dithioxanthine (20.19 g) prepared according to the method of example 2(i), and 70% ethylamine in water (320 ml 4.0M) were placed in a 450 ml pressure reactor and heated to 150° C. for 6 hours. The reaction solution was cooled to room temperature, treated with 2 portions of charcoal (0.2 g) filtered, and evaporated to dryness. The residue was triturated in methanol (300 ml), concentrated to about 200 ml, and the solid collected (16.48 g), mp 265° with decomposition.

(ii) 8-Cyclopropyl-3-ethyl-6-ethylamino-3H-purine

The product of step (i) (11.85 g) was dissolved in 2N NaOH (270 ml) and 10N NaOH (27 ml) and heated to 65° C. Within 1.25 hours 50% Ni—Al alloy (518 mmoles of Ni and 1125 mmoles of Al) (60.8 g) was added under vigorous stirring at 65–70° C. After a further 0.75 hr at the same temperature the reaction mixture was cooled to room temperature and treated with chloroform (400 ml). The nickel was filtered off and washed with 350 ml of chloroform and 150 ml of water. The filtrate was separated and the chloroform layer evaporated to dryness. The residue (19.64 g) was dissolved in acetone (100 ml), treated with 2 portions of charcoal (0.15 g) filtered, and evaporated. The residue was treated with diethylether (100 ml) and crystals collected (6.10 g), mp 80–96° C. A second crop gave 1.25 g. A recrystallized sample from diisopropylether had mp 103–105° C.

| Elemental analysis with 3.3% of water: | | | | |
|---|---|---|---|---|
| % calc | C 60.25 | H 7.54 | N 29.28 | O 2.93 |
| % found | C 60.52 | H 7.46 | N 29.10 | O 2.92* |

*(by difference)

EXAMPLE 4

A. 8-(3-Cyclopentyloxy-4-methoxybenzyl)-3-ethyl-6-ethylamino-3H-purine Hydrochloride B. 8-(3-Cyclopentyloxy-4-hydroxybenzyl)-3-ethyl-6-ethylamino-3H-purine (i) 3-Cyclopentyloxy-4-methoxy-benzyl Alcohol To a solution of 48.70 g (220 mmoles) of 3-cyclopentyloxy-4-methoxybenzaldehyde in 250 ml of methanol was added portionwise 8.57 g (220 mmoles) of 97% sodium borohydride within 10 min at 15–22° C. under cooling. After a further 20 min the methanol was removed in vacuo and the residue taken up in 10 ml of water and 300 ml of ether. The ether phase was evaporated to dryness: 48.5 g (99.2%) of liquid benzyl alcohol.

(ii) 3-Cyclopentyloxy-4-methoxy-benzyl Cyanide

To a solution of 40.00 g (180 mmoles) of benzyl alcohol in 530 ml of dichloromethane was added within 5 min 32.7 ml (450 mmoles) of thionyl chloride. The solution was evaporated in vacuo to dryness, which was repeated after toluene addition: 46.30 g (106.9%) of crude benzyl chloride, which was dissolved in 230 ml of dimethylformamide and treated with 23.50 g (360 mmoles) of potassium cyanide. The mixture was heated for 4 hours to 50–55° C. The salt was filtered off and the filtrate evaporated in vacuo to dryness, which was repeated after the addition of water, the residue was taken up in ether and extracted with 1N NaOH. The ether phase is evaporated to dryness to yield 41.20 g (99.0%) of crude benzyl cyanide.

(iii) (3-Cyclopentyloxy-4-methoxy-phenyl)acetyl Chloride 42.02 g (180 mmoles) of benzyl cyanide were refluxed in 410 ml of 94% ethanol, 106 ml of water, and 180 ml of 10N NaOH for 20 hours. The ethanol was removed in vacuo, the solution diluted to 800 ml with water, treated twice with 2 g of charcoal, filtered, and acidified with 185 ml of 10N HCl. The acid crystallized slowly, was collected and dried at 30° C.: 42.2 g (92.9%) of acid. 1.51 g (2.3%) could be extracted by ether from the filtrate. Both parts (173 mmoles) are combined and refluxed in 500 ml of dichloromethane and 31.4 ml (433 mmoles) of thionyl chloride for 1.5 hours. The solution was treated twice with 2 g of charcoal, filtered and evaporated to dryness. This was repeated twice with little toluene: 48.70 g (>100%) of crude acetyl chloride as a reddish liquid.

(iv) 8-(3-Cyclopentyloxy-4-methoxy-benzyl)-3-ethyl-2-thioxanthine 10.02 g (45 mmoles) of 5,6-diamino-1-ethyl-2-thiouracil hydrochloride was dissolved in 200 ml of pyridine, treated with 6.05 g (57 mmoles) of sodium carbonate and 15.5 g (56 mmoles) of Example 4 (iii) dissolved in 25 ml of ether added within 10 minutes at 5–10° C. After 1.5 hours at room temperature the solid was filtered off and the filtrate evaporated in vacuo to dryness. The residue was dissolved in 100 ml of 2N NaOH and 200 ml of water and brought to reflux, within 1 hour 70 ml are distilled off. The solution was filtered and neutralized to pH 7.5 with 52 ml of 5N HCl. The solid was collected and dried: 14.37 g (79.7%) of crude 2-thioxanthine (from the water 4.2 g of the phenyl acetic acid was recovered), which was suspended in 250 ml of hot methanol and collected again: 10.68 g (59.3%) of purified 2-thioxanthine, which was dissolved is 100 ml of 1N NaOH and filtered. The filtrate was acidified to pH 6 and the solid collected: 8.82 g (48.9%) of 2-thioxanthine with mp (260° C.) 280–310° C. under decomposition.

(v) 8-(3-Cyclopentyloxy-4-methoxy-benzyl)-3-ethyl-2,6-dithioxanthine 8.41 g (21 mmoles) of 2-thioxanthine are refluxed with 5.60 g (25.2 mmoles) of phosphorus pentasulfide in 80 ml of pyridine. After 5.5 hours 27.7 ml (55.4 mmoles) of 2N NaOH were added at 5–10° C. The solid was filtered off and washed with pyridine. The filtrate was evaporated in vacuo to dryness, the residue is suspended in 200 ml of water with little tetrahydrofuran (THF) for crystallization, the suspension is concentrated and the solid at pH 8 collected and washed. Redissolution in 100 ml of 0.5 N NaOH, treatment with charcoal (20%), filtration and acidification to pH 6 yielded the solid crude dithioxanthine 7.84 g (89.6%). Crystallization from chloroform and suspension in hot methanol gave 5.31 g (60.7%) of dithioxanthine with mp 241–3° C. The mother liquors were combined (2.36 g) and filtered with chloroform through 60 g of silicagel in a column: 1.73 g (19.8%) were isolated as a second crop.

(vi) 8-(3-Cyclopentyloxy-4-methoxy-benzyl)-3-ethyl-6-ethylamino-37-dihydro-2H-purine-2-thione 6.67 g (16 mmoles) of dithioxanthine and 52 ml of 70% ethylamine in water were heated to 150° C. in a pressure reactor (250 psi) for 12 hours under nitrogen. The solution was treated with charcoal (5%), filtered, and evaporated in vacuo to dryness. The residue was suspended in water, acidified with 1N HCl to pH 4 and neutralized to pH 8 with sodium bicarbonate. The solid was collected, washed and dried to give 6.66 g (97.4%) of crude thioisoguanine.

(vii)

A. 8-(3-Cyclopentyloxy-4-methoxy-benzyl)-3-ethyl-6-ethylamino-3H-purine Hydrochloride and B. 8-(3-Cyclopentyloxy-4-hydroxy-benzyl)-3-ethyl-6-ethylamino-3H-purine Hydrochloride 6.41 g (15 mmoles) of crude thioisoguanine and 9.70 g (165 mmoles) of neutral Raney-nickel were refluxed in 70 ml of 1-propanol for 3 hours. The nickel was filtered off and the filtrate evaporated in vacuo to dryness. The residue (5.86 g/98.8%) was dissolved in chloroform and extracted extensively with 1N NaOH. The NaOH solution was acidified with 5N HCl to pH 4 and neutralized with sodium bicarbonate to pH 7.5. An oil precipitated, which crystallized slowly and the solid collected: 0.49 g of 8-(3-cyclopentyloxy-4-hydroxy-benzyl)-3-ethyl-6-ethylamino-3H-purine with mp 172–4° C. The chloroform solution was evaporated to dryness: 3.76 g (63.4%) of crude 3H-purine, which was dissolved in 30 ml of methanol and treated with 10 ml of 1N methanolic HCl. The solution was evaporated in vacuo to dryness and the residue crystallized from acetone-ethyl acetate: 3.66 g (56.5%) of 8-(cyclopentyloxy-4-methoxybenzyl)-3-ethyl-6-ethylamino-3H-purine hydrochloride with mp 169–71° C.

| Elemental analysis for $C_{22}H_{30}ClN_5O_2$ | | | |
|---|---|---|---|
| Calc. | C 61.17 | H 7.00 | N 16.21 |
| Found | C 61.09 | H 6.77 | N 16.18 |

EXAMPLE 5

3-(3-Cyclopentyloxy-4-methoxybenzyl)-6-ethylamino-8-isopropyl-3H-purine Hydrochloride (i) 3-Cyclopentyloxy-4-methoxy-benzaldehyde 77.70 g (500 mmoles) of isovanillin and 69.40 g (600 mmoles) of 97% potassium t-butoxide (t-BuOK) dissolved in 800 ml of 1-propanol, 69.0 ml 630 mmoles), and the solution refluxed. After 3 hours another 9.25 g (80 mmoles) of t-BuOK were added at 80° C. and the suspension refluxed for another 3 hours. The solid was filtered off and the filtrate evaporated in vacuo to dryness. The residue was dissolved in ether and extracted with 1N NaOH. The ether phase was evaporated to dryness: 85.40 g (77.5%) of cyclopentyloxy-benzaldehyde was isolated.

(ii) 3-Cyclopentyloxy-4-methoxy-benzaldehyde-oxime 85.4 g (388 mmoles) of 3-cyclopentyloxy-4-methoxy-benzaldehyde were dissolved in 350 ml of 94% ethanol and added within 10 minutes at 15–20° C. to a solution of 29.7 g (427 mmoles) of hydroxylammonium chloride and 52.8 g (388 mmoles) of sodium acetate trihydrate (3 $H_2O$) in 230 ml of water. After 2 hours the ethanol was removed in vacuo, the residue treated with 16.3 g (194 mmoles) of sodium bicarbonate until $CO_2$ formation ceased and extracted with ether. Evaporation of the ether phase gave 91.0 g (99.7%) of oxime as a mixture of the 2 isomers.

(iii) 3-Cyclopentyloxy-4-methoxy-benzylamine 73.5 g (320 mmoles) of oxime, 80 ml of methanol, 55 g of liquid ammonia, and 18.5 g of neutral Raney-nickel are placed into a 450 ml pressure reactor. Hydrogen gas was added up to a pressure of 1,200 psi and the whole heated to 75–80° C., when the pressure dropped to 600 psi hydrogen gas was added again to 1,200 psi. After 4 hours the pressure reached 1080 psi and remained constant. The nickel was filtered off and washed with methanol. The filtrate is evaporated to dryness, dissolved in ether and extracted with 1N NaOH. The ether phase was evaporated to dryness: 68.9 g (97.3%) of benzylamine.

(iv) 3-Cyclopentyloxy-4-methoxy-benzyl-isothiocyanate 82.3 g (372 mmoles) of benzylamine were dissolved in 10 ml of toluene and added at 15–20° C. (with cooling) within 20 minutes to an emulsion of 22.5 ml (372 mmoles) of carbon disulfide and 14.88 g (372) mmoles) of NaOH in 52 ml of water. The reaction mixture was heated to 75–80° C. for 1 hour and cooled to 40° C. Within 15 minutes, 35.4 ml (372 mmoles) of ethyl chloroformate were added at 40–45° C. The emulsion was brought to about pH 8 with 2N NaOH and heated to 55–60° C., gas formation ceased after about 10 hours keeping the pH at 8 with 2N NaOH (total about 8 ml). The organic layer was collected and the solvent evaporated: 96.3 g (98.3%) of benzyl isothiocyanate.

(v) 1-(3-Cyclopentyloxy-4-methoxy-benzyl)-2-thiourea 96.3 g (366 mmoles) of benzylisothiocyanate were dissolved in 100 ml o THF and treated with 44.2 ml (732 mmoles) of 32% ammonia solution. After 0.5 hour at 40–45° C., 300 ml of water were added and the THF removed in vacuo. The gummy suspension is treated with 200 ml of ether, the crystals collected and washed with water and ether. Suspension in 30 ml of methylenechloride and collection gave 65.77 g (64.2%) of benzyl-2-thiourea with mp 144–5° C.

(vi) 6-Amino-1-(3-cyclopentyloxy-4-methoxy-benzyl)-2-thiouracil 29.65 g (256 mmoles) of 97% t-BuOK were dissolved in 240 ml of 2-propanol. 65.33 g (233 mmoles) of 2-thiourea and 25.3 ml (238 mmoles) of ethyl cyanoacetate were added at 80° C. After 30 minutes at reflux a solution was formed and after 4.5 hours an additional 2.96 g (25.6 mmoles) of t-BuOK and 4.97 ml (46.6 mmoles) of ethyl cyanoacetate added. After 22 hours of refluxing the solid was collected, combined with the residue of the filtrate, dissolved in 1 l of water and precipitated with about 50 ml of 5N HCl (pH 3–4). The solid is collected, washed, dried, recrystallized by suspension in 1 l of refluxing acetone, concentrated to about 300 ml and collected at 23° C.: 80.65 g (85.7%) of uracil containing 1 equivalent of acetone, mp 225–7° C.

(vii) 6-Amino-1-(3-cyclopentyloxy-4-methoxy-benzyl)-5-nitroso-2-thiouracil 68.9 g (170 mmoles) of uracil are dissolved in 650 ml of acetic acid, for removal of acetone 100 ml are distilled off in vacuo, and at 65–70° C. 43.4 ml (174 mmoles) of 4N sodium nitrite solution were added within 10 minutes. After further 5 minutes the suspension was cooled to 30° C. and diluted with 1.7 l of water. The solid was collected, washed, and dried: 64.08 g (100%) of nitrosouracil, which was dissolved in 330 ml of 1N NaOH and 300 ml of water, filtered, and acidified with 5N HCl to pH 2, to keep it in suspension 2 l of water were added. The solid was collected and washed, suspended in 60 ml of methanol and collected again: 54.2 g (84.7%) of nitrosouracil.

(viii) 1-(3-cyclopentyloxy-4-methoxy-benzyl)-5,6-diamino-2-thiouracil 15.06 g (40 mmoles) of nitrosouracil are suspended in 300 ml of THF and hydrogenated with hydrogen gas and 6 g of neutral Raney-nickel for 2.5 hours, when hydrogen uptake ceased. After 1 hour all was dissolved and thereafter a new precipitate formed, which is dissolved in a mixture of methylenechloride and methanol. The nickel was filtered off and the filtrate evaporated in vacuo to dryness: 13.96 g (96.3%) of crude diaminouracil.

(ix) 6-Amino-1-(3-cyclopentyloxy-4-methoxy-benzyl)-5-isobutyrylamino-2-thiouracil A two phase solution of 15.01 g (41.4 mmoles) of diaminouracil, 180 ml of THF, 150 ml of water, 6.96 g (82.8 mmoles) of sodium bicarbonate, and 10.52 ml (62.1 mmoles) of isobutyric anhydride is heated to 55° C. under nitrogen for 1 hour. The THF was evaporated in vacuo and the residue diluted with 200 ml of water (pH 8). The solid was collected, washed, and dried: 16.25 g (90.7%) of isobutyrylaminouracil.

(x) 3-(3-Cyclopentyloxy-4-methoxy-benzyl)-8-isopropyl-2-thioxanthine 17.81 g (41.2 mmoles) of isobutyrylaminouracil were refluxed for 0.75 hour in 120 ml of 1N NaOH and 80 ml of water. The solution was treated twice with 0.5 g of charcoal, filtered, acidified with 5N HCl, and put to pH 7–8 with sodium bicarbonate solution. The solid was collected, washed, and dried: 15.31 g (89.6%) of 2-thioxanthine with mp 270–6° C. (with decomposition).

(xi) 3-(3-Cyclopentyloxy-4-methoxy-benzyl)-8-isopropyl-2,6-dithioxanthine 15.17 g (36.6 mmoles) of 2-thioxanthine and 9.76 g (43.9 mmoles) of phosphorus pentasulfide were refluxed under nitrogen in 140 ml of pyridine for 5.5 hours. At 5–10° C. 48.3 ml (96.6 mmoles) of 2N NaOH were added dropwise. The solid was filtered of and washed with pyridine. The filtrate was evaporated in vacuo to dryness and treated with 300 ml of water. The suspension was adjusted to pH 7 with sodium bicarbonate solution and the solid collected, washed, dissolved in 200 ml of 0.5N NaOH solution, treated twice with 1.6 g of charcoal, filtered, acidified with 5N HCl and neutralized with sodium bicarbonate solution to pH 7. The solid was collected, washed, and dried: 14.64 g (92.9%) of crude dithioxanthine, which was dissolved in 400 ml of methylenechloride and filtered through 60 g of silicagel in a column. The solvent was evaporated and the residue suspended in 20 ml of 100% ethanol and collected: 14.34 g (82.2%) of dithioxanthine with mp 204–6° C. (containing 1 mol EtOH).

(xii) 3-(3-Cyclopentyloxy-4-methoxy-benzyl)-3,7-dihydro-6-ethylamino-8-isopropyl-2H-purine-2-thione 6.20 g (13 mmoles) of dithioxanthine and 42 ml of 70% ethylamine in water were placed into a 450 ml pressure reactor and heated to 150° C. (240 psi) for 12 hours. The solution was filtered and evaporated to dryness. The residue was suspended in water, acidified with 1N HCl to pH 3, and neutralized with sodium bicarbonate solution to pH 7–8. The solid was collected, washed, and dried: 5.48 g (95.5%) of thioisoguanine with mp 72–7° C.

(xiii) 3-(3-Cyclopentyloxy-4-methoxybenzyl)-6-ethylamino-8-isopropyl-3H-purine Hydrochloride 5.43 g (12.3 mmoles) of thioisoguanine and 7.9 g of neural Raney-nickel were refluxed in 60 ml of 1-propanol for 4.5 hours. The nickel was filtered off and the filtrate evaporated in vacuo to dryness: 4.90 g (97.2%) of crude purine, which was dissolved in 20 ml of chloroform, extracted with 1N NaOH and filtered through 30 g of silicagel in a column. The solvent was evaporated, the residue dissolved in 25 ml of methanol, treated with 11 ml of methanolic 1N HCl solution and evaporated to dryness. The residue was suspended in 80 ml of ethyl acetate and collected: 3.49 g (63.6%) of 3H-purine hydrochloride with mp 202–12° C.

| Elemental analysis for $C_{23}H_{32}ClN_5O_2$ | | | |
|---|---|---|---|
| Calc. | C 61.94 | H 7.23 | N 15.70 | O 7.17 |
| Found | C 62.17 | H 7.02 | N 15.66 | O 7.30 |

EXAMPLE 6

3-(3-Cyclopentyloxy-4-methoxybenzyl)-6-ethylamino-3H-purine Hydrochloride (i) 3-(3-Cyclopentyloxy-4-methoxy-benzyl)-2-thioxanthine 14.62 g (40 mmoles) of 1-(3-cyclopentyloxy-4-methoxy-benzyl)-5,6-diamino-2-thiouracil were dissolved in 200 ml of formic acid. The solution was concentrated in vacuo at room temperature to remove the water. 50 ml of formic acid were added and the procedure repeated. After a total of 1 hour the formic acid solution was concentrated to 30 ml at 25° and diluted with 300 ml of water. The crystals were collected, washed, and dried: 13.48 g (86.3%) of crude 5-formamide (mp 210–30° C.), which was refluxed in 86 ml of 1N NaOH for 15 min. The turbid solution was treated twice with 0.6 g of charcoal, filtered, acidified with 5N HCl to pH 2, and neutralized to pH 6.5. The amorphous solid was collected, washed, and dried at 60° C.: 11.93 g (80.1%) of crude 2-thioxanthine, which was dissolved in 150 ml of THF, treated with charcoal (5%), filtered, concentrated to 40 ml, and diluted with 250 ml of ethanol. After concentration to 120 ml the formed solid is collected, washed, and dried: 9.21 g (61.9%) of 2-thioxanthine with mp 254–65° C.

| Elemental analysis for $C_{18}H_{20}N_4O_3S$ | | | |
|---|---|---|---|
| Calc. | C 58.05 | H 5.41 | N 15.04 | O 12.89 |
| Found | C 58.13 | H 5.41 | N 14.93 | O 13.11 |

(ii) 3-(3-Cyclopentyloxy-4-methoxy-benzyl)-2,6-dithioxanthine 8.94 g (24 mmoles) of 2-thioxanthine and 6.40 g (28.8 mmoles) of phosphorus pentasulfide were refluxed in 96 ml of pyridine under nitrogen for 1.5 hours. At 5–10° C. 31.7 ml (63.4 mmoles) of 2N NaOH were added under cooling and the mixture diluted with 30 ml of pyridine. The solid was filtered off and the filtrate evaporated in vacuo to dryness. The residue was suspended in 30 ml of water and the solid collected, dissolved in 160 ml of 0.5N NaOH, filtered, treated with charcoal (20%), filtered again, acidified with 5N HCl to pH 5, the solid collected, washed, and dried: 9.03 g (96.9%) of crude dithioxanthine. The product was dissolved in 400 ml of chloroform and filtered through 30 g of silicagel in a column. The solvent was removed in vacuo, the residue dissolved in 50 ml of THF, filtered, concentrated to 30 ml, diluted with 200 ml of ethanol, concentrated again to 150 ml and the solid collected, washed, and dried: 8.65 g (92.8%) of dithioxanthine with mp 215–8° C.

| Elemental analysis for $C_{18}H_{20}N_4O_2S_2$ with 0.25M of ethanol and 0.5M of water | | | | |
|---|---|---|---|---|
| Calc. | C 54.32 | H 5.54 | N 13.70 | O 10.76 |
| Found | C 54.67 | H 5.32 | N 13.80 | O 10.20 |

(iii) 3-(3-Cyclopentyloxy-4-methoxy-benzyl)-3,7-dihydro-6-ethylamino-2H-purine-2-thione 4.66 g (12 mmoles) of dithioxanthine and 48.3 ml (60 mmoles) of 70% ethylamine in water were heated to 150° C. in a 450 ml pressure reactor under $N_2$ for 12 hours (240 psi). The solution was treated with charcoal (5%), filtered and evaporated to dryness. The residue was taken up in 100 ml of water, acidified with 1N HCl to pH 3 and neutralized with sodium bicarbonate to pH 7, and the solid collected: 4.43 g (92.5%) of crude thioisoguanine with mp 99–103° C.

(iv) 3-(Cyclopentyloxy-4-methoxy-benzyl)-6-ethylamino-3H-purine Hydrochloride 4.39 g (11 mmoles) of thioisoguanine and 7.10 g (121 mmoles) of neutral Raney-nickel are refluxed in 50 ml of 1-propanol for 4.5 hours. The nickel was filtered off and the filtrate evaporated to dryness. The residue (3.79 g/93.8%) was dissolved in 20 ml of chloroform and 0.4 ml methanol and filtered through 24 g of silicagel in a column also with 2% methanol. The combined fractions were washed with 1N NaOH and the organic phase evaporated to dryness. The residue (2.69 g/66.6%) was dissolved in 30 ml of dichloromethane and 0.6 ml methanol and again filtered through 30 g of silicagel. A total of 1.86 g (46.0%) of 3H-purine was isolated, which was dissolved in 20 ml of methanol, treated with 5.4 ml of 1N methanolic HCl, and evaporated in vacuo to dryness. Crystallization and recrystallization from dichloromethane and ethyl acetate gave 1.75 g (39.4%) of 3H-purine hydrochloride with mp 170–85° C.

| Elemental analysis for $C_{20}H_{26}C_1N_5O_2$ | | | | |
|---|---|---|---|---|
| Calc. | C 59.47 | H 6.49 | N 17.34 | O 7.92 |
| Found | C 59.72 | H 6.44 | N 17.25 | O 8.24 |

EXAMPLE 7

8-Cyclopropyl-6-(4-pyridylmethyl-amino)-3-propyl-3H-purine Dihydrochloride (i) 8-Cyclopropyl-3-propyl-2,6-dithioxanthine In a 5 L 3-necked flask fitted with a mechanical stirrer and a condenser with a drying tube were placed 2.2 L of pyridine and 8-cyclopropyl-3-propyl-2-thio-xanthine (220 g, 0.88 mol). Phosphorus pentasulfide (236 g, 1.06 mol) was added and the mixture was heated under reflux for 5 hours and stored overnight at room temperature. The reaction mixture was cooled to 5–10° and 3 N aqueous sodium hydroxide (770 ml) was added over 1.5 hours with stirring. Stirring was continued for 30 minutes after removal of the cooling bath and the precipitated product was collected by suction filtration. The filter cake was washed successively with pyridine (300 ml) and four 300 ml portions of tetrahydrofuran. The solvents are evaporated in vacuo and the solid residue was stirred with water (750 ml), filtered and washed with water. The crude product was dissolved in 1.7 L of 1 N sodium hydroxide and stirred with 15 g of Darco G-60. The charcoal was filtered and the treatment was repeated with a fresh portion of charcoal. The solution was acidified to pH 1.5 with 6 N hydrochloric acid and the pale yellow precipitate was collected. The solid was dissolved again in 1.7 L of 1N sodium hydroxide and treated successively with two portions of charcoal as above. The solution was acidified and the precipitate was collected and washed with water. After drying to constant weight at 54° C. under vacuum, there was obtained 128 g (56%) of the title compound, mp over 245° C.

(ii) 8-Cyclopropyl-3,7-dihydro-3-propyl-6-(4-pyridylmethylamino)-2H-purine-2-thione 5.33 g (20 mmoles) of 8-cyclopropyl-3-n-propyl-2,6-dithioxanthine and 21.3 ml (200 mmoles) of 95% 4-picolylamine were heated under argon to 150–5° C. After 14 hours the cooled solution was poured into 100 ml of water, acidified with 19 ml of 10N HCl and 1N HCl to pH 6, where an orange colored gum was formed. With sodium bicarbonate the mixture was neutralized to pH 7. With time the gum crystallized and the solid is collected and washed. The residue was suspended in acetone and the crystals collected: 3.92 (57.6%) of crude product. The filtrate was evaporated to dryness, dissolved in 40 ml of 0.5N NaOH, extracted 4 times with methylenechloride, and acidified again with 5N HCl to pH 6. Again the gum crystallized over 48 hours and the mixture was neutralized to pH 7 with bicarbonate and the solid collected: 1.75 g (25.7%) of crude product. Both parts were dissolved in 30 ml of methylenechloride and filtered through 30 g of silicagel in a column. 150 mg (2.8%) of starting material was recovered first, then 5.04 g (74.0%) of product was recovered with 5% of methanol, which was dissolved in 32 ml of 1N HCl, treated with 250 mg of charcoal, filtered, and neutralized with 7.5 ml of 2N NaOH and sodium bicarbonate solution to pH 7–8. The water phase was decanted from the gum and the latter washed with water and crystallized from acetone: 4.08 g (59.9%) of thioisoguanine with mp 204–210° C. with decomposition.

(iii) 8-Cyclopropyl-6-(4-pyridylmethylamino)-3-propyl-3H-purine Dihydrochloride 3.06 g (9 mmoles) of thioisoguanine and 5.8 g of neutral Raney-nickel were refluxed under argon in 1-propanol for 4 hours. The nickel was filtered off and washed with methanol. The filtrate as evaporated to dryness, the residue dissolved in 20 ml of methylenechloride, the solution extracted with 1N NaOH, and evaporated to dryness: 2.43 g (87.4%) of crude purine, which was dissolved in 20 ml of methanol, treated with 17 ml of 1N methanolic HCl and evaporated again to dryness. Crystallization from isopropanol gives 1.09 g (36.3%) of purine dihydrochloride with mp 157–65° C.

EXAMPLE 8

6-Cyclopentylamino-8-cyclopropyl-3-propyl-3H-purine Hydrochloride (i) 6-Cyclopentylamino-8-cyclopropyl-3,7-dihydro-3-propyl-2H-purine-2-thione 5.33 g (20 mmoles) of 8-cyclopropyl-3-n-propyl-2,6-dithioxantine and 42 ml of cyclopentylamine were heated in a 450 ml pressure reactor to 150° C. (50 psi) with the exclusion of air. After 20 hours the solution was transferred with methanol to a round bottom flask and evaporated in vacuo to dryness. The residue is treated with 60 ml of water and 5N HCl to obtain a pH of 2. The suspension is neutralized with bicarbonate to pH 7, the solid collected, washed, dried, suspended in refluxing acetone and collected again: 5.98 g of thioisoguanine with mp 274–6° C. (decomp).

(ii) 6-Cyclopentylamino-8-cyclopropyl-3-n-propyl-3H-purine Hydrochloride 4.49 g (14.1 mmoles) of thioisoguanine and 9.2 g of neutral Raney-nickel were refluxed in 45 ml of 1-propanol for 5 hours. The nickel was filtered off and the filtrate evaporated to dryness. The residue (>100%) was dissolved in 30 ml of methanol, treated with 16.9 ml of 1N methanolic HCl solution, and evaporated to dryness. The residue was dissolved in methylenechloride, treated with 0.12 g of charcoal, filtered, concentrated, diluted with acetone and the remaining methylene chloride removed by distillation. The crystals were collected: 4.18 g (92.3%) of purine hydrochloride with mp 218–221° C.

| Elemental analysis for $C_{16}H_{24}ClN_5$ M.W. 321.86 | | | | |
|---|---|---|---|---|
| Calc. | C 59.71 | H 7.52 | N 21.76 | Cl 11.01 |
| Found | C 59.82 | H 7.40 | N 21.76 | Cl 11.02 (diff) |

EXAMPLE 9

6-Amino-8-(1-benzyloxy-1-methyl-ethyl)-3-(3-cyclopentyloxy-4-methoxy-benzyl)-3H-purine Hydrochloride A. 6-Amino-5-(2-benzyloxy-2-methyl-propionylamino)-1-(3-cyclopentyloxy-4-methoxy-benzyl)-2-thiouracil A solution with 26.39 g (124 mM) of 2-benzyloxy-2-methyl-propionyl chloride in 86 ml of THF was added at 5–10° C. within 20 min to a stirred suspension with, 31.99 g (84.4 mM) of 1-(3-cyclopentyloxy-4-methoxy-benzyl)-4,5-diamino-2-thiouracil in 315 ml of THF and 26.5 ml of triethylamine. After 2 hr at rt the solid was filtered off and the solution evaporated to dryness. The residue was treated with 400 ml of ether, 50 ml of saturated sodium bicarbonate solution and 100 ml of water. After 2 hr the crystals were collected and washed with ether and water: 30.14 g (66.3%) of amide. The ether phase was evaporated to dryness and the residue crystallized from methanol: 5.30 g (11.7%) of amide with mp 198–202° C.

B. 8-(1-Benzyloxy-1-methyl-ethyl)-3-(3-cyclopentyloxy-4-methoxy-benzyl)-2-thioxanthine 35.44 g (65.8 mM) of the above amide (A.) were added at 70° C. to a solution with 29.53 g of t-BuOK in 350 ml of isopropanol and refluxed for 0.5 hr. The solvent was evaporated in vacuo, the residue dissolved in 350 ml of water, the solution treated twice with 3.0 g of charcoal and filtered. At 5° C. the solution was neutralized with 56 ml of 5n HCl to pH 7. After 2.5 hr the solid was collected and suspended for 1.5 hr in 300 ml of methanol, cooled to 5° C. and the solid collected again: 21.15 g (61.7%) of xanthine. The filtrate was evaporated in vacuo, the residue dissolved in dichloromethane and filtered through 60 g of silicagel in a column: crystallization from methanol gave another 5.75 g (16.8%) of xanthine with mp 158–160/235–237/288–290° C.

C. 8-(1-Benzyloxy-1methyl-ethyl)-3-(3-cyclopentyloxy-4-methoxy-benzyl)-hypoxanthine A solution with 22.39 g (43 mM) of the above xanthine (B.) in 580 ml of 1-propanol was treated with 25 g of Raney-nickel (washed with 0.1% aqueous acetic acid) and refluxed for 2 hr. The nickel was filtered off and the solvent evaporated in vacuo. The residue was crystallized from 120 ml of methanol: 12.73 g (60.6%) of hypoxanthine with mp 161–162° C., a second crop gave 1.97 g (9.4%) of hypoxanthine.

D. 6-Amino-8-(1-benzyloxy-1-methyl-ethyl)-3-(3-cyclopentyloxy-4-methoxy-benzyl)-3-H-purine Hydrochloride 2.44 g (5 mM) of the above hypoxanthine (C.) and 25 ml of phosphorus oxychloride were heated at 65–70° C. for 35 min. The solution was evaporated in vacuo and repeated twice with toluene. The residue was dissolved in 55 ml of THF and added to 3.3 ml of 32% aqueous ammonia solution. After the transfer to a 450 ml pressure reactor and a supplement of 50 g of liquid ammonia the mixture was heated to 60° C. (340 psi) for 3.5 hr. The solid was filtered off and the solvent evaporated in vacuo. The residue was dissolved in chloroform and extracted with 1 n NaOH solution. The chloroform residue was dissolved in 25 ml of methanol and treated with 5 ml of 1 m methanolic HCl solution. The solvents were evaporated in vacuo and the residue was suspended in hot methanol and the solid collected at 5° C.: 2.07 g (79.0%) of adenine with mp 201–203° C., from acetone a second crop of 0.28 g (10.7%) was collected.

Elemental analyses for $C_{28}H_{34}ClN_5O_3$/524.06;

| % calc | C 64.17 | H 6.54 | N 13.36 | O 9.16 |
|---|---|---|---|---|
| % found | C 64.13 | H 6.58 | N 13.31 | O 9.15 |

EXAMPLE 10

8-(1-Benzyloxy-1-methyl-ethyl)-3-(3-cyclopentyloxy-4-methoxy-benzyl)-6-ethylamino-3H-purine Hydrochloride 1.95 g (4 mM) of 8-(1-benzyloxy-1-methyl-ethyl)-3-(3-cyclopentyloxy-4-methoxy-benzyl)-hypoxanthine and 20 ml of phophorus oxychloride were heated to 70° C. for 0.5 hr. The solution was evaporated in vacuo and repeated twice with toluene. The residue was dissolved in 30 ml of THF and added to 16 ml of 70% aqueous ethylamine solution at 5° C. After 1 hr at rt the solvents were evaporated in vacuo. The residue was dissolved in 50 ml of dichloromethane and extracted with 1 n NaOH solution. The organic phase was evaporated in vacuo, the residue dissolved in 20 ml of methanol, treated with 4.4 ml of 1 m methanolic HCl solution and evaporated again. The residue was crystallized from ethyl acetate: 1.85 g (83.7%) of adenine with mp 148–150° C. From ethyl acetate-ether a second crop of 0.17 g (7.7%) was obtained.

Elemental analyses for $C_{30}H_{28}ClN_5O_3/552.12$;

| % calc | C 65.26 | H 6.94 | N 12.68 | O 8.69 |
|---|---|---|---|---|
| % found | C 65.07 | H 6.95 | N 12.53 | O 8.96 |

EXAMPLE 11

6-Amino-3-(3,4-methylenedioxy-benzyl)-8-(1-(4-fluorobenzyloxy)-1-methyl-ethyl)-3H-purine Hydrochloride

A. 6-Amino-1-(3,4-dimethoxy-benzyl)5-(2-(4-fluorobenzyloxy-2-methyl-propionylamino)-2-thiouracil A solution with 3.70 g (15 mM) of 2-(4-fluorobenzyloxy)-2-methyl-propionyl chloride in 10 ml of THF was added at 0–5° C. within 5 min to a suspension with 3.19 g (10.3 mM) of 5,6-diamino-1-(3,4-dimethoxybenzyl)-2-thiouracil and 3.5 ml of (25 mM) of triethylamine in 30 ml of THF. After 4 hr the solid was filtered off and the solvent evaporated in vacuo. The residue was dissolved in 40 ml of ethyl acetate and extracted with 20 ml of 1 n HCl solution. A precipitate was formed and collected: 2.11 g (40.6%) of amide. The ethyl acetate phase was washed with sodium bicarbonate solution and evaporated to dryness: 3.70 g of a mainly two compound mixture. Separation of a dichloromethane solution, comprising 2% of methanol, on 60 g of silicagel in a column gave first after crystallization from acetone 1.11 g (15.4%) of the diamide with mp 194–197° C. and later fractions gave 1.06 g (20.4%) of amide with mp 110–180° C. as a second crop.

B. 3-(3,4-Dimethoxybenzyl)-8-(1-(4-fluorobenzyloxy-1-methyl-ethyl)-2-thioxanthine A solution with 3.07 g (6.1 mM) of the above amide (A.) in 30 ml of 1 n NaOH was refluxed for 15 min, treated twice with 0.2 of charcoal, filtered and neutralized with 6.2 ml of 5 n HCl. The solid was collected, suspended in 30 ml of hot methanol and collected again at 5° C.: 2.34 g (79.1%) of xanthine with mp 300–302° C.

C. 3-(3,4-Dimethoxybenzyl)-8-(1-(4-fluorobenzyloxy)-1-methyl-ethyl)-hypoxanthine 2.18 g (4.5 mM) of xanthine (B.) and 2.6 g of Raney-nickel (treated with 0.1% aqueous acetic acid) were refluxed in 30 ml of 1-propanol for 2.5 hr. The nickel was filtered off and the solution evaporated in vacuo to dryness. The residue was dissolved in 40 ml of ethyl acetate and extracted with sodium bicarbonate solution. The formed solid is filtered off and the organic phase evaporated in vacuo to dryness (1.95 g). A dichloromethane solution, comprising 2% of methanol, was purified on 19 g of silicagel in a column. Crystallization from ethyl acetate gave 1.37 g (67.2%) of hypoxanthine with mp 159–161° C., a second crop gave 0.4 g (2.0%) of hypoxanthine.

D. 6-Amino-3-(3,4-dimethoxybenzyl)-8-(1-(4-fluorobenzyloxy-1-methyl-ethyl)-3H-purine Hydrochloride 1.27 g (2.8 mM) of the above hypoxanthine (C.) was heated in 13 ml of phosphorus oxychloride to 70° C. for 30 min. Evaporation in vacuo and twice repetition with toluene gave the crude 6-chloro intermediate, which was dissolved in 40 ml of THF and added at 0–5° C. to 12 ml of 32% aqueous ammonia. After the addition of 50 g of liquid ammonia the solution was heated to 60° C. in a 450 ml pressure reactor (340 psi). After 3.5 hr the solid was filtered off and the solution evaporated in vacuo to dryness. The residue was dissolved in dichloromethane, extracted with 1 n NaOH and evaporated again to dryness. The residue was dissolved in 20 ml of methanol, treated with 2.9 ml of 1 m methanolic HCl and evaporated to dryness. Crystallization from ethyl acetate gave 1.24 g (90.5%) of title adenine with mp 172–175° C.

Elemental analyses for $C_{24}H_{27}ClFN_5O_3/487.96$;

| % calc | C 59.07 | H 5.58 | N 14.35 | O 9.84 |
|---|---|---|---|---|
| % found | C 58.95 | H 5.75 | N 14.24 | O 10.10 |

EXAMPLE 12

6-Amino-3-(3-cyclopentyloxy-4-methoxy-benzyl)8-(1-(4-methoxybenzyloxy)-1-methyl-ethyl)-3H-purine Hydrochloride

A. 6-Amino-1-(3-cyclopentyloxy-4-methoxy-benzyl)-5-(2-(4-methoxybenzyloxy)-2-methyl-propionylamino)-2-thiouracil A solution with 2.91 g (12 mM) of crude 2-(4-methoxybenzyloxy)-2-methyl-propionyl chloride in 9 ml of THF was added within 90 min to a stirred suspension with 3.62 g (10 mM) of 5,6-diamino-1-(3-cyclopentyloxy-4-methoxy-benzyl)-2-thiouracil. After 20 hr another 485 mg of chloride in 5 ml of THF was added within 30 min. After a further 3 hr the solid was filtered off and the solution evaporated in vacuo to dryness. The residue was dissolved in ethyl acetate, extracted with sodium bicarbonate solution and the organic phase evaporated in vacuo to dryness. The residue was crystallized from methanol: 1.71 g (30.1%) of amide with mp 172–184° C.

B. 3-(3-Cyclopentyloxy-4-methoxy-benzyl)-8-(1-(4-methoxybenzyloxy)-1-methyl-ethyl)-2-thioxanthine 3.30 g (5.8 mM) of the above amide (A.) and 2.60 g of t-BuOK (23 mM) were refluxed in 33 ml of isopropanol for 45 min. The solvent was removed in vacuo, the residue dissolved in 50 ml of water, treated twice with 0.3 g of charcoal, filtered, acidified with 4.5 ml of 5 n HCl to pH 4.5and neutralized with sodium bicarbonate solution. The solid was collected and crystallized from methanol: 2.48 g (77.7%) of xanthine with mp 169/276–279° C.

C. 3-(3-Cyclopentyloxy-4-methoxy-benzyl)-8-(1-(4-methoxybenzaloxy)-1-methyl-ethyl)-hypoxanthine A solution with 2.34 g (4.25 mM) of the above xanthine (B.) and 2.5 g of Raney-nickel (treated with 0.1% of aqueous acetic acid) were refluxed in 35 ml of 1-propanol. After 2.5 hr the nickel was filtered off and the solvent evaporated in vacuo. The residue was dissolved in ethyl acetate, extracted with sodium bicarbonate solution and concentrated in vacuo to about 10 ml. Over night crystallization gave 1.29 g (58.6%) of hypoxanthine with mp 156–157° C.

D. 6-Amino-3-(3-cyclopentyloxy-4-methoxy-benzyl)-8-(1-(4-methoxybenzyloxy)-1-methyl-ethyl)-3H-purine-hydrochloride 1.14 g (2.2 mM) of the above hypoxanthine (C.) and 12 ml of phosphorus oxychloride were heated to 70° C. for 40 min. Evaporation in vacuo and repetition twice with toluene gave the crude 6-chloro derivative which was dissolved in 40 ml of THF and added to 12 ml of 32% aqueous ammonia solution. After supplemented with 50 g of liquid ammonia the solution was heated to 60° C. in a 450 ml pressure reactor (340 psi) for 3.5 hr. The solvent was evaporated in vacuo, the residue dissolved in chloroform, the solution extracted with 1 n NaOH and evaporated in vacuo to dryness. The residue was dissolved iri methanol treated with 2.3 ml of 1 m methanolic HCl and evaporated in vacuo to dryness. The residue was crystallized from acetone and suspended in water-ether.

EXAMPLE 13

6-Amino-3-(3-cyclopentyloxy-4-methoxy-benzyl)-8-(1-(4-pyridylmethoxy)-1-methyl-ethyl)-3H-purine dihydrochloride A. 6-Amino-1-(3-cyclopentyloxy-4-methoxy-benzyl)-5-(2-(4pyridylmethoxy)-2-methyl-propionylamino-2-thio-uracil 3.58 g (14.3 mM) of 2-(4-pyridylmethoxy-2-methyl-propionyl chloride hydrochloride were added to a solution of 3.61 g (10 mM) of 1-(3-cyclopentyloxy-4-methoxy-benzyl)-5,6-diamino-2-thiouracil in 82 ml of pyridine. After 48 hr the solution was heated to 50° C. for 3 hr. 4.15 g (30 mM) of potassium carbonate were added and after an additional 24 hr of stirring the solid was filtered off and the solution evaporated in vacuo to dryness. The residue was suspended in 50 ml of water and 10 ml of THF. The crystals were collected suspended in 50 ml of hot acetone and concentrated. The solid was collected at 0–5° C.: 3.34 g (61.9%) of amide with mp 245–247° C.

B. 3-(3-Cyclopentyloxy-4-methoxy-benzyl)-8-(1-(4-pyridylmethoxy)-1-methyl-ethyl)-2-thioxanthine 3.24 g (6 mM) of the above amide (A.) were refluxed for 40 min in a solution of 2.78 g (24 niM) of t-BuOK in 32 ml of isopropanol. The solution was evaporated in vacuo to dryness, the residue dissolved in 50 ml of water, the solution treated twice with 0.3 g of charcoal, filtered and neutralized with 4.5 ml of 5 n HCl. The solid was collected, suspended in 40 ml of hot methanol, concentrated to 20 ml and collected again at 0–5° C.: 2.40 g (76.7%) of xanthine with mp 210–213/286–288° C.

C. 3-(3-Cyclopentyloxy-4-methoxy-benzyl)-8-(1-(4-pyridylmethoxy)-1-methyl-ethyl)-hypoxanthine 2.19 g (4.2 mM) of the above xanthine (B.) were refluxed with 2.5 g of Raney-nickel (treated with 0.1% of aqueous acetic acid) in 30 ml of 1-propanol for 2.5 hr. The nickel was filtered off and the solution evaporated in vacuo to dryness. The residue was dissolved in in 40 ml of dichloromethane, the solution extracted with sodium bicarbonate solution and the organic phase evaporated in vacuo to dryness. The residue was dissolved in a 19:1 mixture of dichloromethane and methanol, filtered through 30 g of silicagel in a column and evaporated again to dryness: 1.48 g (71.8%) of crude hypoxanthine.

D. 6-Amino-3-(3-cyclopentyloxy-4-methoxy-benzyl)-8-(1-(4-pyridylmethoxy)-1-methyl-ethyl)-3H-purine-dihydrochloride 1.48 g (3.0 mM) of the above crude hypoxanthine (C.) and 15 ml of phosphorus oxychloride were heated to 65–70° C. for 40 min. The solution turned purple immediately and was evaporated in vacuo to dryness and repeated twice with toluene. The crude chloride was dissolved in 40 ml of THF and 12 ml of 32% aqueous ammonia. After the transfer to a 450 ml pressure reactor supplemented with 50 g of liquid ammonia and heated to 60° C. for 4 hr (340 psi). The mixture was evaporated in vacuo to dryness. The residue was dissolved in chloroform, the solution extracted with In NaOH solution and the organic phase evaporated in vacuo to dryness. The residue was dissolved in a 19:1 mixture of dichloromethane and methanol and chromatographed on 30 g of silicagel in a column.

EXAMPLE 14

6-Amino-8-(1-benzyloxy-1-methyl-ethyl)-3-(34-dimethoxybenzyl)-3H-purine Hydrochloride In analogy to example 9 we prepared from 5,6-diamino-1-(3,4-dimethoxybezyl)-2-thiouracil and 2-benzyloxy-2-methyl-propionyl chloride the following compounds:
  A. 6-Amino-5-(2-benzyloxy-2-methyl-propionylamino)-1-(3,4-dimethoxybenzyl)-2-thiouracil
  B. 8-(1-Benzyloxy-1-methyl-ethyl)-3-(3,4-dimethoxybenzyl)-2-thioxanthine
  C. 8-(1-Benzyloxy-1-methyl-ethyl)-3-(3,4-dimethoxybenzyl)-hypoxanthine with mp 164–166° C.
  D. 6-Amino-8-(1-benzyloxy-1-methyl-ethyl)-3-(3,4-dimethoxybenzyl)-3H-purine hydrocloride
with mp 184/190–191° C.; Elemental analyses for $C_{24}H_{28}ClN_5O_3$;

| | | | | |
|---|---|---|---|---|
| % calc | C 61.34 | H 6.01 | N 14.90 | O 10.21 |
| % found | C 61.30 | H 6.15 | N 14.89 | O 10.28 |

EXAMPLE 15

6-Amino-3-(3-cyclopentyloxy-4-methoxy-benzyl)-8-(1-(4-fluorobenzyloxy)-1-methyl-ethyl)-3H-purine hydrochloride In analogy to example 9 we prepared from 1-(3-cyclopentyloxy-4-methoxy-benzyl)-4,5-diarmino-2-thiouracil and 2-(4-fluorobenzyloxy)-2-methyl-propionyl chloride the following compounds:
  A. 6-Amino-1-(3-cyclopentyloxy-4-methoxy-benzyl)-5-(2-(4-fluorobenzyloxy)-2-methyl-propionylamino)-2-thiouracil with mp 185–193° C.
  B. 3-(3-Cyclopentyloxy-4-methoxy-benzyl)-8-(1-(4-fluorobenzyloxy)-1-methyl-ethyl)-2-thioxanthine with mp 188–192/288–296° C.
  C. 3-(3-Cyclopentyloxy-4-methoxy-benzyl)-8-(1-(4-fluorobenzyloxy)-1-methyl-ethyl)-hypoxanthine with mp 131–134° C.
  D. 6-Amino-3-(3-cyclopentyloxy-4-methoxy-benzyl)-8-(1-(4-fluorobenzyloxy)-1-methyl-ethyl)-3H-purine hydrochloride with mp 165–174° C.

EXAMPLE 16

8-Benzyloxymethyl-3-(3-cyclopentyloxy-4-methoxy-benzyl)-6-ethylamino-3H-purine hydrochloride In analogy to example 9 we prepared from benzyloxy-acetyl chloride and 1-(3-cyclopentyloxy-4-methoxy-benzyl)-4,5-diamino-2-thiouracil the following compounds:

A. 6-Amino-5-benzyloxyacetylamino-2-thiouracil with mp 195–196° C.

B. 8-Benzyloxymethyl-3-(3-cyclopentyloxy-4-methoxybenzyl)-2-thioxanthine with mp 101–103° C.

C. 8-Benzyloxymethyl-3-(3-cyclopentyloxy-4-methoxybenzyl)-hypoxanthine with mp 190–194° C.

D. 8-Benzyloxymethyl-3-(3-cyclopentyloxy-4-methoxybenzyl)-6-ethylamino-3H-purine hydrochloride with mp 179/196–198° C.

Elemental analyses for $C_{28}H_{34}ClN_5O_3/524.06$;

| | | | | |
|---|---|---|---|---|
| % calc | C 64.17 | H 6.54 | N 13.36 | O 9.16 |
| % found | C 63.91 | H 6.62 | N 13.39 | O 9.14 |

EXAMPLE 17

Thioisoguanine Derivatives

Following the previously set forth methods, the following thioisoguanine derivatives of the present invention were synthesized. The chemical name and melting point are provided in Table 1 below.

TABLE 1

THIOISOGUANINES

| Compouud | m.p. (° C.) |
|---|---|
| 3,8-diethyl-3,7-dihydro-6-morpholino-2H-2-thio-purin-2-one | 295–298(dec) |
| 3-(cyclopropylmethyl)-3,7-dihydro-8-isopropyl-6-propylamino-2-thio-2H-purin-2-one | 208–210 |
| 3,7-dihydro-6-ethylamino-3-hexyl-2-thio-2H-purin-2-one | 235–237 |
| 3,7-Dihydro-3-hexyl-6-methylamino-2-thio-2H-purin-2-one | 217–219 |
| 3-benzyl-3,7-dihydro-6-methylamino-2-thio-2H-purin-2-one | 253–255 |
| 8-cyclopropyl-3,7-dihydro-6-ethylamino-3-(3-methylbutyl)-2-thio-2H-purin-2-one | 250–254 |
| 8-cyclopropyl-3,7-dihydro-3-ethyl-6-propylamino-2-thio-2H-purin-2-one | 270–272 |
| 3-butyl-3,7-dihydro-6-ethylamino-2-thio-2H-purin-2-one | (220) 246–248 |
| 3-butyl-8-cyclopropyl-3,7-dihydro-6-ethylamino-2-thio-2H-purin-2-one | 226–228 |
| 6-ethylamino-3,7-dihydro-3-propyl-2-thio-2H-purin-2-one | 247–251 |
| 8-cyclopropyl-6-ethylamino-3,7-dihydro-3-propyl-2-thio-2H-purin-2-one | 238–239 |
| 8-cyclopropyl-3-cyclopropylmethyl-6-ethylamino-3,7-dihydro-2-thio-2H-purin-2-one | 247–249 |
| 3-benzyl-6-ethylamino-3,7-dihydro-2-thio-2H-purin-2-one | 254–257 |
| 8-cyclopropyl-6-cyclopropylamino-3-propyl-3,7-dihydro-2-thio-2H-purin-2-one hydrochloride | 208–226 dec |
| 3-((2-methyl)butyl))-6-(2-(piperazine-1-yl)ethylamino)-3,7-dihydro-2-thio-2H-purin-2-one | |
| 3-cyclohexylmethyl-3,7-dihydro-6-ethylamino-2-thio-2H-purin-2-one | 295–300 |
| 3-benzyl-6-ethylamino-3,7-dihydro-8-(1-methylethyl)-2-thio-2H-purin-2-one | |
| 3-cyclohexylmethyl-8-cyclopropyl-3,7-dihydro-6-ethylamino-2-thio-2H-purin-2-one | 278–282 |
| 6-benzylamino-8-(cyclopropyl)-3,7-dihydro-3-propyl-2-thio-2H-purin-2-one hydrochloride | 180–185 |
| 8-(cyclopropyl)-3,7-dihydro-6-hexylamino-3-(propyl)-2-thio-2H-purin-2-one hydrochloride | 170–190 |
| 6-butylamino-8-cyclopropyl-3,7-dihydro-3-propyl-2H-purin-2-one | 231–233 |
| 6-cyclopropyl-3,7-dihydro-6-(2-hydroxyethylamino)-2-thio-2H-purin-2-one | 188–192 |

TABLE 1-continued

THIOISOGUANINES

| Compouud | m.p. (° C.) |
|---|---|
| 6-amino-8-cyclopropyl-3,7-dihydro-3-propyl-2-thio-2H-purin-2-one | 220–265 |
| 6-cyclopentylamino-3-ethyl-3,7-dihydro-8-isopropyl-2-thio-2H-purin-2-one | 301–304 |
| 6-cyclohexylamino-3,7-dihydro-8-isopropyl-3-propyl-2-thio-2H-purin-2-one | 303 dec |
| 6-cyclopentylamino-3,7-dihydro-8-isopropyl-3-propyl-2-thio-2H-purin-2-one | 295 dec |
| 6-cyclopentylamino-3-ethyl-8-cyclopropyl-3,7-dihydro-2-thio-2H-purin-2-one | 245 dec |
| 3-(4-chlorobenzyl)-6-cyclopentylamino-3,7-dihydro-8-isopropyl-2-thio-2H-purin-2-one | 244–248 |
| 6-cyclopentylamino-3-(3-cyclopentyl-4-methoxybenzyl)-3,7-dihydro-8-isopropyl-2-thio-2H-purin-2-one | 230–235 |
| 3-(2-chlorobenzyl)-6-cyclopentylamino-3,7-dihydro-8-isopropyl-2-thio-purin-2-one | |
| 8-cyclopropyl-3,7-dihydro-6-(3-pentyl)-3-propyl-2-thio-2H-purin-2-one | 220 dec |
| 6-ethyl-8-isopropyl-3,7-dihydro-3-(4-pyridylmethyl)-2-thio-2H-purin-2-one | 238–40 |

EXAMPLE 18

Elemental Analysis of Thiosoguanine Derivates

A. Elemental analysis for 6-butylamino-8-cyclo-propyl-3,7-dihydro-3-propyl-2H-purine-2-thione:

| | | | |
|---|---|---|---|
| Calc. | C 58.98 | H 7.59 | N 22.93 |
| Found | C 58.99 | H 7.52 | N 22.92 |

B. 3-(cyclopropylmethyl)-3,7-dihydro-8-isopropyl-6-propylamino-2H-purine-2-thione;

Melting point: 208–210° C.;

Elemental analysis:

| | | | |
|---|---|---|---|
| Calc. | C 62.26 | H 8.01 | N 24.20 |
| Found | C 62.34 | H 8.06 | N 23.89 |

EXAMPLE 19

PDE IV Inhibition by Thioisoguanine Compounds

The PDE IV inhibitory activity of certain of the foregoing thioisoguanine compounds was determined according to the procedures set forth below. The results are provided in Table 2.

Type IV Phosphodiesterase

Enzyme Isolation Protocol

The Type IV PDE is isolated from bovine tracheal smooth muscle using a procedure similar to that previously described by Silver, P. J., Hamel, L. T., Perrone, M. H. Bentley, R. G. Bushover, C. R., Evans, D. B.: Eur. J. Pharmacol. 150:85,1988.(1). Briefly, smooth muscle from bovine trachea is minced and homogenized using a polytron in 10 volumes of an extraction buffer containinhg 10 mM Tris-acetate (pH 7.5), 2 mM magnesium chloride, 1 mM dithiothreitol and 2,000 units/ml of aprotinin. This and all subsequent procedures are performed at 0–4° C. The homogenate is sonicated and then centrifuged at 48,000×g for 30 minutes. The resulting supernatant is applied to a DEAE Trisacryl M column previously equilibrated with sodium acetate and dithiothreitol. After applications of the sample, the column is washed with sodium acetate/dithiothreitol, after which the different forms of PDE are eluted from the column using a linear Tris-HCl/NaCl gradient. Fractions containing Type IV PDE are collected, dialyzed and concentrated to 14% of the original volume. The concentrated fractions are diluted to 50% with ethylene glycol and stored at -20° C.

Measuring Type IV PDE Activity

Enzyme activity is assessed by measuring the hydrolysis of [$^3$H]-cyclic AMP, as described by Thompson, W. J., Teraski, W. L., Epstein, P. N., Strada, S. J.: Adv. Cyclic Nucleotide Res. 10:69, 1979. The cyclic AMP concentration used in this assay is 0.2 μM, which approximates the $K_m$ value. Protein concentration is adjusted to ensure that no more than 15% of the available substrate is hydrolyzed during the incubation period.

All test compounds are dissolved in dimethyl sulfoxide (final concentration of 2.5%). This concentration of dimethyl sulfoxide inhibits enzyme activity by approximately 10%.

TABLE 2

THIOISOGUANINES - BIOLOGICAL DATA

| Name | Calc IC50 PDE IV |
|---|---|
| 3-(cyclopropylmethyl)-3,7-dihydro-8-(1-methylethyl)-6-propylamino-2-thio-2H-purin-2-one hydrochloride | 23.95 |
| 8-cyclopropyl-3-ethyl-6-ethylamino-3,7-dihydro-2-thio-2H-purin-2-one | 13.65 |
| 8-cyclopropyl-3-ethyl-6-propylamino-2-thio-2H-purin-2-one | 8.48 |
| 3-butyl-8-cyclopropyl-3,7-dihydro-6-ethylamino-2-thio-2H-purin-2-one | 34.86 |
| 3-benzyl-6-ethylamino-3,7-dihydro-8-(1-methylethyl)-2-thio-2H-purin-2-one | 28.37 |
| 3-cyclohexylmethyl-8-cyclopropyl-3,7-dihydro-6-ethylamino-2-thio-2H-purin-2-one | 15.20 |
| 6-benzylamino-8-(cyclopropyl)-3,7-dihydro-3-propyl-2-thio-2H-purin-2-one hydrochloride | 33.60 |
| 8-cyclopropyl-3,7-dihydro-3-propyl-6-(4-pyridylmethylamino)-2-thio-2H-purin-2-one | 0.41 |
| 6-cyclopentylamino-8-cyclopropyl-3,7-dihydro-3-propyl-2-thio-2H-purin-2-one hydrochloride | 7.41 |
| 6-butylamino-8-cyclopropyl-3,7-dihydro-3-propyl-2-thio-2H-purin-2-one | 24.48 |
| 8-cyclopropyl-3,7-dihydro-6-(2-hydroxyethylamino)-3-propyl-2-thio-2H-purin-2-one | 53.80 |
| 6-amino-8-cyclopropyl-3,7-dihydro-3 propyl-2-thio-2H-purin-2-one | 39.42 |
| 3-ethyl-6-cyclopentylamino-3,7-dihydro-8-isopropyl-2-thio-2H-purin-2-one | 9.40 |
| 6-cyclopentylamino-3,7-dihydro-8-isopropyl-3-propyl-2-thio-2H-purin-2-one | 45.10 |
| 3-ethyl-6-cyclopentylamino-8-cyclopropyl-3,7-dihydro-2-thio-2H-purin-2-one | 0.19 |
| 3-(4-chlorobenzyl)-6-cyclopentylamino-3,7-dihydro-8-isopropyl-2-thio-2H-purin-2-one | 114.50 |

EXAMPLE 20

Adenine Derivates

Following the method of the above Examples, the following compounds were similarly prepared from the appropriate starting materials. All temperatures are in ° C. unless otherwise stated.

The data is provided in Table 3 below.

TABLE 3

ADENINES

| Compound | m.p. |
|---|---|
| 6-ethylamino-3-hexyl-3H-purine hydrochloride | 190–195 |
| 3-hexyl-6-methylamino-3H-purine | 142–3 |
| 8-cyclopropyl-6-ethylamino-3-(3-methylbutyl)-3H-purine hydrochloride | 188–190 |
| 8-cyclopropyl-3-ethyl-6-propylamino-3H-purine hydrochloride | 186–188 |
| 8-cyclopropyl-3-ethyl-6-methylamino-3H-purine | 143–145 |
| 3-butyl-6-ethylamino-3H-purine | 127–129 |
| 3-butyl-8-cyclopropyl-6-ethylamino-3H-purine | 182–184 |
| 6-ethylamino-3-propyl-3H-purine | 157–159 |
| 8-cyclopropyl-6-ethylamino-3-propyl-3H-purine hydrochloride | 193–195 |
| 8-cyclopropyl-3-cyclopropylmethyl-6-ethylamino-3H purine hydrochloride | 195–197 |
| 3-benzyl-6-ethylamino-3H-purine | 187–188 |
| 8-cyclopropyl-6-cyclopropylamino-3-propyl-3H-purine hydrochloride | 200–210 |
| 3-(2-methylbutyl)-6-(2-(piperazin-1-yl)ethylamino)-3H-purine | 144–145 |
| 3-cyclohexylmethyl-6-ethylamino-3H-purine | 258–265 |
| 3-benzyl-6-ethylamino-8-(1-methylethyl)-3H-purine hydrochloride | 199–200 |
| 3-cyclohexylmethyl-8-cyclopropyl-6-ethylamino-3H-purine hydrochloride | 192–193 |
| 3-cyclopropylmethyl-8-isopropyl-6-ethylamino-3H-purine | 96–99 |
| 3-ethyl-8-isopropyl-6-benzylamino-3H-purine | 141–142 |
| 3-ethyl-8-isopropyl-6-ethylamino-3H-purine hydrochloride | 194–195 |
| 3-ethyl-8-cyclopentyl-6-benzylamino-3H-purine hydrochloride | 179–182 |
| 3-ethyl-8-cyclopentyl-6-ethylamino-3H-purine hydrochloride | 212–214 |
| 3-(4-chlorobenzyl)-6-ethylamino-3H-purine | |
| 3-(4-chlorobenzyl)-6-ethylamino-3H-purine hydrochloride | 251–4 |
| 3-(4-chlorobenzyl)-6-ethylamino-8-isopropyl-3H-purine | |
| 3-(4-chlorobenzyl)-6-ethylamino-8-isopropyl-3H-purine hydrochloride | 215–7 |
| 6-benzylamino-8-cyclopropyl-3-propyl-3H-purine | 153–55 |
| 8-cyclopropyl-6-hexylamino-3-propyl-3H-purine hydrochloride | 137–8 |
| 8-cyclopropyl-3-propyl-6-(4-pyridylmethylamino)-3H-purine dihydrochloride | 185–208 |
| 6-cyclopentylamino-8-cylopropyl-3-propyl-3H-purine hydrochloride | 273–6 |
| 6-butylamino-8-cyclopropyl-3-propyl-3H-purine hydrochloride | 171–3 |
| 8-cyclopropyl-6-(2-hydroxyethylamino)-3-propyl-3H-purine | 217–9 |
| 6-(3-cyclopentyloxy-4-methoxybenzylamino)-8-cyclopropyl-3-propyl-3H-purine hydrochloride | |
| 6-amino-8-cyclopropyl-3-propyl-3H-purine | 188–90 |
| 3-ethyl-6-cyclopentylamino-8-isopropyl-3H-purine hydrochloride | 183–4 |
| 6-cyclohexylamino-8-isopropyl-3-propyl-3H-purine hydrochloride | 202–3 |
| 6-cyclopentylamino-8-isopropyl-3-propyl-3H-purine hydrochloride | 207–10 |
| 3-ethyl-6-cyclopentylamino-8-cyclopropyl-3H-purine hydrochloride | 205–8 |
| 3-(4-chlorobenzyl)-6-cyclopentylamino-8-cyclopropyl-3H-purine hydrochloride | 269–73 |
| 6-cyclopentylamino-3-(3-cyclopentyloxy-4-methoxybenzyl)-8-isopropyl-3H-purine hydrochloride | 193–5 |
| 3-(2-chlorobenzyl)-6-cyclopentylamino-8-isopropyl-3H-purine hydrochloride | 207–8 |
| 8-cyclopropyl-6-diethylamino-3-propyl-3H-purine hydrochloride | 173–9 |
| 8-cyclopropyl-6-(3-pentylamino)-3-propyl-3H-purine hydrochloride | 187–9 |

TABLE 3-continued

ADENINES

| Compound | m.p. |
|---|---|
| 6-ethylamino-8-isopropyl-3-(4-pyridylmethyl)-3H-purine dihydrochloride | 240–6 |

EXAMPLE 21

Elemental Analysis of Adenines

Elemental analysis was conducted for certain of the compounds set forth in the above tables. The results are provided below.

Elemental analysis for 8-cyclopropyl-3-ethyl-6-ethylamino-3H-purine hydrochloride 99% + 1% (H$_2$O, HCl)

| | | | |
|---|---|---|---|
| Calc. C 53.29 | H 6.80 | N 25.90 | O 0.53 |
| Found C 52.97 | H 7.01 | N 26.01 | O 0.34 |

Elemental analysis for 6-ethyl-amino-3-hexyl-3H-purine hydrochloride mp 188–94°

| | | | |
|---|---|---|---|
| Calc. C 55.02 | H 7.81 | N 24.68 | Cl 12.49 |
| Found C 55.33 | H 8.05 | N 24.50 | Cl 12.71 |

Elemental analysis for 3-hexyl-6-methylamino-3H-purine hydrochloride mp 190–195°

| | | | |
|---|---|---|---|
| Calc. C 53.43 | H 7.47 | N 25.96 | Cl 13.14 |
| Found C 53.70 | H 7.81 | N 25.92 | Cl 13.18 |

Elemental analysis for 8-cyclopropyl-6-ethyl-amino-3-(3-methylbutyl)-3H-purine hydrochloride

| | | | |
|---|---|---|---|
| Calc. C 58.15 | H 7.81 | N 22.60 | Cl 11.44 |
| Found C 58.12 | H 8.01 | N 22.65 | Cl 11.46 |

Elemental analysis for 8-cyclopropyl-3-ethyl-6-propylamino-3H-purine hydrochloride

| | | | |
|---|---|---|---|
| Calc. C 55.41 | H 7.15 | N 24.85 | Cl 12.58 |
| Found C 55.74 | H 7.06 | N 25.08 | Cl 12.71 |

Elemental analysis for 8-cyclo-propyl-3-ethyl-6-methylamino-3H-purine

| | | |
|---|---|---|
| Calc. C 60.81 | H 6.96 | N 32.23 |
| Found C 60.58 | H 7.02 | N 32.67 |

Elemental analysis for 3-butyl-6-ethylamino-3H-purine hydrochloride mp 221–223°

| | | | |
|---|---|---|---|
| Calc. C 51.65 | H 7.09 | N 27.38 | Cl 13.88 |
| Found C 51.74 | H 7.06 | N 27.62 | Cl 13.93 |

Elemental analysis for 3-butyl-8-cyclopropyl-6-ethylamino-3H-purine hydrochloride mp 194–196°

| | | | |
|---|---|---|---|
| Calc. C 56.83 | H 7.49 | N 23.67 | Cl 11.98 |
| Found C 56.91 | H 6.98 | N 23.97 | Cl 12.03 |

Elemental analysis for 6-ethyl-amino-3-propyl-3H-purine 98% + 2% water

| | | |
|---|---|---|
| Calc. C 57.35 | H 7.44 | N 33.44 |
| Found C 57.68 | H 7.22 | N 33.29 |

Elemental analysis for 8-cyclopropyl-6-ethylamino-3-propyl-3H-purine hydrochloride

| | | | |
|---|---|---|---|
| Calc. C 55.41 | H 7.15 | N 24.85 | Cl 12.58 |
| Found C 55.45 | H 7.13 | N 24.96 | Cl 12.71 |

Elemental analysis for 8-cyclopropyl-3-cyclopropylmethyl-6-ethylamino-3H-purine hydrochloride

| | | | |
|---|---|---|---|
| Calc. C 57.23 | H 6.87 | N 23.84 | Cl 12.07 |
| Found C 57.49 | H 6.88 | N 23.59 | Cl 12.49 |

Elemental analysis for 3-benzyl-6-ethylamino-3H-purine

| | | |
|---|---|---|
| Calc. C 66.39 | H 5.97 | N 27.65 |
| Found C 66.58 | H 5.63 | N 27.80 |

Elemental analysis for 8-cyclopropyl-6-cyclopropylamino-3-propyl-3H-purine hydrochloride

| | | | |
|---|---|---|---|
| Calc. C 57.23 | H 6.86 | N 23.84 | Cl 12.07 |
| Found C 57.30 | H 6.90 | N 23.77 | Cl 12.16 |

Elemental analysis for 3-cyclohexylmethyl-6-ethylamino-3H-purine hydrochloride

| | | | |
|---|---|---|---|
| Calc. C 56.84 | H 7.50 | N 23.67 | Cl 11.98 |
| Found C 56.82 | H 7.54 | N 23.65 | Cl 12.05 |

Elemental analysis for 3-benzyl-6-ethylamino-8-(1-methylethyl)-3H-purine hydrochloride

| | | | |
|---|---|---|---|
| Calc. C 61.52 | H 6.68 | N 21.10 | Cl 10.68 |
| Found C 61.52 | H 6.59 | N 21.18 | Cl 10.60 |

Elemental analysis for 3-cyclohexylmethyl-8-cyclopropyl-6-ethylamino-3H-purine hydrochloride

| | | | |
|---|---|---|---|
| Calc. C 60.79 | H 7.80 | N 20.85 | Cl 10.56 |
| Found C 60.55 | H 7.48 | N 20.85 | Cl 11.34 |

Elemental analysis for 3-cyclopropylmethyl-8-isopropyl-6-ethylamino-3H-purine

| | | |
|---|---|---|
| Calc. C 64.84 | H 8.16 | N 27.00 |
| Found C 64.42 | H 7.86 | N 26.87 |

Elemental analysis for 6-benzylamino-3-ethyl-8-isopropyl-6-ethylamino-3H-purine

| | | |
|---|---|---|
| Calc. C 69.12 | H 7.17 | N 23.71 |
| Found C 69.27 | H 7.44 | N 23.60 |

Elemental analysis for 3-ethyl-8-isopropyl-6-ethylamino-3H-purine hydrochloride

| | | |
|---|---|---|
| Calc. C 53.43 | H 7.47 | N 25.96 |
| Found C 53.62 | H 7.66 | N 25.34 |

Elemental analysis for 6-benzylamino-8-cyclopentyl-3-ethyl-3H-purine

| | | |
|---|---|---|
| Calc. C 63.78 | H 6.76 | N 19.57 |
| Found C 63.55 | H 6.54 | N 19.51 |

Elemental analysis for 8-cyclopentyl-3-ethyl-6-ethylamino-3H-purine hydrochloride

| | | |
|---|---|---|
| Calc. C 56.84 | H 7.50 | N 23.67 |
| Found C 56.54 | H 7.37 | N 23.63 |

EXAMPLE 22

PDE IV Inhibition by Adenine Compounds

The PDE IV inhibitory effect of certain of the compounds set forth above was examined according to the methods previously described. The results are provided in Table 4 below.

TABLE 4

PDE IV RESULTS

| Compound | calc PDE IV IC50 ($\mu$M) |
| --- | --- |
| 3-ethyl-8-isopropyl-6-ethylamino-3H-purine hydrochloride | 52.17 |
| 3-ethyl-8-cyclopentyl-6-benzylamino-3H-purine hydrochloride | 62.44 |
| 3-ethyl-8-cyclopentyl-6-ethylamino-3H-purine hydrochloride | 28.34 |
| 3-cyclohexylmethyl-6-ethylamino-3H-purine hydrochloride | 32.95 |
| 3-cyclohexylmethyl-8-cyclopropyl-6-ethylamino-3H-purine hydrochloride | 3.78 |
| 8-cyclopropyl-6-ethylamino-3-(3-methylbutyl)-3H-purine hydrochloride | 2.45 |
| 8-cyclopropyl-3-ethyl-6-propylamino-3H-purine hydrochloride | 15.67 |
| 8-cyclopropyl-3-cyclopropylmethyl-6-ethylamino-3H-purine hydrochloride | 4.11 |
| 3-hexyl-6-methylamino-3H-purine hydrochloride | 34.15 |
| 3-cyclopropylmethyl-8-isopropyl-6-ethylamino-3H-purine hydrochloride | 12.66 |
| 3-ethyl-8-isopropyl-6-benzylamino-3H-purine hydrochloride | 28.94 |
| 3-butyl-6-ethylamino-3H-purine hydrochloride | 66.41 |
| 3-butyl-8-cyclopropyl-6-ethylamino-3H-purine hydrochloride | 5.99 |
| 8-cyclopropyl-6-ethylamino-3-propyl-3H-purine hydrochloride | 6.31 |
| 8-cyclopropyl-6-cyclopropylamino-3-propyl-3H-purine hydrochloride | 7.90 |
| 3-(3-cyclopentyloxy-4-methoxybenzyl)-6-ethylamino-8-isopropyl-3H-purine hydrochloride | 0.32 |
| 3-(4-chlorobenzyl)-6-ethylamino-3H-purine hydrochloride | 37.75 |
| 3-ethyl-6-ethylamino-8-((3-cyclopentyloxy-4-methoxy)benzyl)-3H-purine hydrochloride | 4.52 |

EXAMPLE 23

Dithioxanthine derivatives of the present invention were manufactured and analyzed. The results are set forth in Table 5 below.

TABLE 5

DITHIOXANTHINES

| Compound | m.p. | IC50 PDE IV |
| --- | --- | --- |
| 3,7-dihydro-3-ethyl-2,6-dithio-1H-purine-2,6-dione | 275–276 | |
| 3,7-dihydro-3-propyl-2,6-dithio-1H-purine-2,6-dione | 294–297 | |
| 3,7-dihydro-8-ethyl-3-propyl-2,6-dithio-1H-purine-2,6-doine | 266–267 | |
| 3-butyl-3,7-dihydro-2,6-dithio-1H-purine-2,6-dione | 249–251 | |
| 3-butyl-3,7-dihydro-8-ethyl-2,6-dithio-1H-purine-2,6-dione | 251–252 | |
| 3,7-dihydro-3,8-diethyl-2,6-dithio-1H-purine-2,6-dione | 260–261 | |
| 3-benzyl-3,7-dihydro-2,6-dithio-1H-purine-2,6-dione | 298–303 | 38.49 |
| 3,7-dihydro-3-hexyl-2,6-dithio-1H-purine-2,6-dione | 222–224 | |
| 8-cyclopropyl-3,7-dihydro-3-(3-methylbutyl)-2,6-dithio-1H-purine-2,6-dione | | 6.31 |
| 8-cyclopropyl-3,7-dihydro-3-ethyl-2,6-dithio-1H-purine-2,6-dione | | 6.18 |
| 3,7-dihydro-3-(2-methylbutyl)-2,6-dithio-1H-purine-2,6-dione | 263–4 | |
| 3-butyl-8-cyclopropyl-3,7-dihydro-2,6-dithio-1H-purine-2,6-dione | | 9.43 |
| 3-cyclopropylmethyl-3,7-dihydro-2,6-dithio-1H-purine-2,6-dione | 276–8 | |
| 8-cyclopropyl-3,7-dihydro-3-propyl-2,6-dithio-1H-purine-2,6-dione | | 64.49 |
| 8-cyclopropyl-3-cyclopropylmethyl-3,7-dihydro-2,6-dithio-1H-purine-2,6-dione | | 2.27 |
| 3-butyl-3,7-dihydro-8-(1-methylethyl)-2,6-dithio-1H-purine-2,6-dione | | 5.93 |
| 3-cyclohexylmethyl-3,7-dihydro-2,6-dithio-1H-purine-2,6-dione | 292–4 | |
| 3-benzyl-3,7-dihydro-8-(1-methylethyl)-2,6-dithio-1H-purine-2,6-dione | | 3.40 |
| 3-cyclohexylmethyl-8-cyclopropyl-3,7-dihydro-2,6-dithio-1H-purine-2,6-dione | | 3.03 |
| 3-(3-cyclopentyloxy-4-methoxybenzyl)-3,7-dihydro-8-isopropyl-2,6-dithio-1H-purine-2,6-dione | 204–206 | 0.60 |
| 3-(3-cyclopentyloxy-4-methoxybenzyl)-3,7-dihydro-2,6-dithio-1H-purine-2,6-dione | 215–218 | 16.16 |
| 3-(4-chlorobenzyl)-8-isopropyl-3,7 dihydro-2,6-dithio-3,7-purine-2,6-dione | 242–243 | 2.40 |
| 3-ethyl-3,7-dihydro-8-isopropyl-2,6-dithio-1H-purine-2,6-dione | 248–250 | 4.10 |
| 3,7-dihydro-8-isopropyl-3-propyl-2,6-dithio-1H-purine-2,6-dione | 203 | 3.50 |
| 3-(2-chlorobenzyl)-3,7-dihydro-8-isopropyl-2,6-dithio-1H-purine-2,6-dione | 244–246 | 7.74 |
| 8-isopropyl-3-(4-pyridylmethyl)-2,6-dithio-1H-purine-2,6-dione | 310–315 | |

EXAMPLE 24

Pharmacologial Tests

Isolated Guinea Pig Trachea

The test compound was dissolved in dimethylsulfoxide. Guinea pig isolated trachealis muscle was mounted in a bath containing Krebs solution maintained at 37.5° C. and bubbled with carbogen (95% $O_2$, 5% $CO_2$).

Tension changes were recorded isometrically using force displacement transducers in conjunction with potentiometric pen recorders.

The ability of the test compounds to relax airways muscle was investigated by the construction of cumulative concentration effect curves. Each concentration of the test compound was allowed to equilibrate with the tissue for 5 minutes before a concentration increment (ten-fold) was made.

In each tissue the test compound was compared with theophylline as standard.

| Compound | In Vitro Activity |
|---|---|
| Theophylline | 1 |
| 8-Cyclopropyl-3-ethyl-6-ethylamino-3H-purine | 43.7 |
| 6-Ethylamino-3-hexyl-3H-purine | 25.6 |
| 3-Benzyl-6-ethylamino-3H-purine | 18.5 |

EXAMPLE 25

In-vivo Studies (i) The effect of test compounds in a model of bronchial hyperresponsiveness (BHR) and cellular infiltration in the guinea pig induced by ovalbumin (see, for example Morley et al, Agents and Actions, Supplement, 1988, 23, 187) were studied.

The test compound was administered at doses of 0.5 and 1.0 mg/kg/day given subcutaneously over 7 days by osmotic mini-pump. Theophylline and salbutamol at concen-trations of 1 mg/kg/day were used as standards. Dose response curves to histamine (1–50 μg/kg) were constructed for each animal.

FIGS. 1–2 show the results obtained.

(ii) Sensitization and Challenge procedure: Male Dunkin Hartley guine pigs (Charles River) (200–250 g) were injected i.p. with ovalbumin (OVA) (0.5 ml/animal; 20 μg OVA in Al(OH)$_3$ (moist gel)); this preparation produced an injectable stable suspension containing excess Al(OH)$_3$. Sham animals were injected with 0.5 ml Al(OH)$_3$ alone. After a period of 18–21 days animals were exposed to an aerosol of OVA (100 μg/ml) for 1 hour in an exposure chamber.

(iii) Bronchoalveolar lavage: Animals were anaesthetized, 24 hours after aerosol exposure, with urethane (25%, w/v, 7 ml/kg, i.p.) and the trachea cannulated. Bronchoalveo-lar lavage (BAL) was performed by instilling 5 ml sterile saline into the lungs via the tracheal cannula and the fluid was immediately removed. The fluid was reinjected and the procedure repeated 5 times in total. This procedure resulted in a 40–60% recovery of BAL fluid from the lungs of the guinea pig. Total cell counts were perfomed on the resultant BAL fluid using an improved Neubauer haemocytometer. Cytospin preparations were prepared using a Shandon Cytospin 2 centrifuge. Two drops of BAL fluid were added to each cytospin cup and the samples were centrifuged for 1 min at 1300 r.p.m. Slides were fixed in acetone and stained with haemotoxylin and carbol chromotrope according to the method described by Lendrum (Lendrum 1944), differential cell counts were performed on each slide by counting 200 cells at random, the cell types were classified as neutrophils, eosinophils and mononuclear cells according to standard morphological criteria. Cells were counted blind. The results are expressed as the number of neutrophils, eosinophils and mononuclear cells per ml of BAL fluid. The remaining BAL fluid was centrifuged (10 min., 1000 g) and the resultant cells and cell free supernatants were aliquotted and frozen for later assays. Compounds were solu-bilized in either DMSO or saline administered intraperitoreally at a dose of 5 mg/kg one hour prior to ovalbumin challenge. The results are provided below in Table 6.

TABLE 6

| Compound | N | Dose mg/kg ip | % Eosinophils in BAL x ± se | % Inhibition |
|---|---|---|---|---|
| DMSO Vehicle | 9 | — | 32 ± 6 | — |
| 3-(3-cyclo-pentyloxy-4-methoxybenzyl)-3,7-dihydro-8-iso-propyl-2,6-dithio-1H-purin-2,6-dione | 6 | 5 | 17 ± 3 | 47% |
| Saline Vehicle | 14 | — | 33 ± 3 | — |
| 8-cyclopropyl-6-ethylamino-3-(3-methylbutyl)-3H-purine hydro-chloride | 7 | 5 | 16 ± 4 | 52% |
| 3-(3-cyclopentyl-oxy-4-methoxy-benzyl)-6-ethylamino-8-isopropyl-3H-purine hydro-chloride | 7 | 5 | 12 ± 2 | 64% |

EXAMPLE 26

Synthesis and Assay of Adenine Compounds

Following the previously set forth methods, the following adenine derivatives of the present invention were synthesized and assayed for PDE IV inhibition activity as provided in Table 7 below.

TABLE 7

PDE IV RESULTS

| Compound | calc PDE IV IC50 (μM) |
|---|---|
| 6-Amino-3-(3-cyclopentyloxy-4-methoxy-benzyl)-8-(1-methylethenyl)-3H-purine; | .091 |
| 6-Amino-8-benzyloxymethyl-3-(3-cyclopentyloxy-4-methoxy-benzyl)-3H-purine; | .052 |
| 6-amino-8-[(1-benzyloxy-1-methyl)ethyl]-3-[(3-cyclopentyloxy-4-methoxy)benzyl]-3H-purine; | .005 |

TABLE 7-continued

PDE IV RESULTS

| Compound | calc PDE IV IC50 (μM) |
|---|---|
| 6-Amino-3-(3-cyclopentyloxy-4-methoxybenzyl)-8-[1-(4-fluorobenzyloxy)-1-methyl-ethyl]-3H-purine; | .034 |
| [8-(1-benzyloxy-1-methyl)ethyl]3-[(3-cyclopentyloxy-4-methoxy)benzyl]-6-ethylamino-3H-purine; | .85 |
| 6-Amino-8-benzyloxymethyl-3-(3-cyclopentyloxy-4-methoxybenzyl)-3H-purine; | .45 |
| 3-[(3-cyclopentyloxy-4-methoxy)benzyl]-6-ethylamino-8-[(1-hydroxy-1-methyl)ethyl]-3H-purine; | .85 |
| 6-Ethylamino-3-(3-butoxy-4-methoxy-benzyl)-8-isopropyl-3H purine; | 1.4 |
| 6-amino-3-[(3-cyclopentyloxy-4-methoxy)benzyl]-8-[(1-hydroxy-1-methyl)ethyl]-3H-purine; | .25 |
| 3-[(3-cyclopentyloxy-4-methoxy)benzyl]-6-ethylamino-8-(1-methyl-ethenyl)-3H-purine; | .27 |
| 6-ethylamino-2-(3,4-dimethoxybenzyl)-8-isopropyl-3H-purine; | .31 |
| 6-Amino-3-(3-cyclopentyloxy-4-methoxybenzyl)-3H-purine; | .31 |
| 3-(3-cyclopentyloxy-4-methoxybenzyl)-6-dimethylamino-8-isopropyl-3H-purine; | 19.3 |
| 6-Ethylamino-3-[3-(3-hydroxycyclopentyloxy)-4-methoxybenzyl)]-8-(1-hydroxy-1-methylethyl)-3H-purine; | 2.6 |
| 6-ethylamino-3-(3-,4-methylenedioxybenzyl)-8-isopropyl-3H-purine; | .44 |
| 6-ethylamino-3-[(3-cyclopentyloxy-4-methoxy)benzyl]-8-isopropyl-3H-purine; | .66 |
| 3-(3-benzyloxy-4-methoxy-benzyl)-6-ethylamino-8-isopropyl-3H-purine; | 1.3 |
| 6-Amino-3-(3,4-dimethoxybenzyl)-8-[1-(4-fluorobenzyloxy)-1-methylethyl]-3H-purine; | 1.85 |
| 3-(3-cyclopentyloxy-4-methoxybenzyl)-6-amino-8-isopropyl-3H-purine; | .82 |
| 6-(amino-8-(1-benzyloxy-1-methylethyl)-3-(3,4-dimethoxybenzyl)-3H-purine; | .94 |
| 3-(3-cyclopentyloxy-4-methoxybenzyl)-6-(3-cyclopentyloxy-4-methoxybenzylamino)-8-isopropyl-3H-purine; | 1.14 |
| 6-ethylamino-8-isopropyl-3-(4-methoxybenzyl)-3H-purine; | 1.2 |
| 3-(3-((3-hydroxy)cyclopentyloxy)-4-methoxybenzyl)-6-ethylamino-8-isopropyl-3H-purine; | 1.36 |
| 3-(3-cyclopentyloxy-4-methoxybenzyl)-6-(N-benzoyl-N-ethylamino)-8-isopropyl-3H-purine; | 1.43 |
| 3-(4-chlorobenzyl)-6-cyclopropylamino-8-isopropyl-3H-purine; | 1.69 |
| 6-ethylamino-8-isopropyl-3-[(4-methoxy-3-(4-hydroxybutoxy))benzyl]-3H-purine; | 1.75 |
| 6-ethylamino-3-(4-fluorobenzyl)-8-isopropyl-3H-purine; | 1.85 |
| 3-(3-chlorobenzyl)-6-ethylamino-8-isopropyl-3H-purine; | 2.15 |
| 3-[3-(3-Hydroxy-cyclopentyloxy)-4-methoxy-benzyl]-8-(1-hydroxy-1-methyl-ethyl)-3H-purine; | 2.25 |
| 3-[3-(3-hydroxy)cyclopentyloxy)]-4-methoxy)benzyl)-6-ethylamino-8-isopropyl-3H-purine; | 2.28 |
| 6-amino-3-(3,4-dimethoxybenzyl)-8-isopropyl-3H-purine; | .92 |
| 6-Ethylamino-3-[3-cyclopentylmethoxy-4-methoxy-benzyl]-8-isopropyl-3H-purine; | 12.5 |
| 6-ethylamino-3-(3-hydroxy-4-methoxybenzyl)-8-isopropyl-3H-purine; | 2.73 |
| 6-Ethylamino-3-[3-(2,2-dimethylaminoethoxy-4-methoxy)]-8-isopropyl-3H-purine; | 8.95 |
| 3-[(3-cyclopentyloxy-4-methoxy)benzyl]-8-[(1-methyl-1-hydroxy)ethyl]-6-ethylamino-3H-purine; | 3.1 |
| 6-amino-3-[(3-benzyloxy-4-methoxy)benzyl]-8-[(1-benzyloxy-1-methyl)ethyl]-3H-purine; | 3.12 |
| 3-(3-cyclopentyloxy-4-methoxybenzyl)-6-((2,2,2-trifluoroethyl)amino)-8-isopropyl-3H-purine; | 12.8 |
| 6-Ethylamino-3-[3-(2,2,2)-azabicyclooctan-3-yloxy)-4-methoxy]-8-isopropyl-3H-purine; | 2.05 |
| 6-Ethylamino-3-[3-(1-methylpiperidin-4-yl-methoxy)-4-methoxy-benzy]-8-isopropyl-3H-purine; | 6.6 |
| 6-Amino-3-(3,4-dimethyoxybenzyl)-8-(1-methylethenyl)-3H-purine; | 3.7 |
| 6-amino-8-isopropyl-3-[(4-methoxy-3-([(4-hydroxybutoxy))benzyl]-3H-purine; | 4.2 |
| 3-{2-(4-chlorophenyl)-ethyl]-6-ethylamino-8-isopropyl-3H-purine; | 4.46 |
| 3-(4-chlorobenzyl)-6-((1-hydroxy)cyclopentylamino)-8-isopropyl-3H-purine; | 4.48 |

TABLE 7-continued

PDE IV RESULTS

| Compound | calc PDE IV IC50 (μM) |
|---|---|
| 3-(4-chlorobenzyl)-6-cyclopentylamino-8-isopropyl-3H-purine, | 4.7 |
| 6-amino-3(3,4-methylenedioxybenzyl)-8-isopropyl-3H-purine; | 4.1 |
| 6-Ethylamino-3-[(exo-8-methyl-8-azabicyclo(3,2,1)-octan-3-yl-oxy)-4-methoxy-benzy]-8-isopropyl-3-H-purine; | 6.02 |
| 6-amino-3-((3-benzyloxy-4-methoxy)-bezyl)-8-isopropyl-3H-purine; | 6.4 |
| 3-(4-chlorophenyl)-6-ethylamino-8-isopropyl-3H-purine; | 6.5 |
| 6-ethylamino-3-[(3-hydroxy-4-methoxy)benzyl]-8-[(1-hydroxy-1-methyl)ethyl]- -3H-purine; | 6.5 |
| 6-Ethylamino-3-[(3-pyridin-4-yl-methoxy)N-oxide-4-methoxy]-8-isopropyl-3H-purine; | 4.5 |
| 3-[3-Cyclohexanyl-4-oxy-4-methoxy-benzyl]-6-ethylamino-8-isopropyl-3H-purine; | 8.28 |
| 3-(4-chlorobenzyl)-2,6-di(ethylamino)-8-isopropyl-3H-purine; | 11.2 |
| 6-amino-3-(3-hydroxy-4-methoxy)-benzyl)-8-isopropyl-3H-purine; | 15.1 |
| 6-amino-3-[3-(4-hydroxybutoxy-4-methoxy)benzyl]-8-(1-hydroxy-1-methylethyl)-3H-purine hydrochloride; | 17.1 |
| 6-amino-3-(4-chlorobenzyl)-8-isopropyl-3H-purine; | 20.8 |
| 6-amino-3-cyclopentylmethyl-8-isopropyl-3H-purine; | 23.2 |
| 8-cyclopropyl-3-ethyl-6-ethylamino-3H-purine; | 27.1 |
| 6-Ethylamino-8-isopropyl-3-[3-(pyridin-4-yl-methoxy)-4-methoxy-benzyl]-3H-purine; | 24.5 |
| 6-Ethylamino-3-(1-oxopyridin-4-yl-methyl)-8-isopropyl-3H-purine; and | 385 |
| 6-amino-3-[(3-hydroxy-4-methoxy)benzyl)]]-8-[(1-hydroxy-1-methyl)ethyl]-3H-purine | 71000 |
| 6-amino-3-[(3-cyclopentyloxy-4-methoxy)benzyl]-8-[(1-(2-methoxy)benzyloxy-1-methyl)ethyl]-3H-purine | 38 |
| 6-amino-3-[(3-cyclopentyloxy-4-methoxy)benzyl]-8-[(1-(3-methoxy)benzyloxy-1-methyl)ethyl]-3H-purine | 30 |
| 6-amino-3-[(3,4-dimethoxy)benzyl]-8-[(1-(4-methyl)benzyloxy-1-methyl)ethyl]-3H-purine | 20 |
| 6-amino-3-[(3-cyclopentyloxy-4-methoxy)benzyl]-8-[(1-(4-chloro)benzyloxy-1-methyl)ethyl]-3H-purine | 25 |
| 6-amino-3-[(3-cyclopentyloxy-4-methoxy)benzyl]-8-[(1-(2-fluoro)benzyloxy-1-methyl)ethyl]-3H-purine | 45 |
| 6-amino-3-[(3-cyclopentyloxy-4-methoxy)benzyl]-8-[(1-(3-fluoro)benzyloxy-1-methyl)ethyl]-3H-purine | 60 |
| 6-(3-fluoro)benzyloxyamino-3-[(3-cyclopentyloxy-4-methoxy)benzyl]-8-[(1-(3-fluoro)benzyloxy-1-methyl)ethyl]-3H-purine | 122 |
| 6-amino-3-[(3-cyclopentyloxy-4-methoxy)benzyl]-8-[(1-(3,5-dimethoxy)benzyloxy-1-methyl)ethyl]-3H-purine | 44 |
| 6-amino-3-[(3-cyclopentyloxy-4-methoxy)benzyl]-8-[(1-(3,4-dimethoxy)benzyloxy-1-methyl)ethyl]-3H-purine | 92 |
| 6-amino-3-[(3-cyclopentyloxy-4-methoxy)benzyl]-8-[(1-(3,4-fluoro)benzyloxy-1-methyl)ethyl]-3H-purine | 49 |
| 6-amino-3-[(3-cyclopentyloxy-4-methoxy)benzyl]-8-[(3,4-methylenedioxybenzyloxy-1-methyl)ethyl]-3H-purine | 35 |
| 6-amino-3-[(3-cyclopentyloxy-4-methoxy)benzyl]-8-[(2-thienylmethoxy-1-methyl)ethyl]-3H-purine | 53 |
| 6-amino-3-[(3-cyclopentyloxy-4-methoxy)benzyl]-8-[(3-thienylmethoxy-1-methyl)ethyl]-3H-purine | 83 |
| 6-amino-3-[(3-cyclopentyloxy-4-methoxy)benzyl]-8-[(1-(1-oxo-octyl)amino-1-methyl)ethyl]-3H-purine | 109 |
| 6-amino-3-(3,4-methylenedioxybenzyl)-8-[1-(4-fluorobenzyloxy)-1-methyl-ethyl]-3H-purine | .72 |
| 6-Amino-8-benzyloxymethyl-3-(3-cyclopentyloxy-4-methoxy-benzyl)-3H-purine; | .17 |

While the invention has been illustrated with respect to the production and use of particular compounds, it is apparent that variations and modifications of the invention can be made without departing from the spirit or scope of the invention.

What is claimed is:
1. A compound of the formula (I):

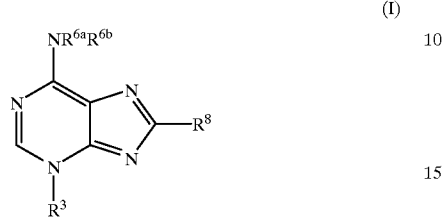

and pharmaceutically acceptable salts thereof,
wherein $R^3$, $R^{6a}$, $R^{6b}$, and $R^8$ is selected from the group consisting of A and B,
wherein A is selected from the group consisting of
hydrogen;
$C_{1-10}$ alkyl which is unbranched or branched and is optionally substituted with 1–3 substituents chosen from the group consisting of OH, $C_{1-10}$ alkoxy, $C_{3-12}$ cycloalkoxy, halogen =NOH, =NOCONH$_2$, CO$_2$H, =O and benzyloxy; said benzyloxy optionally substituted with 1–3 substituents chosen from the group consisting of halogen, $C_{1-10}$ alkyl, $C_{3-12}$ cycloalkyl, $C_{1-10}$ alkoxy and $C_{3-12}$ cycloalkoxy;
$C_{2-10}$ alkenyl which is unbranched or branched and is optionally substituted with 1–3 substituents chosen from the group consisting of OH, $C_{3-12}$ cycloalkyl, $C_{1-10}$ alkoxy, $C_{3-12}$ cycloalkoxy, halogen, =NOH, =NOCONH$_2$, CO$_2$H and =O;
$C_{3-10}$ cycloalkyl which is optionally substituted with 1–3 substituents chosen from the group consisting of OH, $C_{1-10}$ alkyl, $C_{3-12}$ cycloalkyl, $C_{1-10}$ alkoxy, $C_{1-10}$ alkoxy, $C_{3-12}$ cycloalkoxy, halogen, halo($C_{1-10}$)alkyl, =NOH, =NOCONH$_2$, CO$_2$H and =O;
$C_{3-10}$ cycloalkenyl which is optionally substituted with 1–3 substituents chosen from the group consisting of OH, $C_{1-10}$ alkyl, $C_{3-12}$ cycloalkyl, $C_{1-10}$ alkoxy, $C_{3-12}$ cycloalkoxy, halogen, halo($C_{1-10}$)alkyl, =NOH, =NOCONH$_2$, CO$_2$H and =O;
$C_{3-12}$ cycloalkyl($C_{1-10}$)alkyl wherein the cycloalkyl portion is optionally substituted with 1–3 substituents chosen from the group consisting of OH, $C_{1-10}$ alkyl, $C_{3-12}$ cycloalkyl, $C_{1-10}$ alkoxy, $C_{3-12}$ cycloalkoxy, halogen, halo($C_{1-10}$)alkyl, =NOH, =NOCONH$_2$, CO$_2$H and =O;
aryl which is optionally substituted with 1–3 substituents chosen from the group consisting of $C_{1-10}$ alkyl, $C_{3-12}$ cycloalkyl, OH, halogen, $C_{1-10}$ alkoxy, $C_{3-12}$ cycloalkoxy, NH$_2$, $C_{1-10}$ alkylamino, $C_{1-10}$ dialkylamino, carbamyl, amido, $C_{1-10}$ alkylamido, $C_{1-10}$ dialkylamido, $C_{1-10}$ acylamino, $C_{1-10}$ alkysulfonylamino, phenyl and benzyl;
ar($C_{1-4}$)alkyl wherein the aryl moiety is optionally substituted with 1–3 substituents chosen from the group consisting of carboxy, $C_{1-10}$ alkylcarboxy, halogen, hydroxy, hydroxy($C_{1-10}$) alkoxy, nitro, trihalocarbon, benzyloxy, heterocyclyl, $C_{1-10}$ cycloalkyl($C_{3-12}$)alkyloxy, ar($C_{1-10}$)alkyloxy, aryloxy, amino($C_{1-10}$)alkoxy, $C_{1-10}$ alkylamino($C_{1-10}$)alkoxy, heteroaryloxy, heteroar($C_{1-10}$)alkyloxy, heterocyclyloxy, $C_{1-10}$ alkyl, $C_{3-12}$ cycloalkyl, $C_{1-10}$ alkoxy and $C_{3-12}$ cycloalkoxy; said alkoxy and cycloalkoxy optionally substituted on a carbon with hydroxy and said heterocyclyl is optionally substituted with $C_{1-10}$ alkyl; and wherein the alkyl moiety of said ar ($C_{1-14}$)alkyl is optionally substituted with OH, halogen, $C_{1-10}$ alkoxy or $C_{3-12}$ cycloalkoxy; said alkoxy and cycloalkoxy being optionally substituted in one position at the alkyl moiety with hydroxy;
heterocyclyl which is optionally substituted on the carbons or nitrogens of the ring with 1–3 substituents chosen from the group consisting of $C_{1-10}$ alkyl, OH, halogen, $C_{1-10}$ alkoxy, $C_{3-12}$ cycloalkoxy, NH$_2$, $C_{1-10}$ alkylamino, $C_{1-10}$ dialkylamino, amido, $C_{1-10}$ alkylamido, $C_{1-10}$ dialkylamido, $C_{1-10}$ acylamino, $C_{1-10}$ alkylsulfonylamino, phenyl and benzyl;
heterocycly($C_4$–$C_4$)alkyl wherein said heterocyclyl moiety is optionally substituted on the carbons or nitrogens of the ring with 1–3 substituents chosen from the group consisting of $C_{1-10}$ alkyl, $C_{3-12}$ cycloalkyl, OH, halogen, $C_{1-12}$ alkoxy, $C_{3-12}$ cycloalkoxy, NH$_2$, $C_{1-10}$ alkylamino, $C_{1-10}$ dialkylamino, carbamyl, amido, $C_{1-10}$ alkylamido, $C_{1-10}$ dialkylamido, $C_{1-10}$ acylamino, $C_{1-10}$ alkylsulfonylamino, phenyl and benzyl, and wherein said alkyl moiety is optionally substituted with OH, $C_{1-10}$ alkoxy, $C_{3-12}$ cycloalkoxy, $C_{3-12}$ cycloalkyl, halogen or halo($C_{1-10}$)alkyl;
heteroaryl, which is optionally substituted with 1–3 substituents chosen from the group consisting of $C_{1-10}$ alkyl, $C_{3-12}$ cycloalkyl, halogen, nitro, CF$_3$, $C_{1-10}$ alkoxy and $C_{3-12}$ cycloalkoxy; and
heteroaryl($C_{1-4}$)alkyl, wherein the heteroaryl moiety is optionally substituted with 1–3 substituents chosen from the group consisting of $C_{1-10}$ alkyl, $C_{3-12}$ cycloalkyl, halogen, nitro trihalocarbon, $C_{1-10}$ to alkoxy and $C_{3-12}$ cycloalkoxy; and
B is selected from the group consisting of
$C_{1-10}$ alkyl which is unbranched or branched and is substituted with 1–3 substituents chosen from the group consisting of benzyloxy, methylenedioxybenzyloxy, methylenedioxyphenyl, pyridylmethoxy, thienylmethoxy and alkylamino; said substituents optionally substituted with 1–3 substituents chosen from the group consisting of halogen, $C_{1-10}$ alkyl, $C_{3-12}$ cycloalkyl, $C_{1-10}$ alkoxy, $C_{3-12}$ cycloalkoxy and oxo; said substituted $C_{1-10}$ alkyl further optionally substituted with 1–3 substituents chosen from the group consisting of OH, $C_{1-10}$ alkoxy, $C_{3-12}$ cycloalkoxy, halogen, =NOH, =NOCONH$_2$, CO$_2$H, and =O;
$C_{2-3}$ or $C_{7-10}$ alkenyl which is unbranched or branched and is optionally substituted with 1–3 substituents chosen from the group consisting of OH, $C_{3-12}$ cycloalkyl, $C_{1-10}$ alkoxy, $C_{3-12}$ cycloalkoxy, halogen, =NOH, =NOCONH$_2$, CO$_2$H and =O;
$C_{3-10}$ cycloalkyl which is substituted with 1–3 substituents chosen from the group consisting of $C_{2-10}$ alkyl and $C_{3-12}$ cycloalkyl; said substituted $C_{3-10}$ cycloalkyl further optionally substituted with 1–3 substituents chosen from the group consisting of OH, $C_{1-10}$ alkoxy, $C_{3-12}$ cycloalkoxy, halogen halo($C_{1-10}$) alkyl, =NOH, =NOCONH$_2$, CO$_2$H and =O;
$C_{3-10}$ cycloalkenyl which is optionally substituted with 1–3 substituents chosen from the group consisting of OH, $C_{1-10}$ alkyl, $C_{3-12}$ cycloalkyl, $C_{1-10}$ alkoxy, $C_{3-12}$ cycloalkoxy, halogen, halo($C_{1-10}$)alkyl, =NOH, =NOCONH$_2$, CO$_2$H and =O;

$C_{3-12}$ cycloalkyl($C_{1-10}$)alkyl wherein the cycloalkyl portion is substituted with 1–3 substituents chosen from the group consisting of $C_{1-10}$ alkyl, and $C_{3-12}$ cycloalkyl; said substituted $C_{3-12}$ cycloalkyl($C_{1-10}$) alkyl further optionally substituted with 1–3 substituents chosen from the group consisting of OH, $C_{1-10}$ alkoxy, $C_{3-12}$ cycloalkoxy, =NOH, =NOCONH$_2$, and CO$_2$H;

aryl which is substituted with 1–3 substituents chosen from the group consisting of amido, $C_{1-10}$ alkylamido, and $C_{1-10}$ dialkylamido; said substituted aryl further optionally substitute with 1–3 substituents chosen from the group consisting of $C_{1-10}$ alkyl, $C_{3-12}$ cycloalkyl OH, halogen, $C_{1-10}$ alkoxy, $C_{3-12}$ cycloalkoxy, NH$_2$, $C_{1-10}$ akylamino, $C_{1-10}$ dialkylamino, phenyl and benzyl;

ar($C_{1-4}$)alkyl wherein the aryl moiety is substituted with 1–3 substituents chosen from the group consisting of carboxy, $C_{1-10}$ alkylcarboxy, hydroxy($C_{1-10}$)alkoxy, nitro, benzyloxy, heterocyclyl, $C_{1-10}$ cycloalkyl($C_{3-12}$)alkyloxy, ar($C_{1-10}$)alkyloxy, aryloxy, amino($C_{1-10}$)alkoxy, $C_{1-10}$ alkylamino($C_{1-10}$)alkoxy, heteroaryloxy, heteroar($C_{1-10}$)alkyloxy, heterocyclyloxy, $C_{1-10}$ alkoxy and $C_{3-12}$ cycloalkoxy; said alkoxy and cycloalkoxy substituted on a carbon with hydroxy and said heterocyclyl is optionally substituted with $C_{1-10}$ alkyl and wherein the alkyl moiety of said ar ($C_{1-4}$)alkyl is optionally substituted with OH, halogen, $C_{1-10}$ alkoxy or $C_{3-12}$ cycloalkoxy; said alkoxy and cycloalkoxy being optionally substituted in one position at the alkyl moiety with hydroxy; and said substituted ar($C_{1-4}$) alkyl further optionally substituted with 1–3 substituents chosen from the group consisting of halogen, hydroxy, trihalocarbon, $C_{1-10}$ alkyl, $C_{3-12}$ cycloalkyl, $C_{1-10}$ alkoxy and $C_{3-12}$ cycloalkoxy;

heterocyclyl which is substituted on the carbons or nitrogens of the ring with 1–3 substituents chosen from the group consisting of carbamyl, $C_{1-10}$ acylamino and $C_{1-10}$ alkylsulfonylamino; said substituted heterocyclyl further optionally substituted with 1–3 substituents chosen from the group consisting of $C_{1-10}$ alkyl, OH, halogen, $C_{1-10}$ alkoxy, $C_{3-12}$ cycloalkoxy, NH$_2$, $C_{1-10}$ alkylamino, $C_{1-10}$ dialkylamino, amido, $C_{1-10}$ alkylamido, $C_{1-10}$ dialkylamido, phenyl and benzyl;

heterocyclyl($C_1$–$C_4$)alkyl wherein said heterocyclyl moiety is substituted on the carbons or nitrogens of the ring with 1–3 substituents chosen from the group consisting of $C_{1-10}$ acylamino, $C_{1-10}$ alkylsulfonylamino, and $C_{1-10}$ alkyl, said $C_{1-10}$ alkyl substituted with OH, $C_{1-10}$ alkoxy, $C_{3-12}$ cycloalkoxy, $C_{3-12}$ cycloalkyl, halogen or halo($C_{1-10}$)alkyl; said substituted heterocyclyl($C_1$–$C_4$)alkyl further optionally substituted with 1–3 substituents chosen from the group consisting of $C_{1-10}$ alkyl, $C_{3-12}$ cycloalkyl, OH, halogen, $C_{1-10}$ alkoxy, $C_{3-12}$ cycloalkoxy, NH$_2$, $C_{1-10}$ alkylamino, $C_{1-10}$ dialkylamino, amido, $C_{1-10}$ alkylamido and $C_{1-10}$ dialkylamido;

heteroaryl is optionally substituted with 1–3 substitutents chosen from the group consisting of $C_{1-10}$ alkyl, $C_{3-12}$ cycloalkyl, halogen, nitro, CF$_3$, $C_{1-10}$ alkoxy and $C_{3-12}$ cycloalkoxy and heteroaryl($C_{1-4}$)alkyl, wherein the heteroaryl moiety is substituted with nitro; said heteroaryl($C_{1-4}$)alkyl further optionally substituted with 1–3 substituents chosen from the group consisting of $C_{1-10}$ alkyl, $C_{3-12}$ cycloalkyl, halogen, trihalocarbon, $C_{1-10}$ alkoxy and $C_{3-12}$ cycloalkoxy; and provided that at least one of $R^3$, $R^{6a}$, $R^{6b}$ and $R^8$ is B.

2. The compound of claim 1 wherein $R^3$ is A and is ar($C_{1-4}$)alkyl wherein the aryl moiety is optionally substituted with 1–3 substituents chosen from the group consisting of halogen, nitro, $C_{1-10}$ alkoxy, $C_{3-12}$ cycloalkoxy and CF$_3$, and wherein the alkyl moiety is optionally substituted with 1–3 substituents chosen from the group consisting of OH, halogen, $C_{1-10}$ alkoxy and $C_{3-12}$ cycloalkoxy.

3. The compound of claim 2 wherein said aralkyl is benzyl.

4. The compound of claim 3 wherein the aryl moiety of said benzyl is substituted with 1–3 substituents chosen from the group consisting of halogen, nitro, $C_{1-10}$ alkoxy, $C_{3-12}$ cycloalkoxy and CF$_3$.

5. The compound of claim 4 wherein said benzyl is substituted with cyclopentyloxy and methoxy.

6. The compound of claim 2 wherein $R^{6a}$ is A and is hydrogen.

7. The compound of claim 1 wherein $R^{6b}$ is A and is selected from the group consisting of hydrogen;

$C_{1-8}$ alkyl which is unbranched or branched and is optionally substituted with OH, alkoxy, cycloalkoxy, halogen, =NOH, =NOCONH$_2$, CO$_2$H or =O; and $C_{3-8}$ cycloalkyl which is optionally substituted with OH, alkoxy, cycloalkoxy, halogen, haloalkyl, =NOH, =NOCONH$_2$, CO$_2$H or =O.

8. The compound of claim 1 wherein $R^8$ is B and is $C_{1-10}$ alkyl which is unbranched or branched and is substituted with 1–3 substituents chosen from the group consisting of benzyloxy, methylenedioxybenzyloxy, methylenedioxyphenyl, pyridylmethoxy, thienylmethoxy and alkylamino, said substituents optionally substituted with 1–3 substituents chosen from the group consisting of halogen, $C_{1-10}$ alkyl, $C_{3-12}$ cycloalkyl, $C_{1-10}$ alkoxy, $C_{3-12}$ cycloalkoxy and oxo.

9. A method for selectively effecting PDE IV inhibition, compared to PDE III inhibition, in a patient suffering from a disease state selected from the group consisting of inflammation, depression, Alzheimer's disease, vascular dementia, and multi-in-farct demetia, said method comprising the administration of a compound of the formula (I):

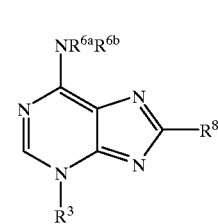

(I)

and pharmaceutically acceptable salts thereof, wherein $R^3$, $R^{6a}$, $R^{6b}$, and $R^8$ is selected from the group consisting of A and B, wherein A is selected from the group consisting of hydrogen;

$C_{1-10}$ alkyl which is unbranched or branched and is optionally substituted with 1–3 substituents chosen from the group consisting of OH, $C_{1-10}$ alkoxy, $C_{3-12}$ cycloalkoxy, halogen =NOH, =NOCONH$_2$, $CO_2H$, ↑O and benzyloxy; said benzyloxy optionally substituted with 1–3 substituents chosen from the group consisting of halogen, $C_{1-10}$ alkyl, $C_{3-12}$ cycloalkyl, $C_{1-10}$ alkoxy and $C_{3-12}$ cycloalkoxy;

$C_{2-10}$ alkenyl which is unbranched or branched and is optionally substituted with 1–3 substituents chosen from the group consisting of OH, $C_{3-12}$ cycloalkyl, $C_{1-10}$ alkoxy, $C_{3-12}$ cycloalkoxy, halogen, =NOH, =NOCONH$_2$, $CO_2H$ and =O;

$C_{3-10}$ cycloalkyl which is optionally substituted with 1–3 substituents chosen from the group consisting of OH, $C_{1-10}$ alkyl, $C_{3-12}$ cycloalkyl, $C_{1-10}$ alkoxy, $C_{1-10}$alkoxy, $C_{3-12}$ cycloalkoxy, halogen, halo($C_{1-10}$)alkyl, =NOH, =NOCONH$_2$, $CO_2H$ and =O;

$C_{3-10}$ cycloalkenyl which is optionally substituted with 1–3 substituents chosen from the group consisting of OH, $C_{1-10}$ alkyl, $C_{3-12}$ cycloalkyl, $C_{1-10}$ alkoxy, $C_{3-12}$ cycloalkoxy, halogen, halo($C_{1-10}$)alkyl, =NOH, =NOCONH$_2$, $CO_2H$ and =O;

$C_{3-12}$cycloalkyl($C_{1-10}$)alkyl wherein the cycloalkyl portion is optionally substituted with 1–3 substituents chosen from the group consisting of OH, $C_{1-10}$ alkyl, $C_{3-12}$ cycloalkyl, $C_{1-10}$ alkoxy, $C_{3-12}$ cycloalkoxy, halogen, halo($C_{1-10}$)alkyl, =NOH, =NOCONH$_2$, $CO_2H$ and =O;

aryl which is optionally substituted with 1–3 substituents chosen from the group consisting of $C_{1-10}$ alkyl, $C_{3-12}$ cycloalkyl, OH, halogen, $C_{1-10}$ alkoxy, $C_{3-12}$ cycloalkoxy, $NH_2$, $C_{1-10}$ alkylamino, $C_{1-10}$ dialkylamino, carbamyl, amido, $C_{1-10}$ alkylamido, $C_{1-10}$dialkylamido, $C_{1-10}$ acylamino, $C_{1-10}$ alkysulfonylamino, phenyl and benzyl;

ar($C_{1-4}$)alkyl wherein the aryl moiety is optionally substituted with 1–3 substituents chosen from the group consisting of carboxy, $C_{1-10}$ alkylcarboxy, halogen, hydroxy, hydroxy($C_{1-10}$) alkoxy, nitro, trihalocarbon benzyloxy, heterocyclyl, $C_{1-10}$ cycloalkyl($C_{3-12}$)alkyloxy, ar($C_{1-10}$)alkyloxy, aryloxy, amino($C_{1-10}$)alkoxy, $C_{1-10}$ alkylamino($C_{1-10}$)alkoxy, heteroaryloxy, heteroar($C_{1-10}$)alkyloxy, heterocyclyloxy, $C_{1-10}$ alkyl, $C_{3-12}$ cycloalkyl, $C_{1-10}$ alkoxy and $C_{3-12}$ cycloalkoxy; said alkoxy and cycloalkoxy optionally substituted on a carbon with hydroxy and said heterocyclyl is optionally substituted with $C_{1-10}$ alkyl; and wherein the alkyl moiety of said ar ($C_{1-14}$)alkyl is optionally substituted with OH, halogen, $C_{1-10}$ alkoxy or $C_{3-12}$ cycloalkoxy; said alkoxy and cycloalkoxy being optionally substituted in one position at the alkyl moiety with hydroxy;

heterocyclyl which is optionally substituted on the carbons or nitrogens of the ring with 1–3 substituents chosen from the group consisting of $C_{1-10}$ alkyl, OH, halogen, $C_{1-10}$ alkoxy, $C_{3-12}$ cycloalkoxy, $NH_2$, $C_{1-10}$ alkylamino, $C_{1-10}$ dialkylamino, amido, $C_{1-10}$ alkylamido, $C_{1-10}$ dialkylamido, $C_{1-10}$ acylamino, $C_{1-10}$ alkylsulfonylamino, phenyl and benzyl;

heterocycly($C_1$–$C_4$)alkyl wherein said heterocyclyl moiety is optionally substituted on the carbons or nitrogens of the ring with 1–3 substituents chosen from the group consisting of $C_{1-10}$ alkyl, $C_{3-12}$ cycloalkyl, OH, halogen, $C_{1-10}$ alkoxy, $C_{3-12}$ cycloalkoxy, $NH_2$, $C_{1-10}$ alkylamino, $C_{1-10}$ dialkylamino, carbamyl, amido, $C_{1-10}$ alkylamido, $C_{1-10}$ dialkylamido, $C_{1-10}$ acylamino, $C_{1-10}$ alkylsulfonylamino, phenyl and benzyl, and wherein said alkyl moiety is optionally substituted with OH, $C_{1-10}$ alkoxy, $C_{3-12}$ cycloalkoxy, $C_{3-12}$ cycloalkyl, halogen or halo($C_{1-10}$)alkyl;

heteroaryl, which is optionally substituted with 1–3 substituents chosen from the group consisting of $C_{1-10}$ alkyl, $C_{3-12}$ cycloalkyl, halogen, nitro, $CF_3$, $C_{1-10}$ alkoxy and $C_{3-12}$ cycloalkoxy; and heteroaryl($C_{1-4}$)alkyl, wherein the heteroaryl moiety is optionally substituted with 1–3 substituents chosen from the group consisting of $C_{1-10}$ alkyl, $C_{3-12}$ cycloalkyl, halogen, nitro trihalocarbon, $C_{1-10}$ alkoxy and $C_{3-12}$ cycloalkoxy; and B is selected from the group consisting of $C_{1-10}$ alkyl which is unbranched or branched and is substituted with 1–3 substituents chosen from the group consisting of benzyloxy, methylenedioxybenzyloxy, methylenedioxyphenyl, pyridylmethoxy, thienylmethoxy and alkylamino; said substituents optionally substituted with 1–3 substituents chosen from the group consisting of halogen, $C_{1-10}$ alkyl, $C_{3-12}$ cycloalkyl, $C_{1-10}$ alkoxy, $C_{3-12}$ cycloalkoxy and oxo; said substituted $C_{1-10}$ alkyl further optionally substituted with 1–3 substituents chosen from the group consisting of OH, $C_{1-10}$ alkoxy, $C_{3-12}$ cycloalkoxy, halogen, =NOH, =NOCONH$_2$, $CO_2H$, and =O;

$C_{2-10}$ alkenyl which is unbranched or branched and is optionally substituted with 1–3 substituents chosen from the group consisting of OH, $C_{3-12}$ cycloalkyl, $C_{1-10}$ alkoxy, $C_{3-12}$ cycloalkoxy, halogen, =NOH, =NOCONH$_2$, $CO_2H$ and =O;

$C_{3-10}$ cycloalkyl which is substituted with 1–3 substituents chosen from the group consisting of $C_{2-10}$ alkyl and $C_{3-12}$ cycloalkyl; said substituted $C_{3-10}$ cycloalkyl further optionally substituted with 1–3 substituents chosen from the group consisting of OH, $C_{1-10}$ alkoxy, $C_{3-12}$ cycloalkoxy, halogen halo($C_{1-10}$)alkyl, =NOH, =NOCONH$_2$, $CO_2H$ and =O;

$C_{3-10}$cycloalkenyl which is optionally substituted with 1–3 substituents chosen from the group consisting of OH, $C_{1-10}$alkyl, $C_{3-12}$ cycloalkyl, $C_{1-10}$ alkoxy, $C_{3-12}$ cycloalkoxy, halogen, halo($C_{1-10}$)alkyl, =NOH, =NOCONH$_2$, $CO_2H$ and =O;

$C_{3-12}$ cycloalkyl($C_{1-10}$)alkyl wherein the cycloalkyl portion is substituted with 1–3 substituents chosen from the group consisting of $C_{1-10}$ alkyl, and $C_{3-12}$ cycloalkyl; said substituted $C_{3-12}$ cycloalkyl($C_{1-10}$)alkyl further optionally substituted with 1–3 substituents chosen from the group consisting of OH, $C_{1-10}$ alkoxy, $C_{3-12}$ cycloalkoxy, =NOH =NOCONH$_2$, and $CO_2H$;

aryl which is substituted with 1–3 substituents chosen from the group consisting of amido, $C_{1-10}$ alkylamido, and $C_{1-10}$ dialkylamido; said substituted aryl further optionally substituted with 1–3 substituents chosen from the group consisting of $C_{1-10}$ alkyl, $C_{3-12}$ cycloalkyl, OH, halogen, $C_{1-10}$ alkoxy, $C_{3-12}$ cycloalkoxy, $NH_2$, $C_{1-10}$ alkylamino, $C_{1-10}$ dialkylamino, phenyl and benzyl;

ar($C_{1-4}$)alkyl wherein the aryl moiety is substituted with 1–3 substituents chosen from the group consisting of carboxy, $C_{1-10}$ alkylcarboxy, hydroxy($C_{1-10}$)alkoxy, nitro, benzyloxy, heterocyclyl, $C_{1-10}$ cycloalkyl($C_{3-12}$)alkyloxy, ar($C_{1-10}$)alkyloxy, aryloxy, amino($C_{1-10}$)alkoxy, $C_{1-10}$ alkylamino($C_{1-10}$)alkoxy, heteroaryloxy, heteroar($C_{1-10}$)alkyloxy, heterocyclyloxy, $C_{1-10}$ alkoxy and $C_{3-12}$ cycloalkoxy; said alkoxy and cycloalkoxy substituted on a carbon with hydroxy and said heterocyclyl is optionally substituted with $C_{1-10}$ alkyl and wherein the alkyl moiety of said ar($C_{1-4}$)alkyl is optionally substituted with OH, halogen, $C_{1-10}$ alkoxy or $C_{3-12}$ cycloalkoxy; said alkoxy and cycloalkoxy being optionally substituted in one position at the alkyl moiety with hydroxy; and said substituted ar($C_{1-4}$)alkyl further optionally substituted with 1–3 substituents chosen from the group consisting of halogen, hydroxy, trihalocarbon, $C_{1-10}$ alkyl, $C_{3-12}$ cycloalkyl, $C_{1-10}$ alkoxy and $C_{3-12}$ cycloalkoxy;

heterocyclyl which is substituted on the carbons or nitrogens of the ring with 1–3 substituents chosen from the group consisting of carbamyl, $C_{1-10}$ acylamino and $C_{1-10}$ alkylsulfonylamino; said substituted heterocyclyl further optionally substituted with 1–3 substituents chosen from the group consisting of $C_{1-10}$ alkyl, OH, halogen, $C_{1-10}$ alkoxy, $C_{3-12}$ cycloalkoxy, $NH_2$, $C_{1-10}$ alkylamino, $C_{1-10}$ dialkylamino, amido, $C_{1-10}$ alkylamido, $C_{1-10}$ dialkylamido, phenyl and benzyl;

heterocyclyl($C_1$–$C_4$)alkyl wherein said heterocyclyl moiety is substituted on the carbons or nitrogens of the ring with 1–3 substituents chosen from the group consisting of $C_{1-10}$ acylamino, $C_{1-10}$ alkylsulfonylamino, and $C_{1-10}$ alkyl, said $C_{1-10}$ alkyl substituted with OH, $C_{1-10}$ alkoxy, $C_{3-12}$ cycloalkoxy, $C_{3-12}$ cycloalkyl, halogen or halo($C_{1-10}$)alkyl; said substituted heterocyclyl($C_1$–$C_4$)alkyl further optionally substituted with 1–3 substituents chosen from the group consisting of $C_{1-10}$ alkyl, $C_{3-12}$ cycloalkyl, OH, halogen, $C_{1-10}$ alkoxy, $C_{3-12}$ cycloalkoxy, $NH_2$, $C_{1-10}$ alkylamino, $C_{1-10}$ dialkylamino, amido, $C_{1-10}$ alkylamido and $C_{1-10}$ dialkylamido;

heteroaryl is optionally substituted with 1–3 substitutents chosen from the group consisting of $C_{1-10}$ alkyl, $C_{3-12}$ cycloalkyl, halogen, nitro, $CF_3$, $C_{1-10}$ alkoxy and $C_{3-12}$ cycloalkoxy and heteroaryl($C_{1-4}$)alkyl, wherein the heteroaryl moiety is substituted with nitro; said heteroaryl($C_{1-4}$)alkyl further optionally substituted with 1–3 substituents chosen from the group consisting of $C_{1-10}$ alkyl, $C_{3-12}$ cycloalkyl, halogen, trihalocarbon, $C_{1-10}$ alkoxy and $C_{3-12}$ cycloalkoxy; and provided that at least one of $R^3$, $R^{6a}$, $R^{6b}$ and $R^8$ is B.

10. A pharmaceutical composition comprising a compound of the formula (I):

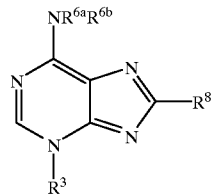

(I)

and pharmaceutically acceptable salts thereof,
wherein $R^3$, $R^{6a}$, $R^{6b}$, and $R^8$ is selected from the group consisting of A and B,
wherein A is selected from the group consisting of hydrogen;
$C_{1-10}$ alkyl which is unbranched or branched and is optionally substituted with 1–3 substituents chosen from the group consisting of OH, $C_{1-10}$ alkoxy, $C_{3-12}$ cycloalkoxy, halogen $=NOH$, $=NOCONH_2$, $CO_2H$, $=O$ and benzyloxy; said benzyloxy optionally substituted with 1–3 substituents chosen from the group consisting of halogen, $C_{1-10}$ alkyl, $C_{3-12}$ cycloalkyl, $C_{1-10}$ alkoxy and $C_{3-12}$ cycloalkoxy;

$C_{2-10}$ alkenyl which is unbranched or branched and is optionally substituted with 1–3 substituents chosen from the group consisting of OH, $C_{3-12}$ cycloalkyl, $C_{1-10}$ alkoxy, $C_{3-12}$ cycloalkoxy, halogen, $=NOH$, $=NOCONH_2$, $CO_2H$ and $=O$;

$C_{3-10}$ cycloalkyl which is optionally substituted with 1–3 substituents chosen from the group consisting of OH, $C_{1-10}$ alkyl, $C_{3-12}$ cycloalkyl, $C_{1-10}$ alkoxy, $C_{1-10}$ alkoxy, $C_{3-12}$ cycloalkoxy, halogen, halo($C_{1-10}$)alkyl, $=NOH$, $=NOCONH_2$, $CO_2H$ and $=O$;

$C_{3-10}$ cycloalkenyl which is optionally substituted with 1–3 substituents chosen from the group consisting of OH, $C_{1-10}$ alkyl, $C_{3-12}$ cycloalkyl, $C_{1-10}$ alkoxy, $C_{3-12}$ cycloalkoxy, halogen, halo($C_{1-10}$)alkyl, $=NOH$, $=NOCONH_2$, $CO_2H$ and $=O$;

$C_{3-12}$ cycloalkyl($C_{1-10}$)alkyl wherein the cycloalkyl portion is optionally substituted with 1–3 substituents chosen from the group consisting of OH, $C_{1-10}$ alkyl, $C_{3-12}$ cycloalkyl, $C_{1-10}$ alkoxy, $C_{3-12}$ cycloalkoxy, halogen, halo($C_{1-10}$)alkyl, $=NOH$, $=NOCONH_2$, $CO_2H$ and $=O$;

aryl which is optionally substituted with 1–3 substituents chosen from the group consisting of $C_{1-10}$ alkyl, $C_{3-12}$ cycloalkyl, OH, halogen, $C_{1-10}$ alkoxy, $C_{3-12}$ cycloalkoxy, $NH_2$, $C_{1-10}$ alkylamino, $C_{1-10}$ dialkylamino, carbamyl, amido, $C_{1-10}$ alkylamido, $C_{1-10}$ dialkylamido, $C_{1-10}$ acylamino, $C_{1-10}$alkysulfonylamino, phenyl and benzyl;

ar($C_{1-4}$)alkyl wherein the aryl moiety is optionally substituted with 1–3 substituents chosen from the group consisting of carboxy, $C_{1-10}$ alkylcarboxy, halogen, hydroxy, hydroxy($C_{1-10}$)alkoxy, nitro, trihalocarbon, benzyloxy, heterocyclyl, $C_{1-10}$ cycloalkyl($C_{3-12}$)alkyloxy, ar($C_{1-10}$)alkyloxy, aryloxy, amino($C_{1-10}$)alkoxy, $C_{1-10}$ alkylamino($C_{1-10}$)alkoxy, heteroaryloxy, heteroar($C_{1-10}$)alkyloxy, heterocyclyloxy, $C_{1-10}$ alkyl, $C_{3-12}$ cycloalkyl, $C_{1-10}$ alkoxy and $C_{3-12}$ cycloalkoxy; said alkoxy and cycloalkoxy optionally substituted on a carbon with hydroxy and said heterocyclyl is optionally substituted with $C_{1-10}$ alkyl; and wherein the alkyl moiety of said ar($C_{1-4}$)alkyl is optionally substituted with OH, halogen, $C_{1-10}$ alkoxy or $C_{3-12}$ cycloalkoxy; said alkoxy and cycloalkoxy being optionally substituted in one position at the alkyl moiety with hydroxy;

heterocyclyl which is optionally substituted on the carbons or nitrogens of the ring with 1–3 substituents chosen from the group consisting of $C_{1-10}$ alkyl, OH, halogen, $C_{1-10}$ alkoxy, $C_{3-12}$ cycloalkoxy, $NH_2$, $C_{1-10}$ alkylamino, $C_{1-10}$ dialkylamino, amido, $C_{1-10}$ alkylamido, $C_{1-10}$ dialkylamido, $C_{1-10}$ acylamino, $C_{1-10}$ alkylsulfonylamino, phenyl and benzyl;

heterocycly($C_1$–$C_4$)alkyl wherein said heterocyclyl moiety is optionally substituted on the carbons or nitrogens of the ring with 1–3 substituents chosen from the group consisting of $C_{1-10}$alkyl, $C_{3-12}$ cycloalkyl, OH, halogen, $C_{1-10}$ alkoxy, $C_{3-12}$ cycloalkoxy, $NH_2$, $C_{1-10}$ $C_{1-10}$ dialkylamino, carbamyl, amido, $C_{1-10}$ alkylamido, $C_{1-10}$ dialkylamido, $C_{1-10}$ acylamino, $C_{1-10}$ alkylsulfonylamino, phenyl and benzyl, and wherein said alkyl moiety is optionally substituted with OH, $C_{1-10}$ alkoxy, $C_{3-12}$ cycloalkoxy, $C_{3-12}$ cycloalkyl, halogen or halo($C_{1-10}$)alkyl;

heteroaryl, which is optionally substituted with 1–3 substituents chosen from the group consisting of $C_{1-10}$ alkyl, $C_{3-12}$ cycloalkyl, halogen, nitro, $CF_3$, $C_{1-10}$ alkoxy and $C_{3-12}$ cycloalkoxy; and heteroaryl($C_{1-4}$)alkyl, wherein the heteroaryl moiety is optionally substituted with 1–3 substituents chosen from the group consisting of $C_{1-10}$ alkyl, $C_{3-12}$ cycloalkyl, halogen, nitro trihalocarbon, $C_{1-10}$ alkoxy and $C_{3-12}$ cycloalkoxy; and B is selected from the group consisting of $C_{1-10}$ alkyl which is unbranched or branched and is substituted with 1–3 substituents chosen from the group consisting of benzyloxy, methylenedioxybenzyloxy, methyl enedioxyphenyl, pyridylmethoxy, thienylmethoxy and alkylamino; said substituents optionally substituted with 1–3 substituents chosen from the group consisting of halogen, $C_{1-10}$ alkyl, $C_{3-12}$ cycloalkyl, $C_{1-10}$ alkoxy, $C_{3-12}$ cycloalkoxy and oxo; said substituted $C_{1-10}$ alkyl further optionally substituted with 1–3 substituents chosen from the group consisting of OH, $C_{1-10}$ alkoxy, $C_{3-12}$ cycloalkoxy, halogen, =NOH, =NOCONH$_2$, CO$_2$H, and =O;

$C_{2-10}$ alkenyl which is unbranched or branched and is optionally substituted with 1–3 substituents chosen from the group consisting of OH, $C_{3-12}$ cycloalkyl, $C_{1-10}$ alkoxy, $C_{3-12}$ cycloalkoxy, halogen, =NOH, =NOCONH$_2$, CO$_2$H and =O;

$C_{3-10}$ cycloalkyl which is substituted with 1–3 substituents chosen from the group consisting of $C_{2-10}$ alkyl and $C_{3-12}$ cycloalkyl; said substituted $C_{3-10}$ cycloalkyl further optionally substituted with 1–3 substituents chosen from the group consisting of OH, $C_{1-10}$ alkoxy, $C_{3-12}$ cycloalkoxy, halogen halo($C_{1-10}$) alkyl, =NOH, =NOCONH$_2$, CO$_2$H and =O;

$C_{3-10}$ cycloalkenyl which is optionally substituted with 1–3 substituents chosen from the group consisting of OH, $C_{1-10}$ alkyl, $C_{3-12}$ cycloalkyl, $C_{1-10}$ alkoxy, $C_{3-12}$ cycloalkoxy, halogen, halo($C_{1-10}$)alkyl, =NOH, =NOCONH$_2$, CO$_2$H and =O;

$C_{3-12}$ cycloalkyl($C_{1-10}$)alkyl wherein the cycloalkyl portion is substituted with 1–3, substituents chosen from the group consisting of $C_{1-10}$ alkyl, and $C_{3-12}$ cycloalkyl; said substituted $C_{3-12}$ cycloalkyl($C_{1-10}$) alkyl further optionally substituted with 1–3 substituents chosen from the group consisting of OH, $C_{1-10}$ alkoxy, $C_{3-12}$ cycloalkoxy, =NOH, =NOCONH$_2$, and CO$_2$H;

aryl which is substituted with 1–3 substituents chosen from the group consisting of amido, $C_{1-10}$ alkylamido, and $C_{1-10}$ dialkylamido; said substituted aryl further optionally substituted with 1–3 substituents chosen from the group consisting of $C_{1-10}$ alkyl, $C_{3-12}$ cycloalkyl, OH, halogen, $C_{1-10}$ alkoxy, $C_{3-12}$ cycloalkoxy, NH$_2$, $C_{1-10}$ alkylamino, $C_{1-10}$ dialkylamino, phenyl and benzyl;

ar($C_{1-4}$)alkyl wherein the aryl moiety is substituted with 1–3 substituents chosen from the group consisting of carboxy, $C_{1-10}$ alkylcarboxy, hydroxy($C_{1-10}$)alkoxy, nitro, benzyloxy, heterocyclyl, $C_{1-10}$ cycloalkyl($C_{3-12}$)alkyloxy, ar($C_{1-10}$)alkyloxy, aryloxy, amino($C_{1-10}$)alkoxy, $C_{1-10}$ alkylamino($C_{1-10}$)alkoxy, heteroaryloxy, heteroar($C_{1-10}$)alkyloxy, heterocyclyloxy, $C_{1-10}$ alkoxy and $C_{3-12}$ cycloalkoxy; said alkoxy and cycloalkoxy substituted on a carbon with hydroxy and said heterocyclyl is optionally substituted with $C_{1-10}$ alkyl and wherein the alkyl moiety of said ar ($C_{1-4}$)alkyl is optionally substituted with OH, halogen, $C_{1-10}$ alkoxy or $C_{3-12}$ cycloalkoxy; said alkoxy and cycloalkoxy being optionally substituted in one position at the alkyl moiety with hydroxy; and said substituted ar($C_{1-4}$) alkyl further optionally substituted with 1–3 substituents chosen from the group consisting of halogen, hydroxy, trihalocarbon, $C_{1-10}$ alkyl, $C_{3-12}$ cycloalkyl, $C_{1-10}$ alkoxy and $C_{3-12}$ cycloalkoxy;

heterocyclyl which is substituted on the carbons or nitrogens of the ring with 1–3 substituents chosen from the group consisting of carbamyl, $C_{1-10}$ acylamino and $C_{1-10}$ alkylsulfonylamino; said substituted heterocyclyl further optionally substituted with 1–3 substituents chosen from the group consisting of $C_{1-10}$ alkyl, OH, halogen, $C_{1-10}$ alkoxy, $C_{3-12}$ cycloalkoxy, NH$_2$, $C_{1-10}$ alkylamino, $C_{1-10}$ dialkylamino, amido, $C_{1-10}$ alkylamido, $C_{1-10}$ dialkylamido, phenyl and benzyl;

heterocyclyl($C_1$–$C_4$)alkyl wherein said heterocyclyl moiety is substituted on the carbons or nitrogens of the ring with 1–3 substituents chosen from the group consisting of $C_{1-10}$ acylamino, $C_{1-10}$ alkylsulfonylamino, and $C_{1-10}$ alkyl, said $C_{1-10}$ alkyl substituted with OH, $C_{1-10}$ alkoxy, $C_{3-12}$ cycloalkoxy, $C_{3-12}$ cycloalkyl, halogen or halo($C_{1-10}$)alkyl; said substituted heterocyclyl($C_1$–$C_4$)alkyl further optionally substituted with 1–3 substituents chosen from the group consisting of $C_{1-10}$ alkyl, $C_{3-12}$ cycloalkyl, OH, halogen, $C_{1-10}$ alkoxy, $C_{3-12}$ cycloalkoxy, NH$_2$, $C_{1-10}$ alkylamino, $C_{1-10}$ dialkylamino, amido, $C_{1-10}$ alkylamido and $C_{1-10}$ dialkylamido;

heteroaryl is optionally substituted with 1–3 substitutents chosen from the group consisting of $C_{1-10}$ alkyl, $C_{3-12}$ cycloalkyl, halogen, nitro, $CF_3$, $C_{1-10}$ alkoxy and $C_{3-12}$ cycloalkoxy; and heteroaryl($C_{1-4}$)alkyl, wherein the heteroaryl moiety is substituted with nitro; said heteroaryl($C_{1-4}$)alkyl further optionally substituted with 1–3 substituents chosen from the group consisting of $C_{1-10}$ alkyl $C_{3-12}$ cycloalkyl, halogen, trihalocarbon, $C_{1-10}$ alkoxy and $C_{3-12}$ cycloalkoxy; and provided that at least one of $R^3$, $R^{6a}$, $R^{6b}$ and $R^8$ is B;

and a pharmaceutically acceptable excipient.

11. A compound of claim 1 selected from the group consisting of 6-amino-3-[(3-cyclopentyloxy-4-methoxy) benzyl]-8-[(1-(2-methoxy)benzyloxy-1-methyl)ethyl]-3H-purine; 6-amino-3-[(3-cyclopentyloxy-4-methoxy)benzyl]-8-[(1-(3-methoxyl)benzyloxy-1-methyl)ethyl]-3H-purine; 6-amino-3-[(3,4dimethoxy)benzyl]-8-[(1-(4-methyl) benzyloxy-1-methyl)ethyl]-3H-purine; 6-amino-3-[(3-cyclopentyloxy-4-methoxy)benzyl]-8-[(1-(4-chloro) benzyloxy-1-methyl)ethyl]-3H-purine; 6-amino-3-[(3-cyclopentyloxy-4-methoxy)benzyl]-8-[(1-(2-fluoro) benzyloxy-1-methyl)ethyl]-3H-purine; 6-amino-3-[(3-cyclopentyloxy-4-methoxy)benzyl]-8-[(1-(3-fluoro) benzyloxy-1-methyl)ethyl]-3H-purine; 6-amino-3-[(3-cyclopentyloxy-4-methoxy)benzyl]-8-[(1-(3,5-dimethoxy) benzyloxy-1-methyl)ethyl]-3H-purine; 6-amino-3-[(3-cyclopentyloxy-4-methoxy)benzyl]-8-[(1-(3,4-dimethoxy) benzyloxy-1-methyl)ethyl]-3H-purine; 6-amino-3-[(3-cyclopentyloxy-4-methoxy)benzyl]-8-[(1-(3,4-fluoro) benzyloxy-1-methyl)ethyl]-3H-purine; 6-amino-3-[(3- cyclopentyloxy-4-methoxy)benzyl]-8-[(3,4-methylenedioxybenzyloxy-1-methyl)ethyl]-3H-purine; 6-amino-3-[(3-cyclopentyloxy-4-methoxy)benzyl]-8-[(2-thienylmethoxy-1-methyl)ethyl]-3H-purine; 6-amino-3-[(3-cyclopentyloxy-4-methoxy)benzyl]-8-[(3-thienylmethoxy-1-methyl)ethyl]-3H-purine; 6-amino-3-[(3-cyclopentyloxy-4-methoxy)benzyl]-8-[(1-(1-oxo-octyl)amino-1-methyl)ethyl]-3H-purine; amino-3-(3,4-methylenedioxybenzyl)-8-[1-(4-fluorobenzyloxy)-1-methyl-ethyl]-3H-purine; 6-amino-3-[(3-cyclopentyloxy-4-methoxy)benzyl]-8-[1-(4-pyridylmethoxy)-1-methyl-ethyl]-3H-purine; 6-ethylamino-3-(3-benzyloxy-4-methoxybenzyl)-8-isopropyl-3H-purine; 3-[(3-benzyloxy-4-methoxy)benzyl-8-[(1-benzyloxy-1-methyl)-ethyl]-6-ethylamino-3H-purine; 6-Amino-3-(3-cyclopentyloxy-4-methoxy-benzyl)-8-[1-(4-methoxybenzyloxy)-1-methyl-ethyl]-3H-purine; 6-Amino-3-(3-cyclopentyloxy-4-methoxy-benzyl)-8-(1-methylethenyl)-3H-purine; 6-Amino-8-benzyloxymethyl-3-(3-cyclopentyloxy-4-methoxy-benzyl)-3H-purine; 6-amino-8-[(1-benzyloxy-1-methyl)ethyl]-3-[(3-cyclopentyloxy-4-methoxy)benzyl]-3H-purine; 6-Amino-3-(3-cyclopentyloxy-4-methoxybenzyl)-8-[1-(4-fluorobenzyloxy)-1-methyl-ethyl]-3H-purine; 8-[(1-benzyloxy-1-methyl)ethyl]-3-[(3-cyclopentyloxy-4-methoxy)benzyl]-6-ethylamino-3H-purine; 6-ethylamino-8-benzyloxymethyl-3-(3-cyclopentyloxy-4-methoxy-benzyl)-3H-purine; 6-ethylamino-3-(3,4-methylenedioxybenzyl)-8-isopropyl-3H-purine; 6-Amino-3-(3,4-dimethoxybenzyl)-8-[1-(4-fluorobenzyloxy)-1-methylethyl]-3H-purine; 6-amino-8-(1-benzyloxy-1-methylethyl)-3-(3,4-dimethoxybenzyl)-3H-purine; 6-amino-3-[(3-benzyloxy-4-methoxy)benzyl]-8-[(1-benzyloxy-1-methyl)ethyl]-3H-purine; 6-Amino-3-(3,4-dimethoxybenzyl)-8-(1-methylethenyl)-3H-purine; 6-amino-3-((3-benzyloxy-4-methoxy)-benzyl)-8-isopropyl-3H-purine; 3-(3-benzyloxy-4-nitro-benzyl)-6-ethylamino-8-isopropyl-3H-purine; 3-[cyclopentyloxy-4-methoxy)benzyl]-6-ethylamino-8-(1-methyl-ethenyl)-3H-purine; and pharmaceutically acceptable salts thereof.

* * * * *